United States Patent
Batinic-Haberle et al.

(10) Patent No.: US 11,344,574 B2
(45) Date of Patent: May 31, 2022

(54) FLUORO SUBSTITUTED PORPHYRIN COMPOUNDS, PHARMACEUTICAL COMPOSITIONS COMPRISING THE SAME, AND METHODS OF PREPARING AND USING THE SAME

(71) Applicant: Duke University, Durham, NC (US)

(72) Inventors: Ines Batinic-Haberle, Durham, NC (US); Artak Tovmasyan, Durham, NC (US); Ivan Spasojevic, Durham, NC (US)

(73) Assignee: Duke University, Durham, NC (US)

( * ) Notice: Subject to any disclaimer, the term of this patent is extended or adjusted under 35 U.S.C. 154(b) by 193 days.

(21) Appl. No.: 16/645,907

(22) PCT Filed: Sep. 26, 2018

(86) PCT No.: PCT/US2018/052826
§ 371 (c)(1),
(2) Date: Mar. 10, 2020

(87) PCT Pub. No.: WO2019/067523
PCT Pub. Date: Apr. 4, 2019

(65) Prior Publication Data
US 2021/0361702 A1 Nov. 25, 2021

Related U.S. Application Data

(60) Provisional application No. 62/565,436, filed on Sep. 29, 2017.

(51) Int. Cl.
| | | |
|---|---|---|
| *C07F 13/00* | (2006.01) | |
| *A61K 33/32* | (2006.01) | |
| *A61P 39/00* | (2006.01) | |
| *A61P 35/00* | (2006.01) | |
| *A61K 31/375* | (2006.01) | |

(52) U.S. Cl.
CPC ............ *A61K 33/32* (2013.01); *A61K 31/375* (2013.01); *A61P 35/00* (2018.01); *A61P 39/00* (2018.01); *C07F 13/005* (2013.01)

(58) Field of Classification Search
CPC .... C07D 487/22; A61K 33/22; A61K 31/555; A61K 31/409; A61P 35/00; C07F 13/005
USPC .......................................... 540/145; 514/184
See application file for complete search history.

(56) References Cited

U.S. PATENT DOCUMENTS

| | | |
|---|---|---|
| 8,618,089 B2 | 12/2013 | Batinic-Haberle et al. |
| 2002/0042407 A1 | 4/2002 | Fridovich et al. |
| 2006/0199792 A1 | 9/2006 | Groves et al. |
| 2007/0149498 A1 | 6/2007 | Crapo et al. |
| 2011/0275606 A1 | 11/2011 | Batinic-Haberle et al. |
| 2015/0344509 A1 | 12/2015 | Haberle et al. |
| 2016/0324868 A1 | 11/2016 | Ji et al. |

FOREIGN PATENT DOCUMENTS

| | | |
|---|---|---|
| WO | 2008095366 A1 | 8/2008 |
| WO | 2010080881 A1 | 7/2010 |
| WO | 2015034777 A1 | 3/2015 |
| WO | 2015034778 A1 | 3/2015 |
| WO | 2015112586 A1 | 7/2015 |
| WO | 2015112588 A1 | 7/2015 |
| WO | 2018118891 | 6/2018 |
| WO | 2018237249 A1 | 12/2018 |
| WO | 2019067523 A1 | 4/2019 |

OTHER PUBLICATIONS

Abdollah, F et al. "A competing-risks analysis of survival after alternative treatment modalities for prostate cancer patients: 1988-2006" European Urology, 59:88-95 (2011).
Allen, B. G et al. "Pharmacological ascorbate enhances chemo-radio-sensitization in brain and lung cancer" Free Radical Biology & Medicine, 53:S39 (2012).
Aluise, C. D et al. "2-Mercaptoethane sulfonate prevents doxorubicin induced plasma protein oxidation and TNF-a Yelease: implications for the reactive oxygen species mediated mechanisms of chemobrain" Free Radical Biology & Medicine, 11:1630-1638 (2011).
American Cancer Society, "Cancer Facts & Figures 2014" American Cancer Society, Inc., 72 pages (2014).
Amii, H et al. "Flow microreactor synthesis in organo-fluorine chemistry" Beilstein Journal of Organic Chemistry, 9:2793-2802 (2013).
Archambeau, J et al. "Superoxide dismutase mimic, MnTE-2-PyP5+ ameliorates acute and chronic proctitis following focal proton irradiation of the rat rectum" Redox Biology, 1:599-607 (2013).
Bache, S. T et al. "Investigating the accuracy of microstereotactic-body-radiotherapy utilizing anatomically accurate 3D printed rodentmorphic dosimeters" Medical Physics, 42(2):846 (2015).
Bao, F et al. "Hydroxyl radicals generated in the rat spinal cord at the level produced by impact injury induce cell death by necrosis and apoptosis: protection by a metalloporphyrin" Neuroscience, 126(2):285-295 (2004).
Batinic-Haberle, I. et al. "Design of Mn porphyrins for treating oxidative stress injuries and their redox-based regulation of cellular transcriptional activities" Amino Acids, 42(1):95-113 (2012).
Batinic-Haberle, I. et al. "Diverse functions of cationic Mn(lll) N-substituted pyridylporphyrins, recognized as SOD mimics" Free Radicical Biology & Medicine, 51 (5): 1035-1053 (2011).
Batinic-Haberle, I. et al. "Mechanistic considerations of the therapeutic effects of Mn porphyrins, commonly regarded as SOD mimics" Anticancer Therapy: Lessons from Brain and Lymphoma Studies, Free Radical Biol & Med, 65 (Supplement 2):S120-121 (2013).

(Continued)

*Primary Examiner* — Charanjit Aulakh
(74) *Attorney, Agent, or Firm* — Myers Bigel, P.A.

(57) ABSTRACT

Provided herein are fluoro-substituted porphyrin compounds, such as those having a structure represented by Formula (I), wherein $R^1$ is a C1-C8 alkyl that is substituted with at least 1 fluorine (e.g., a C1-C8 alkyl substituted with 1-17 fluorine atoms); and X is an anion (e.g. a halogen ion (e.g., chloride, etc.), $PF_6$, tosylate, besylate, and/or mesylate). Also provided herein are methods of making the fluoro-substituted porphyrin compounds, pharmaceutical formulations containing the same, and methods of use thereof.

20 Claims, 18 Drawing Sheets

(56) References Cited

OTHER PUBLICATIONS

Batinic-Haberle, I. et al. "Superoxide dismutase mimics: chemistry, pharmacology, and therapeutic potential" Antioxidants & Redox Signal, 13(6):877-918 (2010).
Batinic-Haberle, I et al. "52 Chemistry, biology and medical effects of water soluble metalloporphyrins" Handbook of Porphyrin Science, 11:291-393 (2011).
Batinic-Haberle, I et al. "A Combination of Two Antioxidants (An SOD Mimic and Ascorbate) Produces a Pro-Oxidative Effect Forcing *Escherichia coli* to Adapt Via Induction of oxyR Regulon" Anticancer Agents in Medicinal Chemistry, 11 (4):329-340 (2011).
Batinic-Haberle, I et al. "An educational overview of the chemistry, biochemistry and therapeutic aspects of Mn porphyrins - From superoxide dismutation to H202-driven pathways" Redox Biology, 5:43-65 (2015).
Batinic-Haberle, I et al. "Complex chemistry and biology of redox-active compounds, commonly known as SOD mimics, affect their therapeutic effects" Antioxidants & Redox Signaling, 20(15):2323-2325 (2014).
Batinic-Haberle, I. et al. "Manganese(lll) Meso Tetrakis Ortho N-alkylpyridylporphyrins. Synthesis, Characterization and Catalysis of 02- Dismutation" Journal of the Chemical Society, Dalton Transactions, 13(13):2689-2696 (2002).
Batinic-Haberle, I et al. "New class of potent catalysts of 02.-dismutation. Mn(III) methoxyethylpyridyl- and methoxyethylimidazolylpyridylporphyrins" Dalton Transactions, 11:1696-1702 (2004).
Batinic-Haberle, I et al. "SOD therapeutics: latest insights into their structure-activity relationships and impact on the cellular redox-based signaling pathways" Antioxidants & redox signaling, 20(15):2372-2415 (2014).
Batinic-Haberle, I et al. "The complex mechanistic aspects of redox-active compounds, commonly regarded as SOD mimics" BioInorganic Reaction Mechanisms, 9(1-4):35-58 (2013).
Batinic-Haberle, I. et al. "The Ortho Effect Makes Manganese (III) Meso-Tetrakis(N-methylpyridinium-2-yl)Porphyrin (MnTM-2-PyP) a Powerful and Potentially Useful Superoxide Dismutase Mimic" The Journal of Biological Chemistry, 273(38):24521-24528 (1998).
Batinic-Haberle, et al. "Relationship among Redox Potentials, Proton Dissociation Constants of Pyrrolic Nitrogens, and in Vivo and in Vitro Superoxide Dismutating Activities of Manganese(lll) and Iron(lll) Water-Soluble Porphyrins" Inorganic Chemistry, 38:4011-4022 (1999).
Beck L. A et al. "Dupilumab treatment in adults with moderate-to-severe atopic dermatitis" New England Journal of Medicine, 371 (2): 130-139 (2014).
Benov, L. et al. "Protein damage by photo-activated Zn(ll) N-alkylpyridylporphyrins" Amino Acids, 42(1): 117-128 (2012).
Bhattacharyya, J. et al. "A paclitaxel-loaded recombinant polypeptide nanoparticle outperforms Abraxane in multiple murine cancer models" Nature Communications, 6:7939 (2015).
Birer, S. R et al. "Inhibition of the continuum of radiation-induced normal tissue injury by a redox-active Mn porphyrin" Radiation Research, 188(1):94:104 (2017).
Bottino R. et al. "Preservation of human islet cell functional mass by anti-oxidative action of a novel SOD mimic compound" Diabetes, 51(8):2561-2567 (2002).
Bottino R et al. "Response of human islets to isolation stress and the effect of antioxidant treatment" Diabetes, 53 (10):2559-2568 (2004).
Breckwoldt, M. O. et al. "Multiparametric optical analysis of mitochondrial redox signals during neuronal physiology and pathology in vivo" Nature Medicine, 20(5):555-560 (2014).
Bristol-Myers Squibb "FDA Oncology Tools Approval Summary for Cisplatin for Metastatic Ovarian Tumors. Food and Drug Administration, Center for Drug Evaluation and Research" Archived from the original on Feb. 8, 2008. (1978).
Brizel D. M. et al. "Phase III randomized trial of amifostine as a radioprotector in head and neck cancer" Journal of Clinical Oncology, 18(19):3339-3345 (2000).
Butler, J.M., Jr., et al. "A phase III, double-blind, placebo-controlled prospective randomized clinical trial of d-threo-methylphenidate HCI in brain tumor patients receiving radiation therapy" Int J of Radiatian Oncol, Biol, Phys, 69 (5):1496-1501 (2007).
Campa M. et al. "A review of biologic therapies targeting IL-23 and IL-17 for use in moderate-to-severe plaque psoriasis" Dermatology and Therapy, 6(1): 1-12 (2016).
Cao, Y. T. et al. "Observation of incipient tumor angiogenesis that is independent of hypoxia and hypoxia inducible factor-1 activation" Cancer Research, 65(13):5498-5505 (2005).
Celic, T. et al. "Mn porphyrin-based SOD mimic, MnTnHex-2-PyP(5+), and non-SOD mimic, MnTBAP(3-), suppressed rat spinal cord ischemia/reperfusion injury via NF-kappaB pathways" Free Radical Research, 48(12): 1426-1442 (2014).
Chen, Q. et al. "Ascorbate in pharmacologic concentrations selectively generates ascorbate radical and hydrogen peroxide in extracellular fluid in vivo" Proceedings of the National Academy of Sciences, 104(21 ):8749-8754 (2007).
Chen, Q. et al. "Pharmacologic doses of ascorbate act as a prooxidant and decrease growth of aggressive tumor xenografts in mice" Proceedings of the National Academy of Sciences, 105(32):11105-11109 (2008).
Choudhury, K. R et al. "Dynamic treatment effect (DTE) curves reveal the mode of action for standard and experimental cancer therapies" Oncotarget, 6(16):14656-1468 (2015).
Cong, Z. X. et al. "ERK and PI3K signaling cascades induce Nrf2 activation and regulate cell viability partly through Nrf2 in human glioblastoma cells" Oncology Reports, 30(2)715-722 (2013).
Cotrim A. P. et al. "Kinetics of tempol for prevention of xerostomia following head and neck irradiation in a mouse model" Clinical Cancer Research: An Official Journal of the American Association for Cancer Research, 11 (20)7564-7568 (2005).
Crawford, S. "Anti-inflammatory/antioxidant use in long-term maintenance cancer therapy: a new therapeutic approach to disease progression and recurrence" Therapeutic Advances in Medical Oncology, 6(2):52-68 (2014).
Delmastro M. M. "Modulation of redox balance leaves murine diabetogenic TH1 T cells "LAG-3-ing" behind" Diabetes, 61(7):1760-1768 (2012).
Delmastro M. M. et al. "Oxidative stress and redox modulation potential in type 1 diabetes" Clinical and Developmental Immunology, 2011:593863 (2011).
Delmastro-Greenwood, M. M. et al. "Mn porphyrin regulation of aerobic glycolysis: implications on the activation of diabetogenic immune cells" Antioxidants & Redox Signaling, 19(16):1902-1915 (2013).
Dewhirst, M. W. "Relationships between Cycling Hypoxia, HIF-1, Angiogenesis and Oxidative Stress" Radiation Research, 172(6):653-665 (2009).
Dhar, S. K et al. "Manganese superoxide dismutase is a p53-regulated gene that switches cancers between early and advanced stages" Cancer Research, 71(21):8864-8895 (2011).
Dinan, M. A. et al. "Changes in initial treatment for prostate cancer among Medicare beneficiaries, 1999-2007" International Journal of Radiation Oncology, Biology, Physics, 82(5):e781-786 (2012).
Dong, C. et al. "Loss of FBP1 by snail-mediated repression provides metabolic advantages in basal-like breast cancer" Cancer Cell, 23(3):31 6-331 (2013).
Dorai, T. et al. "Amelioration of renal ischemia-reperfusion injury with a novel protective cocktail" The Journal of Urology, 186(6):2448-2454 (2011).
Driscoll, J. et al. "Antitumor properties of 2(1H)-pyrimidinone riboside (zebularine) and its fluorinated analogues" Journal of Medicinal Chemistry, 34(11):3280-3284 (1991).
El-Batawy M. M. et al. "Topical calcineurin inhibitors in atopic dermatitis: a systematic review and meta-analysis" Journal of Dermatological Science, 54(2):76-87 (2009).

(56) References Cited

OTHER PUBLICATIONS

Elting L.S. et al. "Risk, outcomes, and costs of radiation-induced oral mucositis among patients with head-and-neck malignancies" International Journal of Radiation Oncology, Biology, Physics, 68(4):1110-1120 (2007).
Engelmann, F. M. et al. "Determination of n-octanol/water partition and membrane binding of cationic porphyrins" International Journal of Pharmaceutics, 329(1-2):12-18 (2007).
Evans, M. K. et al. "Mn porphyrin in combination with ascorbate acts as a pro-oxidant and mediates caspaseindependent cancer cell death" Free Radical Biology and Medicine, 68:302-314 (2014).
Eyerich K. "Immunology of atopic eczema: overcoming the Th1/Th2 paradigm" Allergy, 68(8):974-982 (2013).
Ezzeddine, R. et al. "Effect of Molecular Characteristics on Cellular Uptake, Subcellular Localization, and Phototoxicity of Zn(II) N-Alkylpyridylporphyrins" The Journal of Biological Chemistry, 288(51):36579-36588 (2013).
Fernandes, A. S et al. "Combined effect of the SOD mimic MnTnHex-2-PyP5+ and doxorubicin on the migration and invasiveness of breast cancer cells" Toxicology Letters, 221(S):S70-S71 (2013).
Ferrer-Sueta, G. et al. "Reactions of Manganese Porphyrins with Peroxynitrite and Carbonate Radical Anion" The Journal of Biological Chemistry, 278(30):27432-27438 (2003).
Filler, R. et al. "Fluorine in medicinal chemistry: a century of progress and a 60-year retrospective of selected highlights" Future Medicinal Chemistry, 1(5):777-791 (2009).
Forman, H. J. et al. "Signaling functions of reactive oxygen species" Biochemistry, 49(5):835-842 (2010).
Fuchs, J. et al. "Modulation of UV-light-induced skin inflammation by D-alpha-tocopherol and L-ascorbic acid: a clinical study using solar simulated radiation" Free Radical Biology and Medicine, 25(9):1006-1012 (1998).
Fugl-Meyer, A. R. et al. "On life satisfaction in male erectile dysfunction" International Journal of Impotence Research, 9(3):141-148 (1997).
Fujiwara N. et al. "miR-634 Activates the Mitochondrial Apoptosis Pathway and Enhances Chemotherapy-Induced Cytotoxicity" Cancer Research, 75(18):3890-3901 (2015).
Gad, S. C. et al. "A nonclinical safety assessment of MnTE-2-PyP, a manganese porphyrin" International Journal of Toxicology, 32(4):274-287 (2013).
Gad, S. C3 et al. "Nonclinical Safety and Toxicokinetics of MnTnBuOE-2-PyP5+ (BMX-001)" International Journal of Toxicology, 35(4):438-453 (2016).
Garofalo, M.C., et al. "A pilot study in rhesus macaques to assess the treatment efficacy of a small molecular weight catalytic metalloporphyrin antioxidant (AEOL 10150) in mitigating radiation-induced lung damage" Health Phys Society, 106(1):73-83 (2014).
Gauter-Fleckenstein, B et al. "Early and late administration of antioxidant mimic MnTE-2-PyP5+ in mitigation and treatment of radiation-induced lung damage" Free Radical Biology and Medicine, 48(8):1034-1043 (2010).
Gauter-Fleckenstein, B. et al. "Robust rat pulmonary radioprotection by a lipophilic Mn N-alkylpyridylporphyrin, WinTnHex-2-PyP+" Redox Biology, 2:400-410 (2014).
Gaye, B. et al. "Fluorinated molecules in the diagnosis and treatment of neurodegenerative diseases" Future Medicinal Chemistry, 1(5):821-823 (2009).
Geismann, C. et al. "Cytoprotection "gone astray": Nrf2 and its role in cancer" OncoTargets and Therapy, 7:1497-1518 (2014).
Gerber D. E. et al. "The impact of thrombocytopenia from temozolomide and radiation in newly diagnosed adults with high-grade gliomas" Neuro-Oncology, 9(1):47-52 (2006).
Ghoreschi K, et al. "Immunopathogenesis and role of T cells in psoriasis" Clinics in Dermatology, 25(6):574-580 (2007).
Giro C. et al. "High rate of severe radiation dermatitis during radiation therapy with concurrent cetuximab in head and neck cancer: Results of a survey in EORTC institutes" Radiotherapy and Oncology, 90(2):166-171 (2009).

Gittler J. K. et al. "Progressive activation of T(H)2/T(H)22 cytokines and selective epidermal proteins characterizes acute and chronic atopic dermatitis" Journal of Allergy Clinical Immunology, 130(6):1344-1354 (2012).
Gius, D et al. "Redox Signaling in Cancer Biology" Antioxidants & Redox Signaling, 8(7-8):1249-1252 (2006).
Gravemann, U. et al. "Hydroxamic acid and fluorinated derivatives of valproic acid: Anticonvulsant activity, neurotoxicity and teratogenicity" Neurotoxicology and Teratology, 30(5):390-394 (2008).
Gridley, D.S et al. "Radiation and a metalloporphyrin radioprotectant in a mouse prostate tumor model" Anticancer Research, 27(5A):3101-3109 (2007).
Habl G. et al. "Differentiation of irradiation and cetuximab induced skin reactions in patients with locally advanced head and neck cancer undergoing radioimmunotherapy: the HICARE protocol" BMC Cancer, 13(1):345 (2013).
Hayes, J. D. et al. "The Nrf2 regulatory network provides an interface between redox and intermediary metabolism" Trends in Biochemical Sciences, 39(4): 199-218 (2014).
Hempel, N. et al. "Manganese superoxide dismutase (Sod2) and redox-control of signaling events that drive metastasis" Anticancer Agents in Medicinal Chemistry, 11 (2):191-201 (2011).
Hoffman, K. E. et al. "Risk of late toxicity in men receiving dose-escalated hypofractionated intensity modulated prostate radiation therapy: results from a randomized trial" Int J of Radiation Oncology, Biology, Physics, 88(5): 1074-1084(2014).
Il'yasova, D et al. "Individual responses to chemotherapy-induced oxidative stress" Breast Cancer Research and Treatment, 125(2): 583-589 (2011).
International Preliminary Report on Patentability corresponding to International Patent Application No. PCT/US2018/052826 (5 pages) (dated Mar. 31, 2020).
Jaal, J. et al. "Radiation Induced Inflammatory Changes in the Mouse Bladder: The Role of Cyclooxygenase-2" Journal of Urology, 175(4):1529-1533 (2006).
Jaramillo et al. "Manganese (III) meso-tetrakis N-ethylpyridinium-2-yl porphyrin acts as a pro-oxidant to inhibit electron transport chain proteins, modulate bioenergetics, and enhance the response to chemotherapy in lymphoma cells" Free Radical Biology and Medicine, 83 (2015).
Jaramillo, M. C. et al. "Manganese Porphyrin, MnTE-2-PyP5+, Acts as a Pro-Oxidant to Potentiate Glucocorticoid-Induced Apoptosis in Lymphoma Cells" Free Radical Biology and Medicine, 52(8):1272-1284 (2012).
Jaramillo, M. C et al. "The emerging role of the Nrf2-Keap1 signaling pathway in cancer" Genes & Development, 27:2179-2191 (2013).
Jin, G. et al. "Disruption of wild-type IDH1 suppresses D-2-hydroxyglutarate production in IDH1-mutated gliomas" Cancer Research, 73(2):496-501 (2013).
Johnson L. B. et al. "Radiation enteropathy and leucocyte-endothelial cell reactions in a refined small bowel model" BMC Surgery, 4:10(2004).
Jones, D. P. "Redox potential of GSH/GSSG couple: assay and biological significance" Methods in Enzymology, 348:93-112 (2002).
Jones, D. P. et al. "Redox state of glutathione in human plasma" Free Radical Biology and Medicine, 28(4):625-635 (2000).
Jones, L. W. et al. "Effects of non-linear aerobic training on erectile dysfunction and cardiovascular function following radical prostatectomy for clinically-localized prostate cancer" European Urology, 65(5):852-855 (2014).
Jumbo-Lucioni, P. P et al. "Manganese-Based Superoxide Dismutase Mimics Modify Both Acute and Long-Term Outcome Severity in a *Drosophila melanogaster* Model of Classic Galactosemia" Antioxidants & Redox Signaling, 20 (15):2361-2371 (2014).
Jungsuwadee P. et al. "The Metalloporphyrin Antioxidant, MnTE-2-PyP, Inhibits Th2 Cell Immune Responses in an Asthma Model" International Journal of Molecular Sciences, 13(8):9785-9797 (2012).
Kachadourian, R. et al. "Syntheses and Superoxide Dismuting Activities of Partially (1-4) β-Chlorinated Derivatives of Manganese(III) meso-Tetrakis(N-ethylpyridinium-2-yl)porphyrin" Inorganic Chemistry, 38(2):391-396 (1999).

(56) References Cited

OTHER PUBLICATIONS

Keil, K. P. et al. "Influence of animal husbandry practices on void spot assay outcomes in C57BL/6J male mice" Neurourology and Urodynamics, 35(2):192-198 (2014).
Keir, S.T et al. "Cellular Redox Modulator, ortho Mn(III) meso-tetrakis(N-n-Hexylpyridinium-2-yl)porphyrin, WinTnHex-2-PyP5+ in the Treatment of Brain Tumors" Anticancer Agents in Medicinal Chemistry, 11(2):202-212 (2011).
Khan, I. et al. "Effect of potent redox-modulating manganese porphyrin, MnTM-2-PyP, on the Na(+)/H(+) exchangers NHE-1 and NHE-3 in the diabetic rat" Redox Report, 14(6):236-242 (2009).
Kimura H. et al. "Inhibition of radiation-induced up-regulation of leukocyte adhesion to endothelial cells with the platelet-activating factor inhibitor, BN52021" International Journal of Radiation, Oncology, Biology, Physics, 33 (3):627-633 (1995).
Kimura, M. et al. "Pilot Study Evaluating a Rat Model of Radiation-induced Erectile Dysfunction Using an Image-guided Microirradiator" Urology, 85(5):1214.e1-1214.e6 (2015).
Kimura, M. et al. "Radiation-induced erectile dysfunction using prostate-confined modern radiotherapy in a rat model" Journal of Sexual Medicine, 8(8):2215-2226 (2011).
Kimura, M et al. "Role of Oxidative Stress in a Rat Model of Radiation-Induced Erectile Dysfunction" Journal of Sexual Medicine, 9(6): 1535-1549 (2012).
Kirlin, W. G et al. "Glutathione redox potential in response to differentiation and enzyme inducers" Free Radical Biology & Medicine, 27(11/12):1208-1218 (1999).
Kiselyov, A. S. "Chemistry of N-fluoropyridinium salts" Chemistry Society Reviews, 34(12):1031-1037 (2005).
Klotz, L. "Active surveillance for prostate cancer: trials and tribulations" World Journal of Urology, 26(5):437-442 (2008).
Kodell, R. L. et al. "Determination of Sample Sizes for Demonstrating Efficacy of Radiation Countermeasures" Biometrics, 66(1):239-248 (2010).
Koga, F., et al. "ErbB2 and NFkappaB overexpression as predictors of chemoradiation resistance and putative targets to overcome resistance in muscle-invasive bladder cancer" PLoS One, 6(11):e27616 (2011).
Koontz, B. F. et al. "Feasibility Study of an Intensity-Modulated Radiation Model for Study of Erectile Dysfunction" Journal of Sexual Medicine, 8(2):411-418 (2011).
Koontz, B. F. et al. "Impact of Primary Gleason Grade on Risk Stratification for Gleason Score 7 Prostate Cancers" International Journal of Radiation, Oncology, Biology, Physics, 82(1):200-203 (2012).
Koontz, B. F. et al. "Phase 1 trial of neoadjuvant radiation therapy before prostatectomy for high-risk prostate cancer" International Journal of Radiation Oncology, Biology, Physics, 87(1):88-93 (2013).
Kos, I. et al. "Lipophilicity of potent porphyrin-based antioxidants: Comparison of ortho and meta isomers of Mn(III) N-alkylpyridylporphyrins" Free Radical Biology and Medicine, 47(1):72-78 (2009).
Koyama G. et al. "Novel approaches to topical psoriasis therapy" International Journal of Pharmaceutical Compounding, 19(5):357-365 (2015) ABSTRACT.
Kwei K. A. et a. "Transcriptional repression of catalase in mouse skin tumor progression" Neoplasia, 6(5):440-448 (2004).
Lakritz J. et al. "Validated High-Performance Liquid Chromatography-Electrochemical Method for Determination of Glutathione and Glutathione Disulfide in Small Tissue Samples" Analytical Biochemistry, 247(1):63-68 (1997).
Lauffer F. et al. "Target-oriented therapy: Emerging drugs for atopic dermatitis" Expert Opinion on Emerging Drugs, 21 (1):81-89 (2016).
Lee, M.Y. et al. "Senescence of cultured porcine coronary arterial endothelial cells is associated with accelerated oxidative stress and activation of NFkB" Journal of Vascular Research, 47(4):287-298 (2010).
Leu, D. et al. "CNS bioavailability and radiation protection of normal hippocampal neurogenesis by a lipophilic Mn porphyrin-based superoxide dismutase mimic, MnTnBuOE-2-PyP5+" Redox Biology, 12(C):864-871 (2017).
Levi J. A. et al. "Haemolytic anaemia after cisplatin treatment" British Medical Journal (Clin Res Ed) 282 (6281):2003-2004 (1981).
Li, C. Y. et al. "Initial Stages of Tumor Cell-Induced Angiogenesis: Evaluation Via Skin Window Chambers in Rodent Models" Journal of the National Cancer Institute, 92(2):143-147 (2000).
Li, H., et al. "Mn(III) meso-tetrakis-(N-ethylpyridinium-2-yl) porphyrin mitigates total body irradiation-induced long-term bone marrow suppression" Free Radical Biology & Medicine, 51(1):30-37 (2011).
Liang, T. et al. "Introduction of Fluorine and Fluorine-Containing Functional Groups" Angewandte Chemie International Edition, 52(32):8214-8264 (2013).
Lien, Y.-C. et al. "Phospholipase C-δ1 Is a Critical Target for Tumor Necrosis Factor Receptor-Mediated Protection against Adriamycin-Induced Cardiac Injury" Cancer Research, 66(8):4329-4338 (2006).
Lien, Y.-C. et al. "TNF receptors deficiency exacerbated adriamycin-induced cardiomyocytes apoptosis: An Insight into Fas connection" Molecular Cancer Therapeutics, 5(2):261-269 (2006).
Lin, P. et al. "Antiangiogenic gene therapy targeting the endothelium-specific receptor tyrosine kinase Tie2" Proceedings of the National Academy of Sciences of the United States of America, 95(15):8829-8834 (1998).
Ling, X. et al. "Temporal and spatial profiles of cell loss after spinal cord injury: Reduction by a metalloporphyrin" Journal of Neuroscience Research, 85(10):2175-2185 (2007).
Liu, D., et al. "Peroxynitrite generated at the level produced by spinal cord injury induces peroxidation of membrane phospholipids in normal rat cord: reduction by a metalloporphyrin" Journal of Neurotrauma, 22(10):1123-1133 (2005).
Loehrer P. J. et al. "Drugs five years later: Cisplatin" Annals of Internal Medicine, 100(5):704-713 (1984).
Lomeli N. et al. "Cisplatin-induced mitochondrial dysfunction is associated with impaired cognitive function in rats" Free Radical Biology Medicine, 102:274-286 (2017).
Mackensen, G. B. et al. "Neuroprotection from Delayed Postischemic Administration of a Metalloporphyrin Catalytic Antioxidant" The Journal of Neuroscience, 21(13):4582-4592 (2001).
Mantz, C. A. et al. "Potency preservation following conformal radiotherapy for localized prostate cancer: impact of neoadjuvant androgen blockade, treatment technique, and patient-related factors" Cancer J Scientific American, 5 (4):230-236 (1999) ABSTRACT.
Manzoor, A. A et al. "Overcoming Limitations in Nanoparticle Drug Delivery: Triggered, Intravascular Release to Improve Drug Penetration into Tumors" Cancer Research, 72(21):5566-5575 (2012).
Marullo R. et al. "Cisplatin induces a mitochondrial-ROS response that contributes to cytotoxicity depending on mitochondrial redox status and bioenergetic functions" PloS one, 8(11 ):e81162 (2013).
Mason A. R. et al. "Topical treatments for chronic plaque psoriasis" Cochrane Database System Review, 3:CD005028 (2013).
McCullagh, P et al. "Generalized Linear Models" Chapman and Hall/CRC, 2nd Edition, 526 pages (1989).
Meltzer, D. et al. "Patterns of Prostate Cancer Treatment by Clinical Stage and Age" American Journal of Public Health, 91(1):126-128 (2001).
Milosavljevic N. et al. "Nongenomic effects of cisplatin: acute inhibition of mechanosensitive transporters and channels without actin remodeling" Cancer Research, 70(19):7514-7522 (2010).
Miriyala, S. et al. "Manganese superoxide dismutase, MnSOD and its mimics" Biochimica et Biophysica Acta, 1822 (5):794-814 (2012).
Moeller, B. J. et al. "A manganese porphyrin superoxide dismutase mimetic enhances tumor radioresponsiveness" International Journal of Radiation, Oncology, Biology, Physics, 63(2):545-552 (2005).
Moeller, B.J. et al. "Pleiotropic effects of HIF-1 blockade on tumor radiosensitivity" Cancer Cell, 8(2):99-110 (2005).
Moeller, B.J et al. "Radiation activates HIF-1 to regulate vascular radiosensitivity in tumors: role of reoxygenation, free radicals, and stress granules" Cancer Cell, 5(5):429-441 (2004).
Moore T. et al. "A new LC-MS/MS method for the clinical determination of reduced and oxidized glutathione from whole

(56) References Cited

OTHER PUBLICATIONS blood" Journal of Chromatography B, Analytical Technologies in the Biomedical and Life Sciences, 929:51-55 (2013).
Morgan-Bathke M. et al. "The Rapalogue, CCI-779, improves salivary gland function following radiation" PloS one, 9 (12):e113183 (2014).
Moser, J. C. et al. "Pharmacological ascorbate and ionizing radiation (IR) increase labile iron in pancreatic cancer" Redox Biology, 2:22-27 (2013).
Moul, J. W. "Prostate specific antigen only progression of prostate cancer" The Journal of Urology, 163(6):1632-1642 (2000).
Moulder, J. E. "Future strategies for mitigation and treatment of chronic radiation-induced normal tissue injury" Seminars in Radiation Oncology, 17(2):141 -148 (2007).
Nam, R. K et al. "Incidence of complications other than urinary incontinence or erectile dysfunction after radical prostatectomy or radiotherapy for prostate cancer: a population-based cohort study" The Lancet, Oncology, 15(2):223-231 (2014).
National Institute for Health and Care Excellence, "Psoriasis: Assessment and Management of Psoriasis" National Clinical Guideline Centre, Clinical Guideline, Published: Oct. 24, 2012 (56 pages).
Needham D, et al. "A new temperature-sensitive liposome for use with mild hyperthermia: Characterization and testing in a human tumor xenograft model" Cancer Research, 60(5):1197-1201 (2000).
NRG Oncology "RTOG 0920: A Phase III Study of Postoperative Radiation Therapy (IMRT) /- Cetuximab for Locally-Advanced Resected Head and Neck Cancer" Version Date: Jan. 25, 2016 (100 pages).
Oberley-Deegan, R. E et al. "Mechanisms by Which Manganese Porphyrins Affect Signaling in Cancer Cells" Redox-Active Therapeutics, Springer US, pp. 405-431 (2015).
Oberley-Deegan, R. E. et al. "The Antioxidant, MnTE-2-PyP, Prevents Side-Effects Incurred by Prostate Cancer Irradiation" PLoS One, 7(9):e44178 (2012).
Ohebshalom, M et al. "The efficacy of sildenafil citrate following radiation therapy for prostate cancer: temporal considerations" Journal of Urology, 174(1):258-262 (2005).
Oscarsson, N. et al. "Hyperbaric Oxygen Treatment in Radiation-Induced Cystitis and Proctitis: A Prospective Cohort Study on Patient-Perceived Quality of Recovery" International Journal of Radiation, Oncology, Biology, Physics, 87 (4):670-675 (2013).
Palmer C. N. A. et al. "Common loss-of-function variants of the epidermal barrier protein filaggrin are a major predisposing factor for atopic dermatitis" Nature Genetics, 38(4):441-446 (2006).
Pfitzenmaier, J. et al. "Characterization of C4-2 Prostate Cancer Bone Metastases and Their Response to Castration" Journal of Bone and Mineral Research, 18(10):1882-1888 (2003).
Pham, Christine T.N. "Neutrophil serine proteases: specific regulators of inflammation" Natuere Reviews Immunology, 6(7):541-550 (2006).
Piganelli, J. D. et al. "A metalloporphyrin-based superoxide dismutase mimic inhibits adoptive transfer of autoimmune diabetes by a diabetogenic T-cell clone" Diabetes, 51(2):347-355 (2002).
Pisansky, T. M et al. "Tadalafil for Prevention of Erectile Dysfunction After Radiotherapy for Prostate Cancer The Radiation Therapy Oncology Group [0831] Randomized Clinical Trial" JAMA, 311(13):1300-1307 (2014).
Pollard, J. M. et al. "Radioprotective effects of manganese-containing superoxide dismutase mimics on ataxiatelangiectasia cells" Free Radical Biology and Medicine, 47(3):250-260 (2009).
Pringle S. et al. "Concise Review: Adult Salivary Gland Stem Cells and a Potential Therapy for Xerostomia" Stem Cells, 31(4):613-619 (2013).
Rabbani, Z.N. et al. "Antiangiogenic action of redox-modulating Mn(III) meso-tetrakis(N-ethylpyridinium-2-yl)porphyrin, MnTE-2-PyP(5+), via suppression of oxidative stress in a mouse model of breast tumor" Free Radicical Biol & Med, 47 (7):992-1004 (2009).
Rades D. et al. "Serious adverse effects of amifostine during radiotherapy in head and neck cancer patients" Radiotherapy and Oncology, 70(3):261-264 (2004).
Rajic, Z et al. "A new SOD mimic, Mn(lll) ortho N-butoxyethylpyridylporphyrin, combines superb potency and Tipophilicity with low toxicity" Free Radical Biology and Medicine, 52(9): 1828-1834 (2012).
Rajic, Z et al. "Challenges encountered during development of Mn porphyrin-based, potent redox-active drug and superoxide dismutase mimic, MnTnBuOE-2-PyP5+, and its alkoxyalkyl analogues" Journal of Inorganic Biochemistry, 169:50-60 (2017).
Ramachandran, P. V. "Welcome to 'fluorine in medicinal chemistry'" Future Medicinal Chemistry, 1(5):771-772 (2009).
Reboupas, J. S et al. "Redox modulation of oxidative stress by Mn porphyrin-based therapeutics: the effect of charge distribution" Dalton Transactions 9:1233-1242 (2008).
Reboupas, J. S et al. "Impact of electrostatics in redox modulation of oxidative stress by Mn porphyrins: protection of SOD-deficient *Escherichia coli* via alternative mechanism where Mn porphyrin acts as a Mn carrier" Free Radical Biology and Medicine, 45:201-210 (2008).
Ross, A.D., et al., Hemodynamic effects of metalloporphyrin catalytic antioxidants: structure-activity relationships and species specificity. Free Radic Biol Med, 2002. 33(12): p. 1657-1669.
Russo G et al. "Radiation treatment breaks and ulcerative mucositis in head and neck cancer" The Oncologist, 13 (8):886-898, (2008).
Safford, S. E et al. "Suppression of Fibrosarcoma Metastasis by Elevated Expression of Manganese Superoxide Dismutase" Cancer Research, 54(16):4261-4265 (1994).
Santos et al. "Hydroxyl radical scavenger ameliorates cisplatin-induced nephrotoxicity by preventing oxidative stress, redox state unbalance, impairment of energetic metabolism and apoptosis in rat kidney mitochondria" Cancer Chemo Pharm, 61(1): 145-155 (2008).
Sato, T et al. "Treatment of Irradiated Mice with High-Dose Ascorbic Acid Reduced Lethality" PLoS One 10(2) e0117020 (2015).
Schmidt-Ullrich, Rupert K. "Molecular targets in radiation oncology" Oncogene, 22(37):5730-5733 (2003).
Schreck, R. et al. "Nuclear factor kappa B: an oxidative stress-responsive transcription factor of eukaryotic cells (a Yeview)" Free Radical Research Community, 17(4):221-237 (1992).
Semenza, G.L. "Oxygen sensing, homeostasis, and disease" New England Journal of Medicine, 365(6):537-547 (2011).
Shah, P et al. "The role of fluorine in medicinal chemistry" Journal of Enzyme Inhibition and Medicinal Chemistry, 22 (5):527-540 (2007).
Shappley, W. V et al. "Prospective Study of Determinants and Outcomes of Deferred Treatment or Watchful Waiting Among Men With Prostate Cancer in a Nationwide Cohort" Journal of Clinical Oncology, 27(30):4980-4985 (2009).
Shaw, E.G et al. "Phase II study of donepezil in irradiated brain tumor patients: effect on cognitive function, mood, and quality of life" Journal of Clinical Oncology, 24(9):1415-1420 (2006).
Sheng, H. et al. "Long-term neuroprotection from a potent redox-modulating metalloporphyrin in the rat" Free Radical Biol Med 47(7):917-923 (2009).
Sheng, H. et al. "Neuroprotective efficacy from a lipophilic redox-modulating Mn(III) N-Hexylpyridylporphyrin, WinTnHex-2-PyP: rodent models of ischemic stroke and subarachnoid hemorrhage" J of Pharmacol and Experimental Therapeutics, 338(3):906-916 (2011).
Sheng, H., et al. "Effects of metalloporphyrin catalytic antioxidants in experimental brain ischemia" Free Radical Biology & Medicine, 33(7):947-961 (2002).
Siglin, J. et al. "Time of decline in sexual function after external beam radiotherapy for prostate cancer" International Journal of Radiation, Oncology, Biology, Physics, 76(1):31-35 (2010).
Singer, P. A et al. "Sex or survival: trade-offs between quality and quantity of life" Journal Clinical Oncology, 9(2):328-334 (1991) (Abstract).
Sklavos, M. M. et al. "Redox modulation inhibits CD8 T cell effector function" Free Radical Biology & Medicine, 45 (10):1477-1486 (2008).
Sklavos, M. M et al. "Redox modulation protects islets from transplant-related injury" Diabetes, 59(7):1731-1738 K2010).

(56) References Cited

OTHER PUBLICATIONS

Sonveaux, P et al. "Targeting lactate-fueled respiration selectively kills hypoxic tumor cells in mice" The Journal of Clinical Investigation, 118(12):3930-3942 (2008).

Sorokina L. V. et al. "The evaluation of prooxidant and antioxidant state of two variants of lewis lung carcinoma: a comparative study" Experimental Oncology, 32(4):249-253 (2010).

Spasojevic, I et al. "Bioavailability of metalloporphyrin-based SOD mimics is greatly influenced by a single charge Yesiding on a Mn site" Free Radical Research, 45(2):188-200 (2011).

Spasojevic, I et al. "Electrostatic Contribution in the Catalysis of O Dismutation by Superoxide Dismutase Mimics WinlllTE-2-PyP5+ VERSUSMnlllBr8T-2-PyP+" Journal of Biological Chemistry, 278(9):6831-6837 (2003).

Spasojevic, I. et al. "Manganese(III) Biliverdin IX Dimethyl Ester: A Powerful Catalytic Scavenger of Superoxide Employing the Mn(III)/Mn(IV) Redox Couple" Inorg. Chern., 40:726-739 (2001).

Spasojevic, I. et al. "Manganese(III) Complexes with Porphyrins and Related Compounds as Catalytic Scavengers of Superoxide" Inorganic Chimica Acta, 317(1-2):230-242 (2002).

Spasojevic, I et al. "Mini Test Dose of Intravenous Busulfan (Busulfex®) in Allogeneic Non-Myeloablative Stem Cell Transplantation, Followed by Liquid Chromatography Tandem-Mass Spectrometry" Cancer Investigation, 30 (9):679-682 (2012).

Spasojevic, I et al. "Mn porphyrin-based superoxide dismutase (SOD) mimic, MnlllTE-2-PyP5+, targets mouse heart mitochondria" Free Radical Biology and Medicine, 42(8):1193-1200 (2007).

Spasojevic, I et al. "Pharmacokinetics of the potent redox modulating manganese porphyrin, MnTE-2-PyP5+ in plasma and major organs of B6C3F1 mice" Free Radical Biology and Medicine, 45(7):943-949 (2008).

Spasojevic, I et al. "Rotational Isomers of Nalkylpyridylporphyrins and their Metal Complexes. HPLC Separation, 1H NMR and X-ray Structural Characterization, Electrochemistry and Catalysis of O2.-Disproportionation" Inorgan Chern, 41(22):5874-5881 (2002).

Spasojevic, I., et al. "Nitrosylation of Manganese(II)tetrakis(Nethylpyridinium-2-yl)porphyrin: A Simple and Sensitive Spectrophotometric Assay for Nitric Oxide" Nitric Oxide: Biology and Chemistry, 4(5):526-533 (2000).

St Clair, D. K. et al. "Suppression of radiation-induced neoplastic transformation by overexpression of mitochondrial superoxide dismutase" Molecular Carcinogenesis, 6(4):238-242 (1992).

Stone H.B., et al. "Models for evaluating agents intended for the prophylaxis, mitigation and treatment of radiation injuries" Report of an NCI Workshop, Dec. 3-4, 2003. Radiat Research, 162(6):711-728 (2004).

Stover et al. "Topically applied manganese-porphyrins BMX-001 and BMX-010 display a significant anti-inflammatory response in a mouse model of allergic dermatitis" Archives of Dermatological Research, 308:711-721 (2016).

Stupp, R., et al. "Radiotherapy plus concomitant and adjuvant temozolomide for glioblastoma" New England Journal of Medicine, 352(10):987-996 (2005).

Sun, Y. et al. "A NADPH Oxidase-Dependent Redox Signaling Pathway Mediates the Selective Radiosensitization Effect of Parthenolide in Prostate Cancer Cells" Cancer Research, 70(7):2880-2890 (2010).

Symon, Z. et al. "A Murine Model for the Study of Molecular Pathogenesis of Radiation Proctitis" International Journal of Radiation, Oncology, Biology, Physics, 76(1):242-250 (2010).

Takahashi, I., et al. "Clinical study of the radioprotective effects of Amifostine (YM-08310, WR-2721) on chronic radiation injury" International Journal of Radiation Oncology, Biology, Physics, 12(6):935-938 (1986).

Tannehill, S.P. et al. "Amifostine and radiation therapy: past, present, and future" Seminars in Oncology, 23(4 Suppl 8):69-77 (1996) ABSTRACT.

Thomsen, Simon Francis "Atopic dermatitis: natural history, diagnosis, and treatment" ISRN Allergy, 354250. PMC4004110. (2014).

Tovmasyan et al. "Design, Mechanism of Action, Bioavailability and Therapeutic Effects of Mn Porphyrin-Based Redox Modulators" Medical Principles and Practice, 22(2): 103-130 (2013).

Tovmasyan, A. et al. "A comprehensive evaluation of catalase-like activity of different classes of redox-active therapeutics" Free Radical Biology and Medicine, 86:308-321 (2015).

Tovmasyan, A. et al. "Anticancer therapeutic potential of Mn porphyrin/ascorbate system" Free Radical Biology and Medicine, 89:1231-1247 (2015).

Tovmasyan, A. et al. "Differential Coordination Demands in Fe versus Mn Water-Soluble Cationic Metalloporphyrins Translate into Remarkably Different Aqueous Redox Chemistry and Biology" Inorganic Chemistry, 52(10):5677-5691 (2013).

Tovmasyan, A. et al. "Methoxy-derivatization of alkyl chains increases the in vivo efficacy of cationic Mn porphyrins. Synthesis, characterization, SOD-like activity, and SOD-deficient E. coll study of meta Mn(III) N-methoxyalkylpyridylporphyrins" Dalton Transactions, 40:4111-4121 (2011).

Tovmasyan, A et al. "Mn porphyrin-based SOD mimic and vitamin C enhance radiation-induced tumor growth inhibition" Free Radical Biology and Medicine, 87(S97) (2015).

Tovmasyan, A. et al. "Novel fluorinated Mn porphyrin as powerful SOD mimic and catalyst for ascorbate-coupled anticancer therapy" Free Radical Biology and Medicine, 112(S1):36-37 (2017).

Tovmasyan, A. et al. "Protection of rat prostate and erectile function from radiation-induced damage by novel Mn(lll) N-substituted pyridylporphyrin and ascorbate" Free Radical Biology and Medicine, 112:35-36 (2017).

Tovmasyan, A. et al. "PSS307—We have come a long way with Mn porphyrins: from superoxide dismutation to H2O2-driven pathways" Free Radical Biology and Medicine, 65:S133 (2013).

Tovmasyan, A. et al. "Rational Design of Superoxide Dismutase (SOD) Mimics: The Evaluation of the Therapeutic Potential of New Cationic Mn Porphyrins with Linear and Cyclic Substituents" Inorganic Chemistry, 53:11467-11483 (2014).

Tovmasyan, A. et al. "Simple Biological Systems for Assessing the Activity of Superoxide Dismutase Mimics" Antioxidants & Redox Signaling, 20(15):2416-2436 (2014).

Trzaska, Stephen "Cisplatin" Chemical and Engineering News, 83(25) (2005).

Tse H. M. et al. "Mechanistic analysis of the immunomodulatory effects of a catalytic antioxidant on antigen-presenting cells: implication for their use in targeting oxidation-reduction reactions in innate immunity" Free Rad Biol & Med, 36 (2):233-247(2004).

Umemoto et al. "Synthesis of 2,2,2-Trifluoroethylated Onium Salts of Nitrogen, Sulfur, and Phosphorus with (2,2,2-Trifluoroethyl)phenyliodonium Triflate" Bulletin of the Chemical Society of Japan, 64(6):2008-2010 (1991).

Umemoto et al. "Synthesis, Properties, and Reactivity of (1H,1H-Perfluoroalkyl)- and (1H-Perfluoro-1-alkenyl) aryliodonium Tritiates and Their Analogs" Bulletin of the Chemical Society of Japan, 60(9):3307-3313 (1987).

Umemoto et al., "1,1-dihydroperfluoroalkylations of nucleophiles with (1,1-dihydroperfluoroalkyl)phenyliodonium tritiates" Journal of Fluorine Chemistry, 31(2):231-236 (1986).

Urano M. et al. "Expression of manganese superoxide dismutase reduces tumor control radiation dose: Gene-Radiotherapy" Cancer Research, 55:2490-2493 (1995).

Van Luijk P. et al. "Sparing the region of the salivary gland containing stem cells preserves saliva production after radiotherapy for head and neck cancer" Science Translational Medicine, 7(305):305ra147 (2005).

Vissink, A. et al. "Oral sequelae of head and neck radiotherapy" Critical Reviews in Oral Biology & Medicine, 14 (3):199-212 (2003).

Wagner et al. "Biohalogenation: Nature's Way to Synthesize Halogenated Metabolites" Journal of Natural Products, 72:540-553 (2009).

Wasserman et al. "Influence of intravenous amifostine on xerostomia, tumor control, and survival after radiotherapy for head-and-neck cancer: 2-year follow-up of a prospective, randomized, phase III trial" Int J Rad Oncol Biol Phys, 63 (4):985-990 (2005).

(56) References Cited

OTHER PUBLICATIONS

Weitner et al. "Comprehensive pharmacokinetic studies and oral bioavailability of two Mn porphyrin-based SOD mimics, MnTE-2-PyP5+ and MnTnHex-2-PyP5+" Free Radical Biology and Medicine, 58:73-80 (2013).
Weitzel D. H. et al. "Neurobehavioral radiation mitigation to standard brain cancer therapy regimens by Mn(III) n-butoxyethylpyridylporphyrin-based redox modifier" Environmental Molecular Mutagenesis, 57(5):372-381 (2016).
Welsh, J. J. et al. "Ascorbate is a radiosensitizer in pancreatic cancer" Free Radical Biology and Medicine, 53:S52 (2012).
Windsor R. E. et al. "Germline genetic polymorphisms may influence chemotherapy response and disease outcome in osteosarcoma: A pilot study" Cancer, 118(7): 1856-1867 (2012).
Wong, A. L et al. "Tie2 expression and phosphorylation in angiogenic and quiescent adult tissues" Circulation Research, 81(4):567-574 (1997).
Xu, Y. et al. "KEAP1 Is a Redox Sensitive Target That Arbitrates the Opposing Radiosensitive Effects of Parthenolide in Normal and Cancer Cells" Cancer Research, 73(14):4406-4417 (2013).
Xu, Y. et al. "RelB Enhances Prostate Cancer Growth: Implications for the Role of the Nuclear Factor-kB Alternative Pathway in Tumorigenicity" Cancer Research, 69(8):3267-3271 (2009).
Yang, W. et al. "Redox regulation of cancer metastasis: molecular signaling and therapeutic opportunities" Drug Development Research, 75(5):331-341 (2014).
Yao, P. et al. "Quercetin protects human hepatocytes from ethanol-derived oxidative stress by inducing heme oxygenase-1 via the MAPK/Nrf2 pathways" Journal of Hepatology, 47(2):253-261 (2007).
Ye, X. et al. "Cytotoxic effects of Mn(III) N-alkylpyridylporphyrins in the presence of cellular reductant, ascorbate" Free Radical Research, 45(11-12): 1289-1306 (2011).
Yen, H. C. et al. "The protective role of manganese superoxide dismutase against adriamycin-induced acute cardiac toxicity in transgenic mice" The Journal of Clinical Investigation, 98(5):1253-1260 (1996).
Yulyana, Y. et al. "Redox-Active Mn Porphyrin-based Potent SOD Mimic, MnTnBuOE-2-PyP5+, Enhances Carbenoxolone-Mediated TRAIL-Induced Apoptosis in Glioblastoma Multiforme" Stem Cell Reviews and Reports, 12:140-155(2016).
Zagar, T. M. et al. "Two phase I dose-escalation/pharmacokinetics studies of low temperature liposomal doxorubicin KLTLD) and mild local hyperthermia in heavily pretreated patients with local regionally recurrent breast cancer" Int J Hyper, 30:285-94(2014).
Zeidan Y. H. et al. "Botulinum Toxin Confers Radioprotection in Murine Salivary Glands" International Journal of Radiation Oncology, Biology, Physics, 94(5):1190-1197 (2016).
Zhao, Y. et al. "Manganese superoxide dismutase deficiency enhances cell turnover via tumor promoter-induced alteration in AP-1 and p53-mediated pathways in a skin cancer model" Oncogene, 21(24):3836-3846 (2002).
Zhao, Y. et al. "Overexpression of manganese superoxide dismutase suppresses tumor formation by modulation of activator protein-1 signaling in a multistage skin carcinogenesis model" Cancer Research, 61(16):6082-6088 (2001).
Zhao, Y. et al. "p53 Translocation to Mitochondria Precedes Its Nuclear Translocation and Targets Mitochondrial Oxidative Defense Protein-Manganese Superoxide Dismutase" Cancer Research, 65(9):3745-3750 (2005).
Zhao, Y. et al. "Redox Proteomic identification of HNE-bound mitochondrial proteins in cardiac tissues reveals a systemic effect on energy metabolism after Doxorubicin treatment" Free Radical Biology and Medicine, 72:55-65 (2014).
Zitka O. et al. "Redox status expressed as GSH:GSSG ratio as a marker for oxidative stress in paediatric tumour patients" Oncology Letters, 4(6):1247-1253 (2012).
Ashcraft, et al., "Novel Manganese-Porphyrin Superoxide Dismutase-Mimetic Widens the Therapeutic Margin in a Preclinical Head and Neck Cancer Model" International Journal of Radiation Oncology, 93(4)1892-900 (2015).
Weitzel, et al., "Radioprotection of the Brain White Matter by Mn(III) N-Butoxyethylpyridylporphyrin-Based Superoxide Dismutase Mimic MnTnBuOE-2-PyP5+" Molecular Cancer Therapeutics, 14:70-79 (2015).
Extended European Search Report corresponding to European Patent Application No. 18861582.7 (8 pages) (dated May 27, 2021).
Boss et al. "Potential for a novel manganese porphyrin compound as adjuvant canine lymphoma therapy" Cancer Chemotherapy and Pharmacology, 80(2):421-431 (2017).
International Search Report and the Written Opinion of the International Searching Authority corresponding to International Patent Application No. PCT/US2018/052826 (9 pages) (dated Nov. 26, 2018).
First Examination Report (FER) issued in corresponding India Patent Application No. 202047017445, dated Sep. 15, 2021.

Fig. 11, cont.
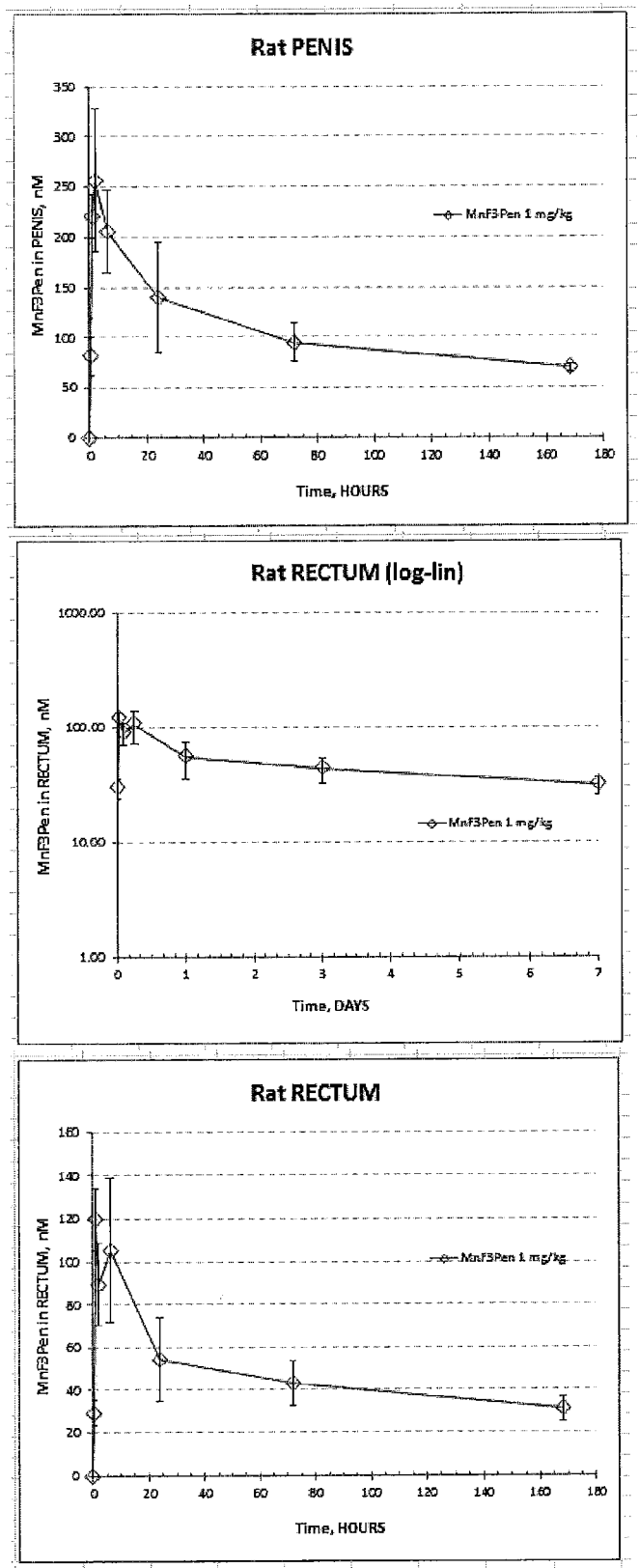

Fig. 11, cont.
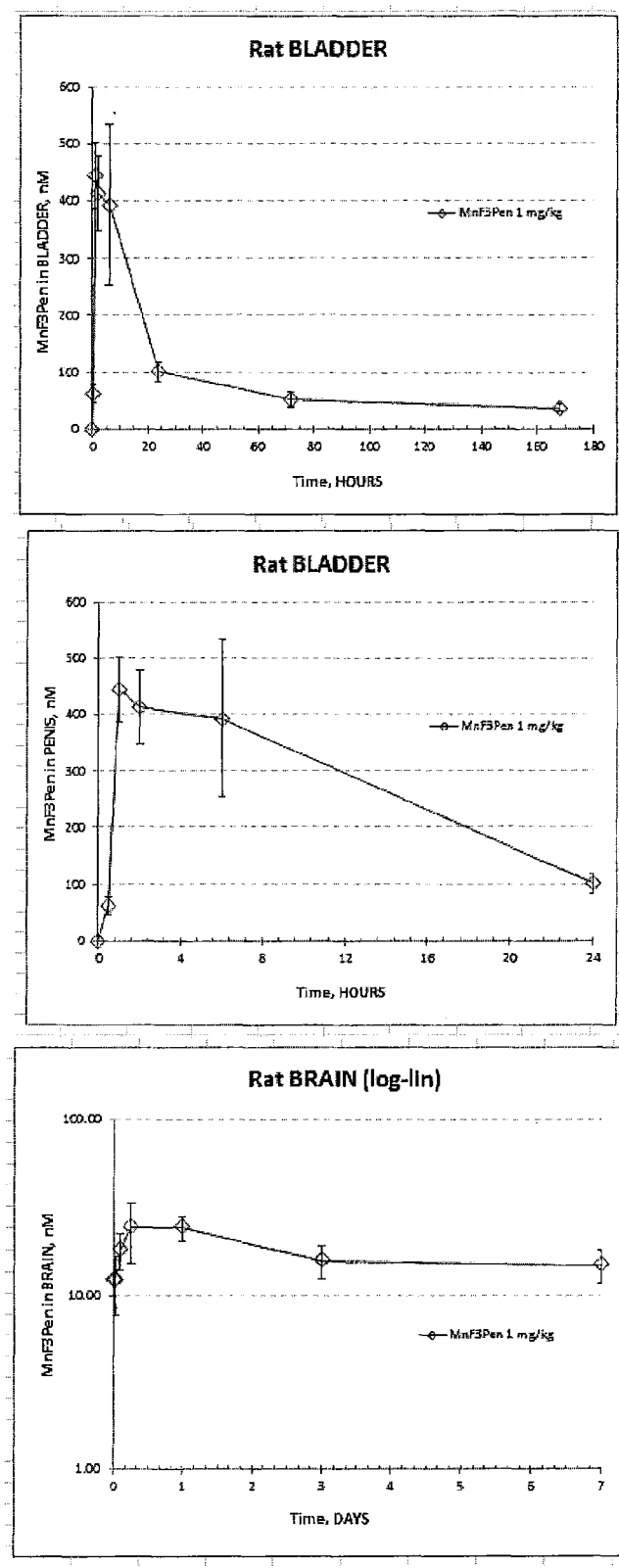

Fig. 11, cont.
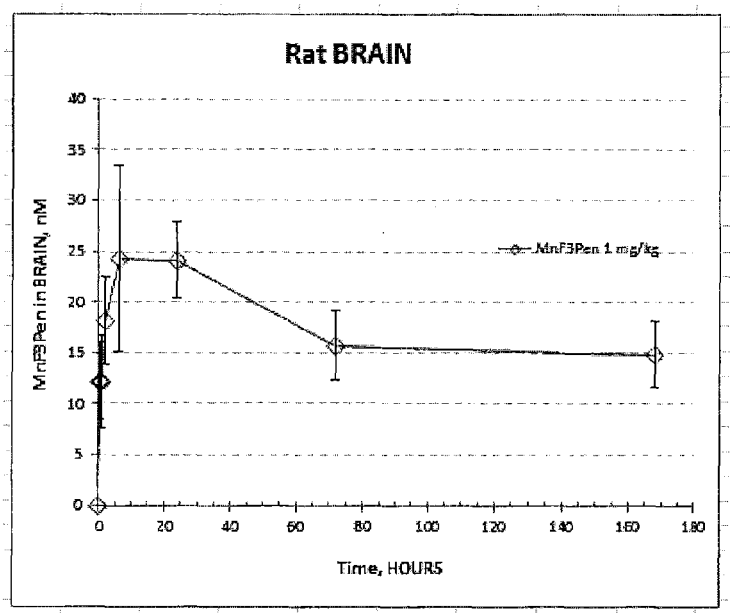
Fig. 12
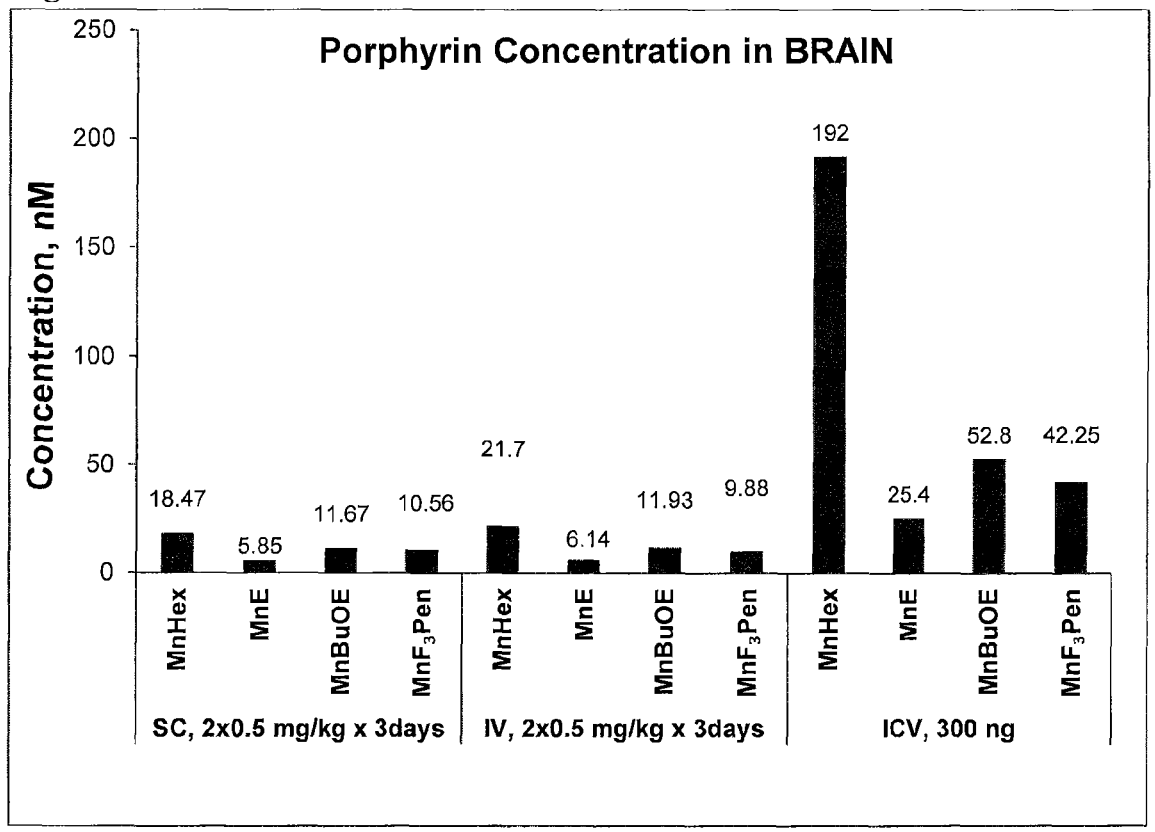

A Control

B - Mn4

Fig. 15, cont.
C – RT
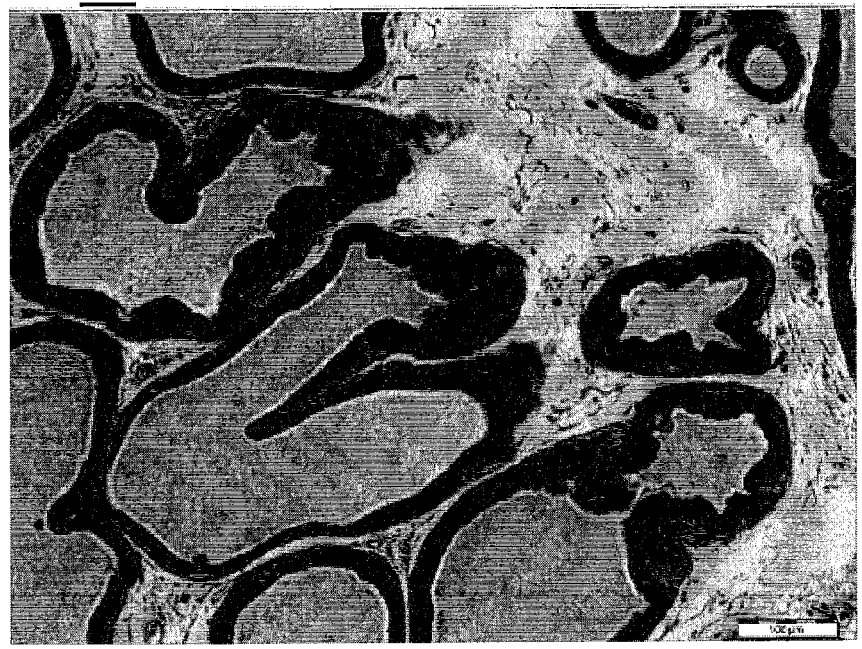
D – RT + Mn4

Fig. 15, cont.
E - RT + Mn4 + Asc
Fig.16
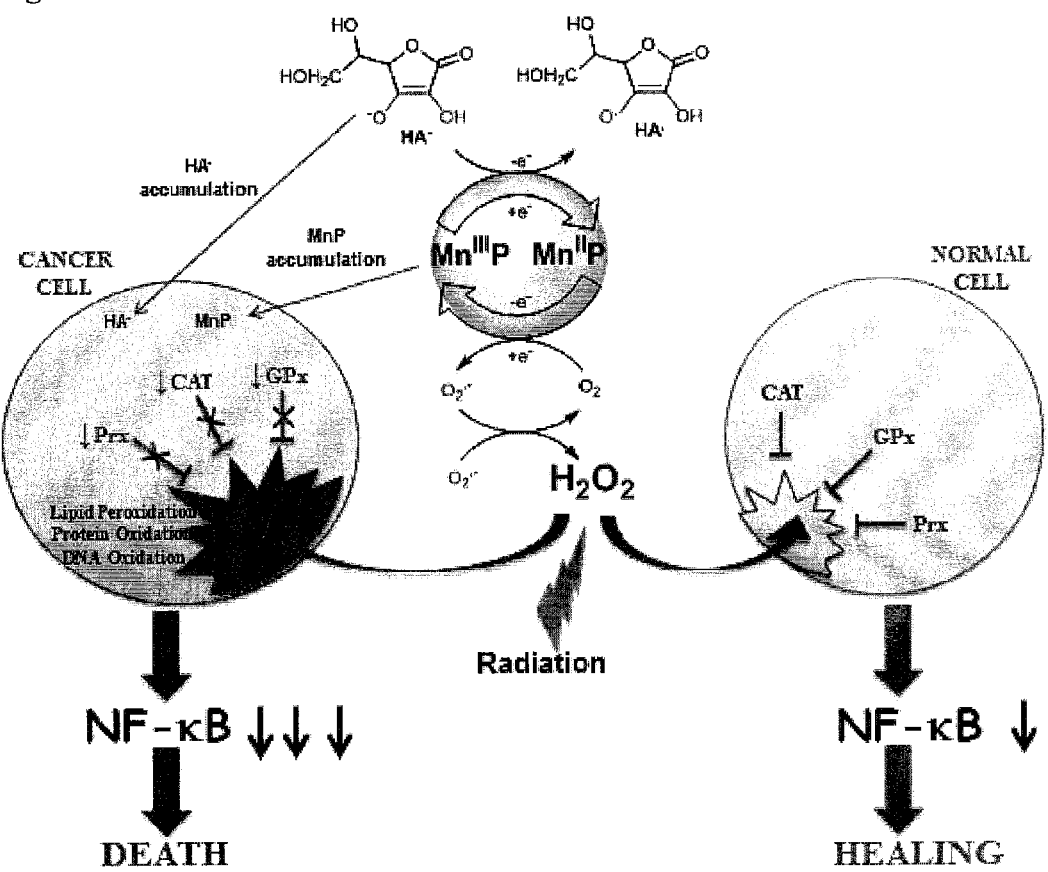

FLUORO SUBSTITUTED PORPHYRIN COMPOUNDS, PHARMACEUTICAL COMPOSITIONS COMPRISING THE SAME, AND METHODS OF PREPARING AND USING THE SAME

RELATED APPLICATION INFORMATION

This application claims the benefit of and priority to U.S. Provisional Patent Application Ser. No. 62/565,436, filed Sep. 29, 2017, the disclosure of which is incorporated herein by reference in its entirety.

STATEMENT OF GOVERNMENT SUPPORT

This invention was made with government support under grant number 5-P30-CA14236-29 awarded by the National Institutes of Health. The government has certain rights in this invention.

FIELD

The present invention concerns fluoro-substituted porphyrin compounds, methods of making the same, pharmaceutical formulations containing the same, and methods of use thereof.

BACKGROUND

The compound Mn(III) ortho N-butoxyethylpyridylporphyrin (Formula 001; sometimes abbreviated MnTnBuOE-2-PyP$^{5+}$) is known and described in Z. Rajic et al., *Free Radical Biology & Medicine* 53, 1828-1834 (2012).

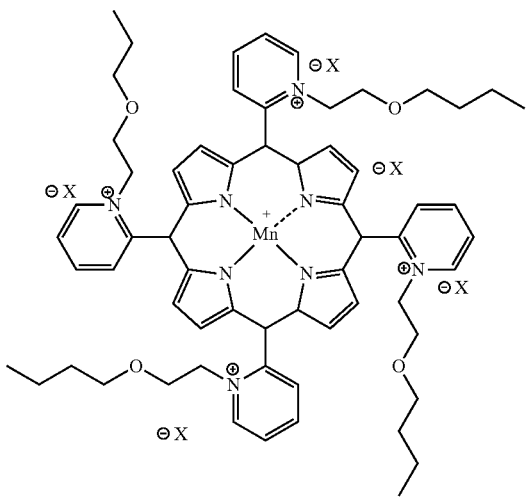

Formula 001

When X in Formula 001 is Cl$^-$, the compound may be abbreviated as Mn2 or MnBuOE. Thus, when Mn2 or MnBuOE is mentioned or referenced, it should be understood that Cl$^-$ is the anion for the compound.

This compound is described as having a variety of therapeutic activities, including treating inflammatory lung disease, neurodegenerative conditions, radiation injury, cancer, diabetes, cardiac conditions, and sickle cell disease. See generally Batinic-Haberle et al., U.S. Pat. No. 8,618,089.

International Application Publication No. WO 2010/080881 generally proposes that porphyrins may be substituted "with one or more fluorines" (see, for example, paragraphs and [0049] on page 9) therein. Fluorine is further mentioned along with numerous other options in connection with Table 1 and paragraph [0055] on pages 10-12 of WO 2010/080881. Prophetic examples of fluoro-porphyrins have been proposed in Examples 6, 7, and 8, as follows:

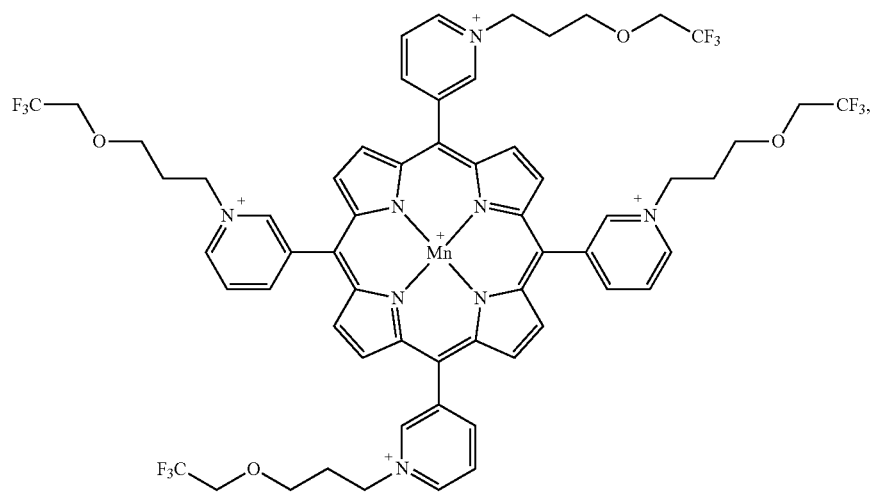

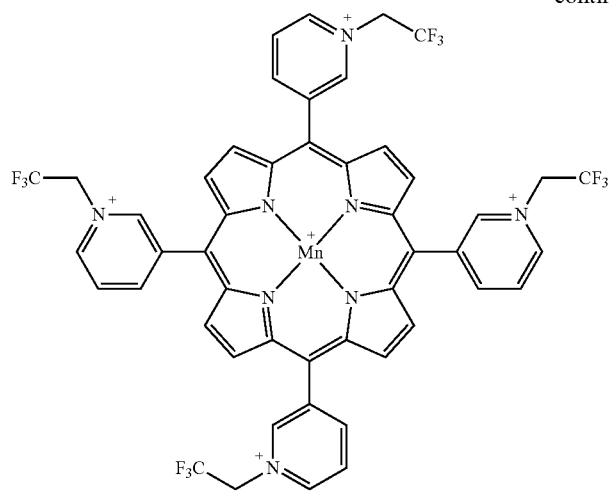

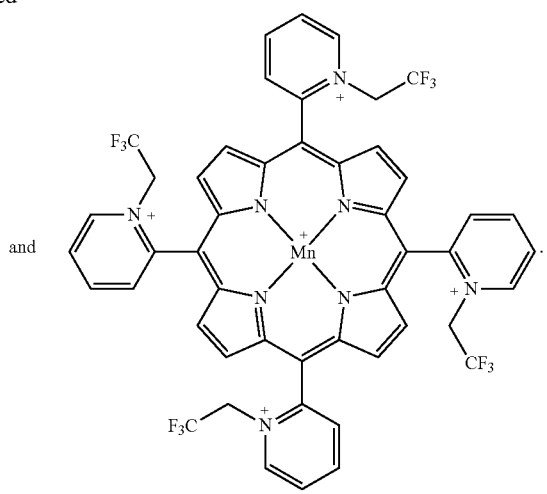

and

However, actual completion of a synthesis of the fluoro-porphyrins proposed in Examples 6, 7 and 8 of WO 2010/080881, or any fluoro-porphyrin compound for that matter, has never been demonstrated in the disclosure of the aforesaid application. Indeed, the preparation of selectively fluorinated compounds is widely known as a difficult and complicated matter. For example, Wagner, et al. (2009) 1 Nat. Prod. 72, 540-553 states in the abstract that "Chemical halogenation, however, often requires harsh reaction conditions and results in unwanted byproduct formation." Liang et al. (2013) *Angew. Chem. Int. Ed.* 52, 8214-8264 states on page 8215 that "Despite a longstanding appreciation of fluorine's utility, fluorination methods still lack generality, practicality, and predictability. Carbon-fluorine bond formation is a challenging chemical transformation largely due to the high electronegativity of fluorine and the high hydration energy of the fluoride anion." Amii et al. (2013) *Beilstein J. Org. Chem.* 9, 2793-2802 states on pages 2793-2794 that "synthesis of fluoro-organic compounds is still often faced with problems such as the difficulty in handling of fluorinating reagents and in controlling of chemical reactions. Furthermore, low stability of fluorine-containing intermediates and low selectivity (chemo, regio-, and/or stereo-) of the reactions have disturbed the progress of synthesis of fluorochemicals."

SUMMARY OF THE INVENTION

In an aspect of the invention, provided is a compound of Formula I:

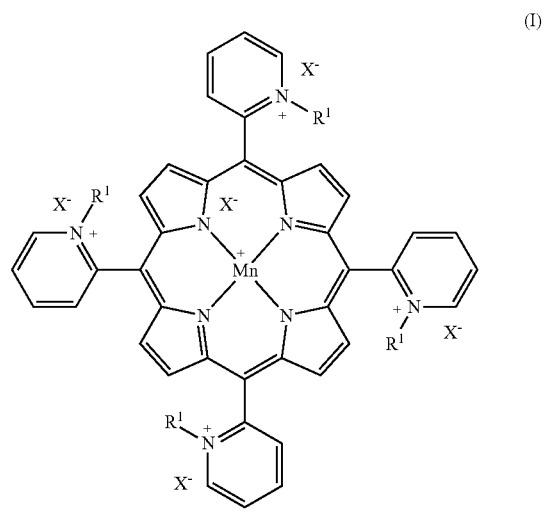

(I)

wherein: $R^1$ is a C1-C8 alkyl that is substituted with at least 1 fluorine (e.g., a C1-C8 alkyl substituted with 1-17 fluorine atoms); and X is an anion (e.g. $PF_6^-$ or $Cl^-$).

In an aspect of the invention, provided is a compound of Formula II (also referred to as $MnTFE-2-PyP^{5+}$ and MnFE):

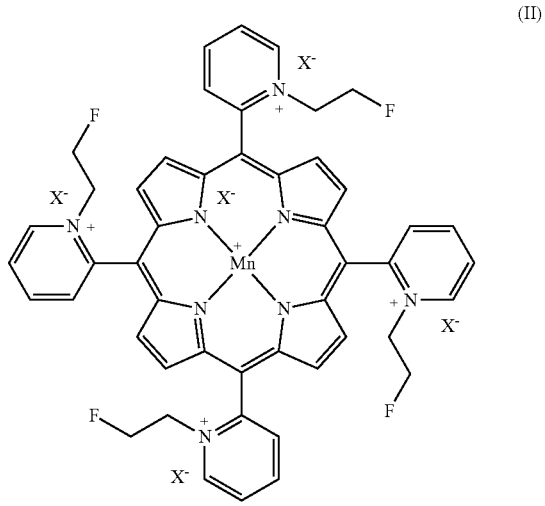

(II)

wherein X is an anion (e.g. PF$_6^-$ or Cl$^-$). When X is Cl$^-$ in the compound of Formula II, then the compound may be referred to as Mn3. Thus, when Mn3 is referenced or mentioned, it should be understood that Cl$^-$ is the anion for the compound.

In another aspect of the invention, provided is a compound of Formula III (also referred to as MnTF$_3$Pen-2-PyP$^{5+}$ and MnF$_3$Pen):

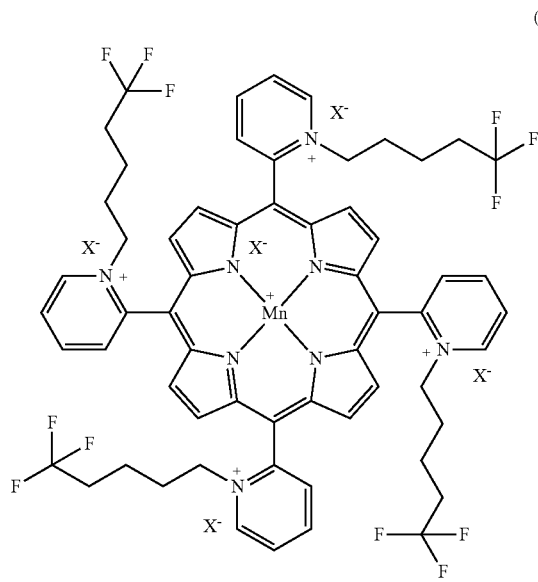

(III)

wherein X is an anion (e.g. PF$_6^-$ or Cl$^-$). When X is Cl$^-$ in the compound of Formula III, then the compound may be referred to as Mn4. Thus, when Mn4 is referenced or mentioned, it should be understood that Cl$^-$ is the anion for the compound.

In a further aspect of the invention, provided is a compound of Formula IV (also referred to as MnTF$_3$Pr-2-PyP$^{5+}$):

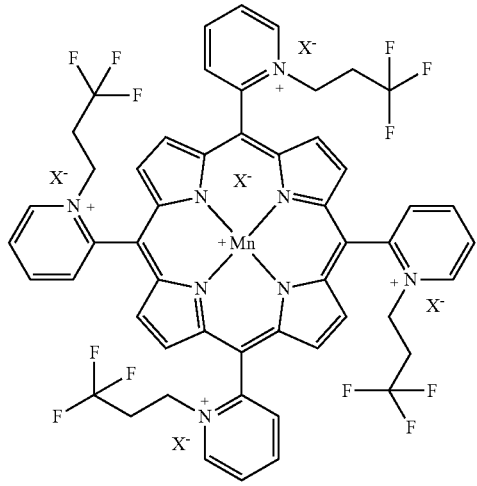

(IV)

wherein X is an anion (e.g. PF$_6^-$ or Cl$^-$).

In a further aspect of the invention, provided is a compound of Formula V (also referred to as MnTF$_3$Bu-2-PyP$^{5+}$):

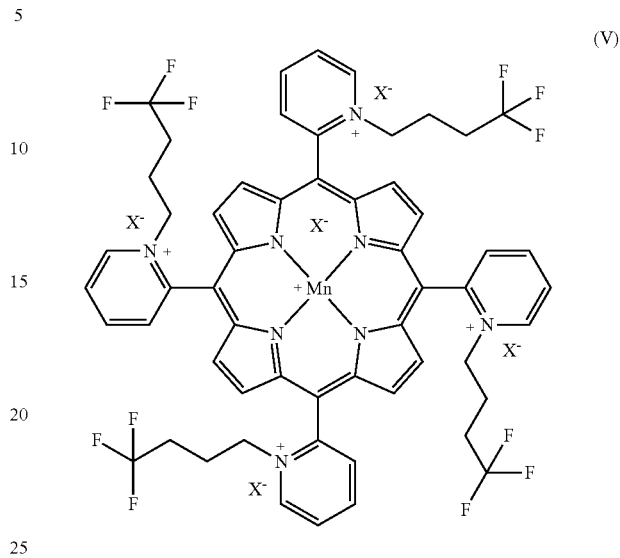

(V)

wherein X is an anion (e.g. PF$_6^-$ or Cl$^-$).

In a further aspect of the invention, provided is a compound of Formula VI (also referred to as MnTF$_5$Pen-2-PyP$^{5+}$):

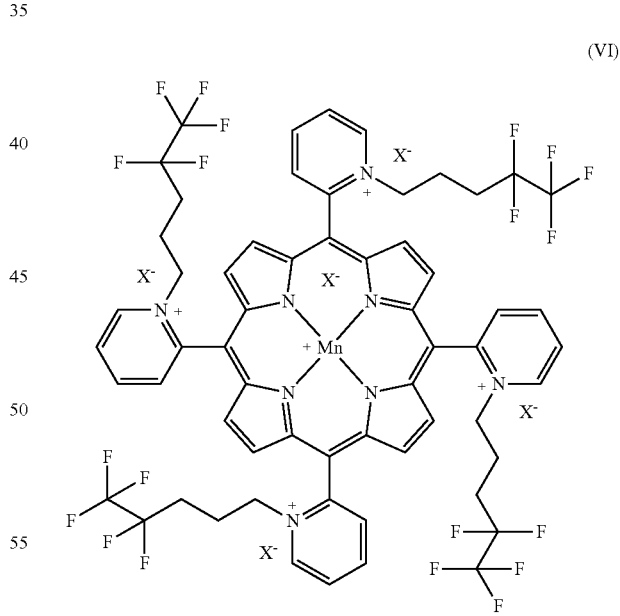

(VI)

wherein X is an anion (e.g. PF$_6^-$ or Cl$^-$).

In a further aspect of the invention, provided is a compound of Formula VII (also referred to as MnTF$_3$Hex-2-PyP$^{5+}$):

(VII)

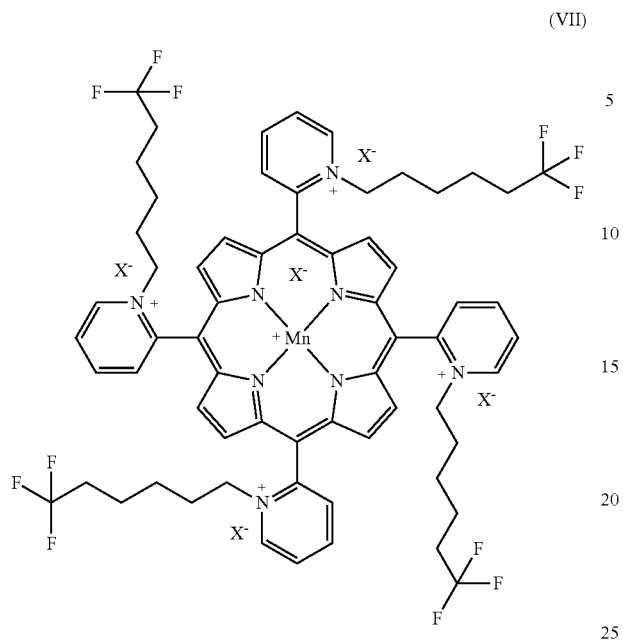

wherein X is an anion (e.g. $PF_6^-$ or $Cl^-$).

In a further aspect of the invention, provided is a compound of Formula VIII (also referred to as $MnTF_5Hex-2-PyP^{5+}$):

(VIII)

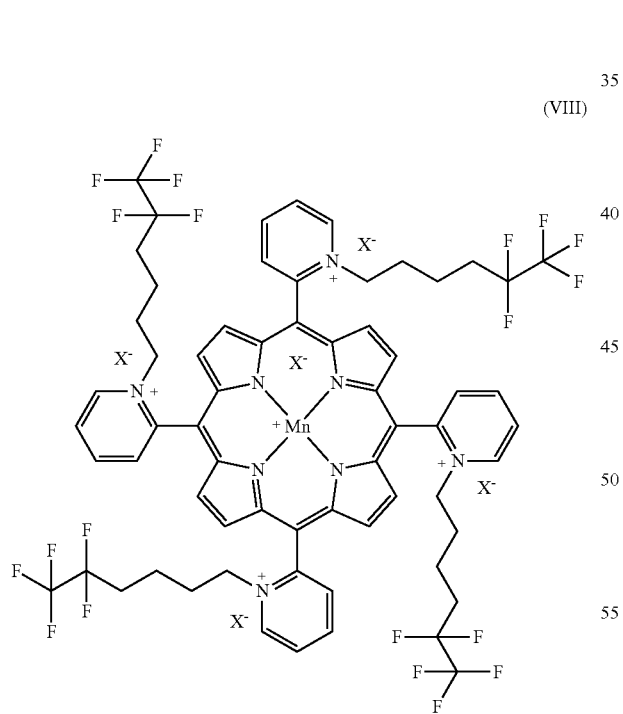

wherein X is an anion (e.g. $PF_6^-$ or $Cl^-$).

In a further aspect of the invention, provided is a compound of Formula IX (also referred to as $MnTF_7Hex-2-PyP^{5+}$):

(IX)

wherein X is an anion (e.g. $PF_6^-$ or $Cl^-$).

In a further aspect of the invention, provided is a compound of Formula X (also referred to as $MnTF_9Hex-2-PyP^{5+}$):

(X)

wherein X is an anion (e.g. $PF_6^-$ or $Cl^-$).

In another aspect of the invention, provided are compositions that comprise a compound of Formula I, Formula II, Formula III, Formula IV, Formula V, Formula VI, Formula VII, Formula VIII, Formula IX, or Formula X in a pharmaceutically acceptable carrier, wherein at least 90, 91, 92, 93, 94, 95, 96, 97, 98, or 99 percent by weight of all metalloporphyrins in said composition are the compound of Formula I, Formula II, Formula III, Formula IV, Formula V, Formula VI, Formula VII, Formula VIII, Formula IX, or Formula X.

In another aspect of the invention, provided are methods of inhibiting tumor growth in a subject that comprise administering a compound of Formula I, Formula II, Formula III, Formula IV, Formula V, Formula VI, Formula VII, Formula VIII, Formula IX, or Formula X. In some aspects, the method may include the administration of an additional agent and/or therapy, for example, the administration of ascorbate and/or the administration of radiation therapy and/or chemotherapy.

In another aspect of the invention, provided are methods of treating cancer in a subject that comprise administering a composition comprising a compound of Formula I, Formula II, Formula III, Formula. IV, Formula V, Formula VI, Formula VII, Formula VIII, Formula IX, or Formula X. In some aspects, the method may include the administration of an additional agent and/or therapy, for example, the administration of ascorbate and/or the administration of radiation therapy and/or chemotherapy.

A further aspect of the invention is directed to a method of treating and/or preventing one or more side effects associated with radiation and/or chemotherapy exposure in a subject during and/or following radiation and/or chemotherapy exposure, the method comprising administering to the subject prior to, during, and/or after radiation and/or chemotherapy exposure a compound of Formula I, Formula II, Formula III, Formula IV, Formula V, Formula VI, Formula VII, Formula VIII, Formula IX, or Formula X and optionally ascorbate.

Another aspect of the invention is directed to a method of suppressing in a subject an oxidative stress injury that may be independent of cancer, such as, but not limited to, a skin disorder, diabetes, a CNS injury, and/or a cardiac related disease.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the preferred embodiments that follow, such description being merely illustrative of the present invention.

BRIEF DESCRIPTION OF THE DRAWINGS

FIG. 12 Brain accumulation of different MnPs with different administration routes: MnTE-2-PyP$^{5+}$ (MnE, Mn1), MnTnHex-2-PyP$^{5+}$ (MnHex), MnTnBuOE-2-PyP$^{5+}$ (MnBuOE, Mn2), and MnTF$_3$Pen-2-PyP$^{5+}$ (MnF$_3$Pen, Mn4). MnF$_3$Pen accumulates in the brain at levels which are (route-dependently) up to 50% lower than those of MnBuOE due to its more polar fluorine atoms.

FIG. 16 is a schematic of the effects of cationic Mn(III) N-substituted pyridylporphyrins, MnPs, on tumor growth in the presence of H$_2$O$_2$ sources.

DETAILED DESCRIPTION OF EXAMPLE EMBODIMENTS

Figure 1:
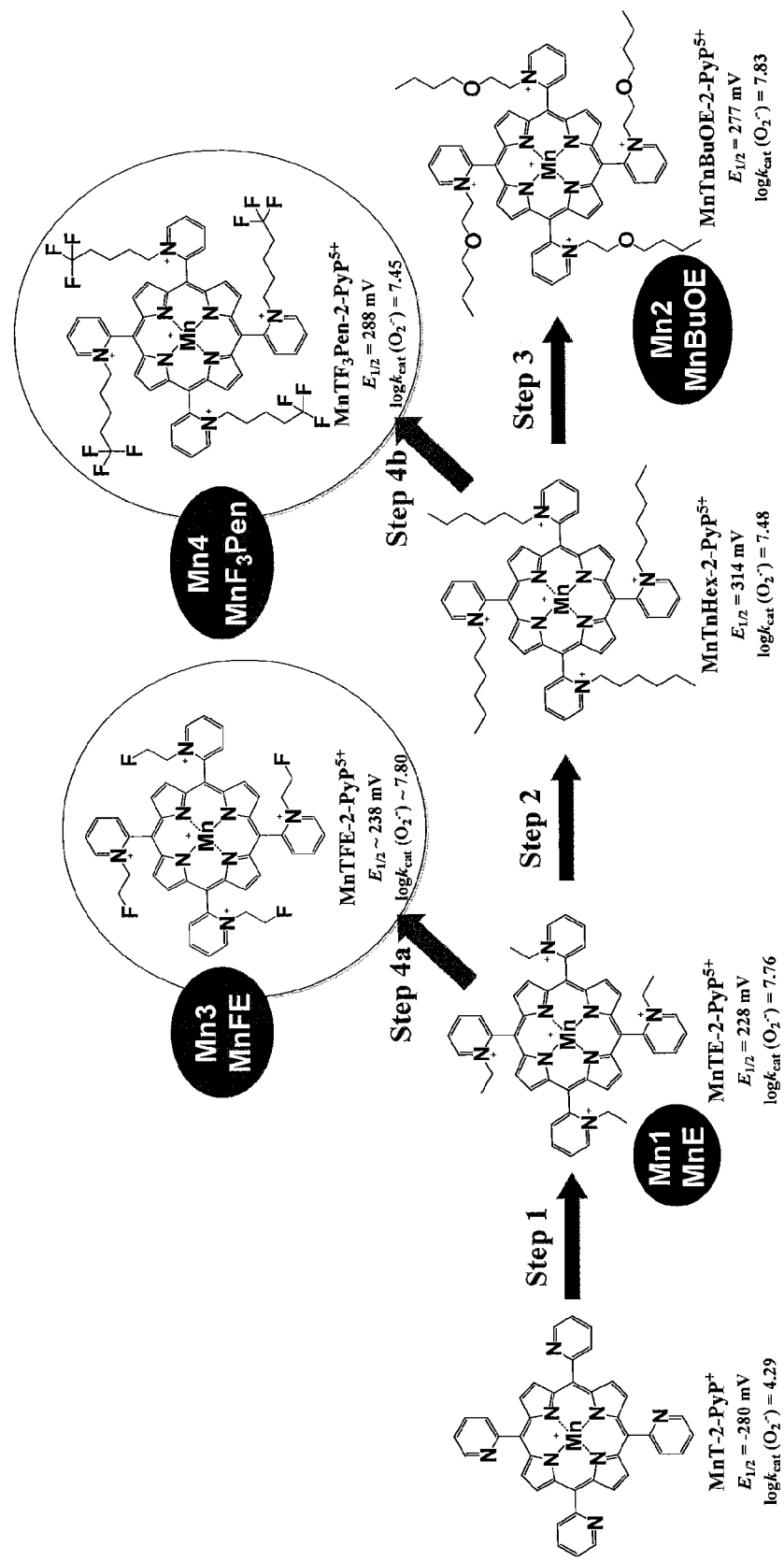
FIG. 1 Development of fluorinated and non-fluorinated Mn porphyrins. Alkyl, MnTE-2-PyP$^{5+}$ (Mn1 (which has as the anion) and is also referred to as MnE), MnTnHex-2-PyP$^{5+}$, and alkoxyalkyl MnTnBuOE-2-PyP$^{5+}$ (Mn2) are $1^{st}$, $2^{nd}$ and $3^{rd}$ generation compounds. New fluorinated (F) compounds of $4^{th}$ generation, MnTFE-2-PyP$^{5+}$ (Mn3) and MnTF$_3$Pen-2-PyP$^{5+}$ (Mn4), with improved properties have been developed. Redox properties ($E_{1/2}$, and log $k_{cat}(O_2.^-)$) indicate that they retain superior redox properties while they have improved bioavailability and safety/toxicity profiles.

The present invention is now described more fully hereinafter with reference to the accompanying drawings, in which embodiments of the invention are shown. This invention may, however, be embodied in many different forms and should not be construed as limited to the embodiments set forth herein; rather these embodiments are provided so that this disclosure will be thorough and complete and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

As used herein, the term "and/or" includes any and all possible combinations or one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, d 5%, ±1%, ±0.5%, or even ±0.1% of X. A range provided herein for a measureable value may include any other range and/or individual value therein.

As used herein, the terms "increase," "increases," "increased," "increasing", and similar terms indicate an elevation in the specified parameter or value of at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more.

As used herein, the terms "reduce," "reduces," "reduced," "reduction", "inhibit", and similar terms refer to a decrease in the specified parameter or value of at least about 5%, 10%, 15%, 20%, 25%, 30%, 35%, 40%, 45%, 50%, 55%, 60%, 65%, 70%, 75%, 80%, 85%, 90%, 95%, 97%, or 100%.

"Pharmaceutically acceptable" as used herein means that the compound, anion, or composition is suitable for administration to a subject to achieve the treatments described herein, without unduly deleterious side effects in light of the severity of the disease and necessity of the treatment.

"Alkyl" or "alkyl group," as used herein, means a straight-chain (i.e., unbranched), branched, or cyclic hydrocarbon chain that is completely saturated. In some embodiments, alkyl groups contain 1, 2, 3, 4, 5, 6, 7, 8, 9, 10, 11, 12, 13, 14, 15, 16, 17, 18, 19, or 20 carbon atoms (e.g., C1-4, C2-4, C3-4, C1-5, C2-5, C3-5, C1-6, C2-6, C3-6, C2-7, C1-8, C4-8, C4-20, C6-10, C6-20, C8-10, C8-20, etc.). In some embodiments, an alkyl groups contains 1-8 carbon atoms. In some embodiments, an alkyl groups contains 1-6 carbon atoms. In some embodiments, an alkyl groups contains 2-8 carbon atoms. In some embodiments, an alkyl groups contains 2-6 carbon atoms, and in some embodiments, an alkyl groups contains 1-4 carbon atoms. In some embodiments, the term "alkyl" or "alkyl group" means a straight-chain (i.e., unbranched) or branched hydrocarbon chain that is completely saturated. In certain embodiments, the term "alkyl" or "alkyl group" refers to a cycloalkyl group, also known as carbocycle. Non-limiting examples of example alkyl groups include methyl, ethyl, propyl, isopropyl, butyl, cyclopropyl and cyclohexyl.

Unless otherwise stated, structures depicted herein are meant to include all enantiomeric, diastereomeric, and geometric (or conformational) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

"Treat," "treating" or "treatment of" (and grammatical variations thereof) as used herein refer to any type of treatment that imparts a benefit to a subject and may mean that the severity of the subject's condition is reduced, at least partially improved or ameliorated and/or that some alleviation, mitigation or decrease in at least one clinical symptom (e.g., a symptom associated with a cancer and/or radiation and/or chemotherapy exposure) is achieved and/or there is a delay in the progression of the symptom. In some embodiments, the severity of a symptom associated with cancer and/or radiation and/or chemotherapy exposure may be reduced in a subject compared to the severity of the symptom in the absence of a method of the present invention.

In some embodiments, a fluoro-substituted porphyrin may be administered in a treatment effective amount. A "treatment effective" amount as used herein is an amount that is sufficient to treat (as defined herein) a subject. Those skilled in the art will appreciate that the therapeutic effects need not be complete or curative, as long as some benefit is provided to the subject. In some embodiments, a treatment effective amount may be achieved by administering a composition of the present invention.

The terms "prevent," "preventing" and "prevention" (and grammatical variations thereof) refer to avoidance, reduction and/or delay of the onset of a clinical symptom (e.g., a symptom associated with cancer and/or a radiation and/or chemotherapy exposure) and/or a reduction in the severity of the onset of the symptom relative to what would occur in the absence of a method of the present invention. The prevention can be complete, e.g., the total absence of the symptom. The prevention can also be partial, such that the occurrence of the symptom in the subject and/or the severity of onset is less than what would occur in the absence of a method of the present invention.

In some embodiments, a fluoro-substituted porphyrin may be administered in a prevention effective amount. A "prevention effective" amount as used herein is an amount that is sufficient to prevent (as defined herein) a clinical symptom (e.g., a symptom associated with cancer and/or a radiation and/or chemotherapy exposure) in a subject. Those skilled in the art will appreciate that the level of prevention need not be complete, as long as some benefit is provided to the subject. In some embodiments, a prevention effective amount may be achieved by administering a composition of the present invention.

The present invention finds use in both veterinary and medical applications. Subjects suitable to be treated with a method of the present invention include, but are not limited to, mammalian subjects. Mammals of the present invention include, but are not limited to, canines, felines, bovines, caprines, equines, ovines, porcines, rodents (e.g. rats and mice), lagomorphs, primates (e.g., simians and humans), non-human primates (e.g., monkeys, baboons, chimpanzees, gorillas), and the like, and mammals in utero. Any mammalian subject in need of being treated according to the present invention is suitable. Human subjects of both genders and at any stage of development (i.e., neonate, infant, juvenile, adolescent, adult) may be treated according to the present invention. In some embodiments of the present invention, the subject is a mammal and in certain embodiments the subject is a human. Human subjects include both males and females of all ages including fetal, neonatal, infant, juvenile, adolescent, adult, and geriatric subjects as well as pregnant subjects. In particular embodiments of the present invention, the subject is a human adolescent and/or adult.

A method of the present invention may also be carried out on animal subjects, particularly mammalian subjects such as mice, rats, dogs, cats, livestock and horses for veterinary purposes, and/or for drug screening and drug development purposes.

In some embodiments, the subject is "in need of" or "in need thereof" a method of the present invention, for example, the subject has findings typically associated with cancer, is suspected to have cancer, and/or the subject has cancer.

The fluoro-substituted porphyrins and compositions comprising fluoro-substituted porphyrins as described herein (e.g., a compound of Formula I, Formula II, Formula III, Formula IV, Formula V, Formula VI, Formula VII, Formula VIII, Formula IX, or Formula X) may be used for treating any of a variety of conditions in human and other mammalian subjects, including but not limited to treating inflammatory lung disease, neurodegenerative disease, radiation injury, cancer, diabetes, cardiac and cardiovascular conditions and injuries, sickle cell disease, etc. See generally Batinic-Haberle et al., U.S. Pat. No. 8,618,089.

Other conditions that may be treated by the fluoro-substituted porphyrins according to the present invention may include, but are not limited to, central nervous system injuries (such as Amyotrophic lateral sclerosis (ALS), Alzheimer's Disease, Multiple Sclerosis (MS), Parkinson's Disease, etc.), stroke, spinal cord injury, ischemia/reperfusion injuries, arthritis, auto-immune diseases, diabetes, morphine tolerance, drug dependence/addiction and inflammatory conditions.

In some embodiments, a fluoro-substituted porphyrin of the present invention may be used to treat and/or prevent one or more side effects associated with radiation and/or chemotherapy exposure in a subject during and/or following radiation and/or chemotherapy exposure. In some embodiments, methods of treating and/or preventing tissue damage in a subject during and/or following radiation and/or chemotherapy exposure are provided. A method of the present invention may comprise administering to the subject prior to, during, or after, radiation and/or chemotherapy exposure a fluoro-substituted porphyrin of the present invention, and optionally administering ascorbate (e.g., concurrently or sequentially). A method of the present invention may treat and/or prevent radiation-induced normal tissue injury in a subject. Radiation-induced normal tissue injury may be reduced in a subject by at least 5% or more compared to a conventional treatment and/or in the absence of a method of the present invention. "Normal tissue" as used herein refers to tissue that is noncancerous. The cells in "normal tissue" may be dividing at a normal rate. In some embodiments, the method may treat and/or prevent normal tissue injury due to and/or caused by inflammation. In some embodiments, a method of the present invention may treat and/or prevent radiation-induced erectile dysfunction in a subject.

In some embodiments, a fluoro-substituted porphyrin of the present invention has a structure represented by Formula I:

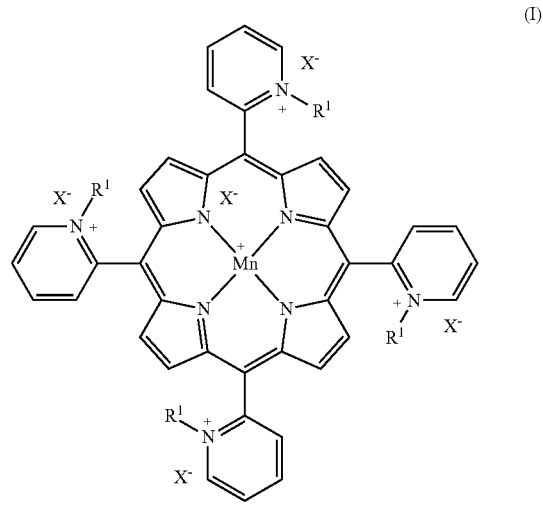

(I)

wherein:

$R^1$ is a C1-C8 alkyl that is substituted with at least 1 fluorine (e.g., a C1-C8 alkyl substituted with, e.g., 1, 2, 3, 4, 5, 6, 7, 8, 9, 10, 11, 12, 13, 14, 15, 16, or 17 fluorine atoms); and X is an anion (e.g. a halogen ion (e.g., chloride, etc.), $PF_6$, tosylate, besylate, and/or mesylate).

In some embodiments, $R^1$ is a C1, C2, C3, C4, C5, C6, C7, or C8 alkyl group that is substituted with 1 to Y fluorine atoms, where Y is determined by the number of carbon atoms in the alkyl group times 2 plus 1. Thus, when R' is a C2 alkyl group, then it may be substituted with 1, 2, 3, 4, or 5 fluorine atoms (e.g., 2×2=4+1=5).

In some embodiments, a fluoro-substituted porphyrin of the present invention has a structure represented by Formula II, Formula III, Formula IV, Formula V, Formula VI, Formula VII, Formula VIII, Formula IX, or Formula X:

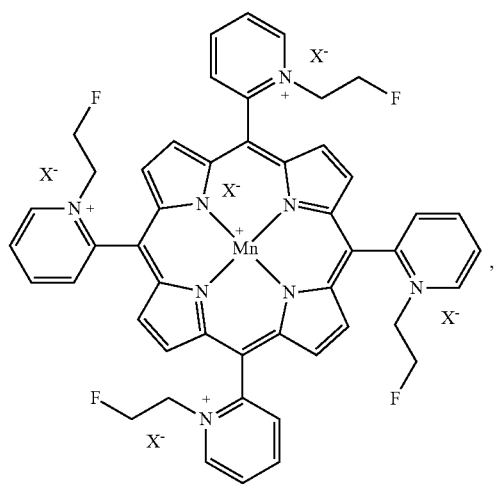
(II)
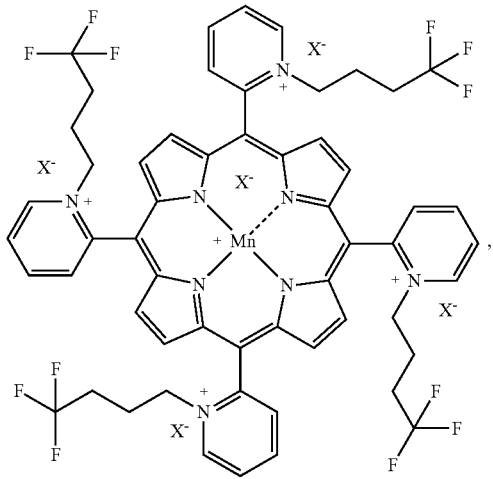
(V)
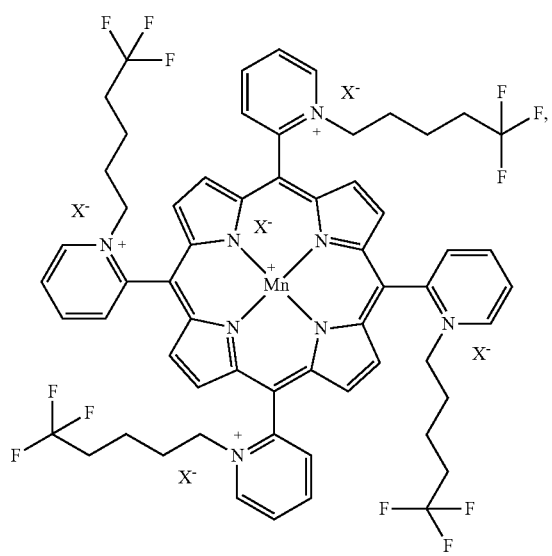
(III)
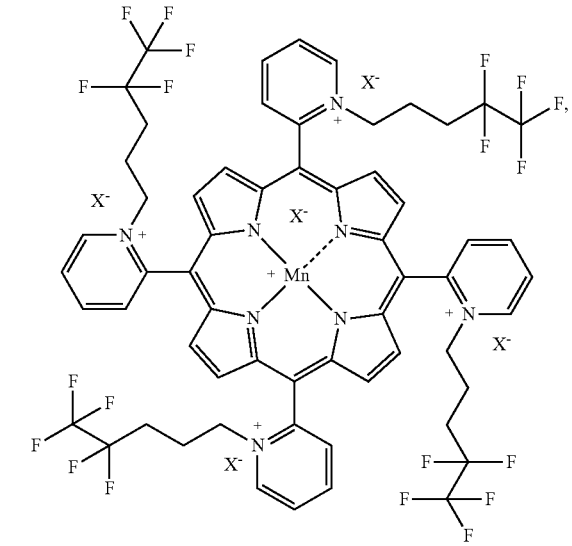
(VI)
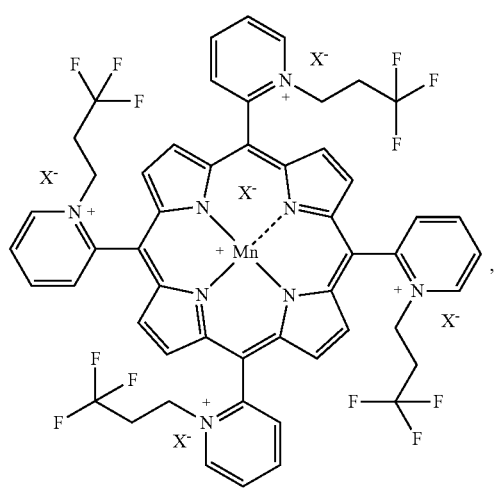
(IV)
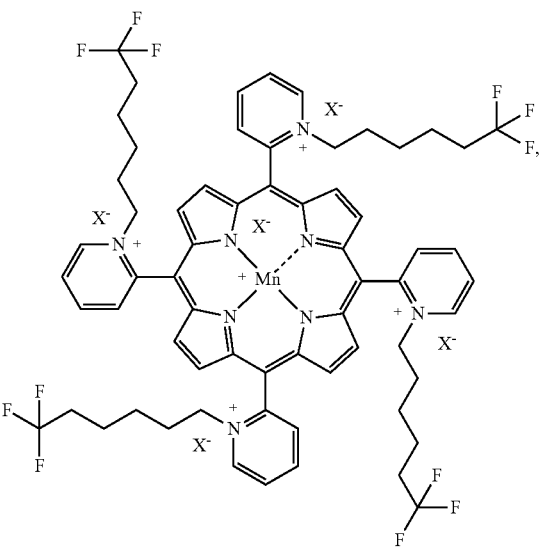
(VII)

-continued

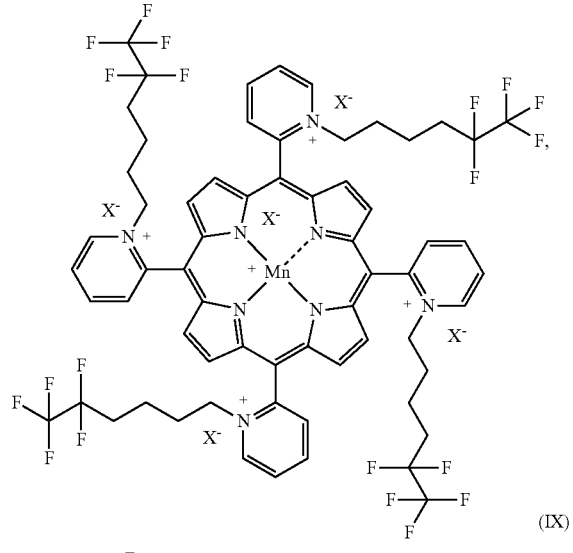

(VIII)

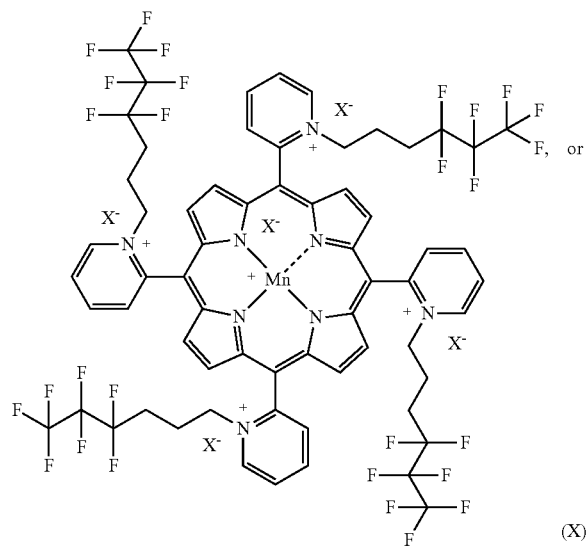

(IX)

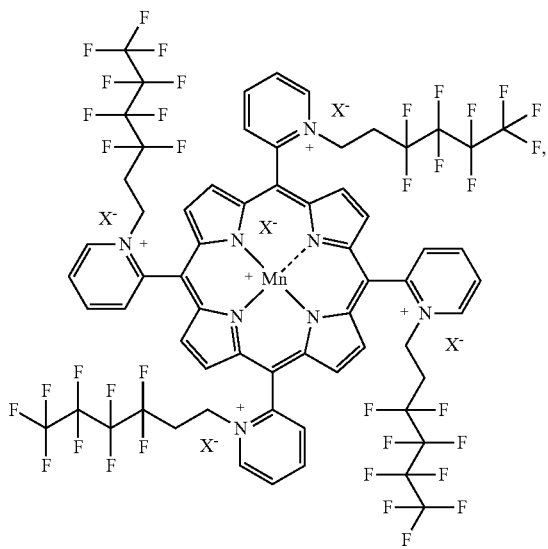

(X)

wherein X is an anion as described herein.

The fluoro-substituted porphyrins according to the present invention may have one or more fluorines. Without wishing to be bound by theory, the presence of fluoro groups may enhance drug transport and potency of the compounds and compositions of the present invention.

In some embodiments, the fluoro-substituted porphyrins have various active agents conjugated thereto. For example, anti-cancer agents, anti-inflammatory agents, analgesics (such as morphine), nitroxides, amino acids, peptides, peptidomimetics, antibodies, lipids or sugars may be conjugated to the fluoro-substituted porphyrins.

Further, the fluoro-substituted porphyrins of the present invention may be radiolabeled, for example with 18F. The radiolabeled compounds may then be used to determine biodistribution of the fluoro-substituted porphyrins, such as with Positron Emission Tomography (PET).

Compounds of the present invention may be obtained in the form of various salts or solvates. As the salts, pharmaceutically acceptable salts or salts available as raw materials are used. In addition, all stereoisomers, enantiomers and diastereomers are contemplated.

In some embodiments, the fluoro-substituted porphyrins of the present invention may have enhanced lipophilicity (e.g., compared to non-fluoro-substituted porphyrins). Lipophilicity can be measured via thin layer chromatography. The relative lipophilicity of a group of compounds can be determined in a given solvent system. Hydrophilic porphyrins will have a Retention Factor (Rf) of close to zero whereas the more lipophilic porphyrins have a larger Rf value. The fluoro-substituted porphyrins of the present invention suitably have a lipophilicity of greater than zero in a solvent system of acetonitrile:water:KNO$_3$ (saturated aqueous) (8:1:1). Alternatively, the lipophilicity may be quantified by the standard octanol/water partition coefficient (log P). In some embodiments, the lipophilic fluoro-substituted porphyrins may have a greater bioavailability than their hydrophilic analogs. In addition, the lipophilic fluoro-substituted porphyrins may have enhanced intracellular accumulation and/or intracellular uptake and/or potency in vivo as compared to hydrophilic analogs. Further, in other embodiments, the lipophilic fluoro-substituted porphyrins may selectively target different cellular compartments, such as the mitochrondria or the nucleus. Alternatively, other related cell/mitochrondia viability assays (e.g. MTT assay) may be used.

The fluoro-substituted porphyrins may be used to treat various conditions, including those resulting, at least in part, from oxidative stress injury (damage resulting from excessive levels of reactive oxygen and nitrogen species). In other embodiments, the fluoro-substituted porphyrins of the present invention may reduce oxidative stress. Porphyrins are effective functional catalytic antioxidants, modulators of redox-signaling pathways, potent radioprotectors, and anti-cancer agents. Again, without wishing to be bound by theory, it is thought that the antioxidant properties of porphyrins stem from their ability to regulate redox-active transcription factors via modulation of reactive oxygen and nitrogen species (ROS/RNS) and/or their ability to decrease biological damage by directly scavenging those species. Most recent evidence is somewhat changing how we view Mn porphyrins. Without wishing to be bound by theory, because of the biologically relevant redox chemistry of Mn porphyrins, which involves Mn in +2, +3, +4 and/or +5 oxidation states, they can not only undergo reduction reactions (i.e., classical antioxidative reactions) but can also undergo oxidation reactions as well. A biologically very relevant oxidation is the oxidation of cysteines of different proteins including those of transcription factors. Such oxidative modification of transcription factors, which may thereby affect their activation and in turn cellular proliferative and apoptotic processes.

In some embodiments, the fluoro-substituted porphyrins of the present invention provide improved (e.g., statistically significant increases) characteristics in the oxidation of ascorbate when compared with non-fluoro-substituted analogs. Important reactions that the Mn fluoro-substituted porphyrins may undergo in vivo include cellular reductants such as ascorbate and thiols. Reactions involving the cycling of Mn porphyrin with ascorbate leads to the production of cytotoxic hydrogen peroxide, which is subsequently used by the Mn porphyrin along with glutathione to catalyze the oxidation of cysteines of signaling proteins, thereby modifying their transcription. Direct cycling with thiols may also be possible. However, the direct removal of reactive species by Mn porphyrin cannot be excluded.

Pathological conditions that may be treated by the fluoro-substituted porphyrins according to the present invention include, but are not limited to, central nervous system injuries (such as Amyotrophic lateral sclerosis (ALS), Alzheimer's Disease, Multiple Sclerosis (MS), Parkinson's Disease, etc. etc.), stroke, spinal cord injury, cancer, ischemia/reperfusion injuries, cardiovascular injuries, arthritis, sickle cell disease, radiation injury, auto-immune diseases, diabetes, morphine tolerance, drug dependence/addiction and inflammatory conditions.

In some embodiments, fluoro-substituted porphyrins according to the present invention are suitable for use as anti-cancer agents in cancers such as, but not limited to, lung, breast, brain, skin, head and neck, prostate, pancreas, gastrointestinal, and colon. Without wishing to be bound by theory, it is thought that the anti-cancer activity of the fluoro-substituted porphyrins arises from the redox-based impact of the fluoro-substituted porphyrins on oxidative stress and thus on the NF-kB, Nrf2/Keap1, HIF/VEGF/NOS, MAPK (mitogen-activated protein kinases), phosphatase 2A, mitochondrial respiratory complexes I and III, and/or proteins of the glycolysis pathways. In some embodiments, the fluoro-substituted porphyrins suppress angiogenesis in tumors.

In some embodiments, the fluoro-substituted porphyrins may be potent adjuvants in radiation therapy, hyperthermia, chemotherapy and pain management, such as morphine tolerance reversal. In other embodiments, the fluoro-substituted porphyrin may be administered with one or more anti-cancer agents (e.g. Gleevac®, cisplatin, taxol, vincristine, paclitaxel, temozolomide, dexamethasone, doxorubicin, cyclophosphamide, statins, melphalan, fludarabine, camptotechins, monoclonal and polyclonal antibodies against VEG, VEGFr, EGF, ERGFr, ascorbate, etc.), anti-inflammatory agents (e.g. cyclooxygenaase inhibitors, NOS inhibitors, NADPH oxidase inhibitors, etc.), analgesics (e.g. morphine, codeine, aspirin, acetominaphen, ibuprofen, etc.) and/or therapies (e.g., radiation therapy, hyperthermia and pain management, such as morphine tolerance reversal). In some embodiments, the fluoro-substituted porphyrin may be administered with ascorbate. In some embodiments, the fluoro-substituted porphyrin may be administered with radiation therapy. In some embodiments, the fluoro-substituted porphyrin may be administered with chemotherapy. In some embodiments, the fluoro-substituted porphyrin may be administered with more than one other active agent and/or therapy, e.g., administered with ascorbate along with radiation and/or chemotherapy. Combinations with PD-L1/PD-1 inhibitors and those with natural compounds such as flavonoids may be used.

Radiation therapy may be of any suitable type, typically ionizing radiation therapy, and generally external beam radiation therapy. Such therapy may be in any suitable dose, such as from 10, 20, or 40 Gray to 60, 80, or 100 Gray, administered as a single dose or administered in a fractionated series of doses. Suitable types of ionizing radiation for use in carrying out the invention include photon radiation (e.g., x-ray and gamma ray radiation) and particle radiation (e.g., electron, proton, neutron, carbon ion, alpha particle, and beta particle radiation).

According to some embodiments of the present invention, the subject may be exposed to radiation, such as, e.g., the subject may receive a total dose of radiation of about 5 to about 100 Gy or about 30 to about 90 Gy. In some embodiments, the subject may be exposed to a total dose of radiation of about 5, 10, 15, 20, 25, 30, 35, 40, 45, 50, 55, 60, 65, 70, 75, 80, 85, 90, 95, 100, 125, 150 Gy or more. In some embodiments, the subject is receiving and/or may be administered radiation therapy. The radiation therapy may comprise at least one radiation treatment that is administered 5 days a week for 1 to 10 weeks. As one of ordinary skill in the art understands, radiation therapy may span a certain length of time (e.g., 1-10 weeks) and may not be administered to the subject continuously, but rather intermittently.

According to some embodiments of the present invention, the subject is receiving and/or may be administered chemotherapy. Example chemotherapies include, but are not limited to, cisplatin, temozolamide, tamoxifen, trastuzumab, fluorouracil (e.g., 5 fluorouracil (5FU)), mitomycin-C, and/or FOLFOX. The method and/or fluoro-substituted porphyrin may not interfere with tumor control and/or cancer treatment (e.g., chemotherapy). As one of ordinary skill in the art understands, chemotherapy may span a certain length of time (e.g., 1-10 weeks) and may not be administered to the subject continuously, but rather intermittently.

A synergistic effect may be seen when a fluoro-substituted porphyrin of the present invention is administered in combination with one or more anti-cancer agent(s) and/or therapies. In some embodiments, the fluoro-substituted porphyrin may be conjugated to an anti-cancer agent. In other embodiments, the fluoro-substituted porphyrin may not be conjugated to an anti-cancer agent. If a fluoro-substituted porphyrin conjugated to an anti-cancer agent is administered in combination with a second anti-cancer agent, the second anti-cancer agent may be the same or different as the conjugated anti-cancer agent.

In some embodiments, a method of the present invention comprises administering ascorbate to a subject. Ascorbate may be administered to the subject in an amount of about 0.1 mg/kg to about 5 g/kg, and in some embodiments, about 0.1 mg/kg to about 10 mg/kg or about 0.1 g/kg to about 2 g/kg. In some embodiments, ascorbate may be administered to the subject in an amount of about 0.1, 0.5, 1, 1.5, 2, 2.5, 3, 3.5, 4, 4.5, 5, 5.5, 6, 6.5, 7, 7.5, 8, 8.5, 9, 9.5, 10, 20, 30, 40, 50, 60, 70, 80, 90, 100, 200, 300, 400, 500, 600, 700, 800, 900, or 1000 mg/kg, or about 0.01, 0.5, 1, 1.5, 2, 2.5, 3, 3.5, 4, 4.5, or 5 g/kg. Ascorbate may be administered to the subject before, during, and/or after radiation and/or chemotherapy exposure and/or may be administered concurrently and/or sequentially with a fluoro-substituted porphyrin of the present invention.

In some embodiments, a fluoro-substituted porphyrin of the present invention and/or ascorbate may be administered to the subject at about 30 minutes to about 4 days prior to the subject being exposed to radiation and/or chemotherapy, such as, for example, about 1 hour to about 3 days, about 4 hours to about 2 days, or about 12 hours to about 48 hours prior to the subject being exposed to radiation and/or chemotherapy. In some embodiments, the fluoro-substituted porphyrin and/or ascorbate may be administered to the subject at about 30, 45, or 60 minutes, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 hours prior to the subject being exposed to radiation and/or chemotherapy.

In some embodiments, the fluoro-substituted porphyrin and/or ascorbate may be administered to the subject during radiation and/or chemotherapy exposure and/or at about 30 minutes to about 4 days after the subject is exposed to radiation and/or chemotherapy, such as, for example, about 1 hour to about 3 days, about 4 hours to about 2 days, or about 12 hours to about 48 hours after exposure to radiation and/or chemotherapy. In some embodiments, the fluoro-substituted porphyrin and/or ascorbate may be administered to the subject at about 30, 45, or 60 minutes, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 hours after exposure to radiation and/or chemotherapy.

A fluoro-substituted porphyrin and/or ascorbate may be administered to the subject one or more times per week (e.g., 1, 2, 3, 4, 5, or more times per week). In some embodiments, the fluoro-substituted porphyrin and/or ascorbate may be administered to the subject two or three times per week or every two or three days. In some embodiments, the fluoro-substituted porphyrin and/or ascorbate may be administered two or three times a week or every two or three days after an initial radiation and/or chemotherapy exposure (e.g., an initial radiation and/or chemotherapy treatment).

The fluoro-substituted porphyrin and/or ascorbate may be administered to the subject one or more times after an initial radiation and/or chemotherapy exposure (e.g., an initial radiation and/or chemotherapy treatment), such as, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more times. In some embodiments, the subject is receiving radiation therapy and/or chemotherapy and the fluoro-substituted porphyrin and/or ascorbate is administered throughout the course of the radiation therapy and/or chemotherapy, such as, for example, one or more times during the course of the radiation therapy and/or chemotherapy.

In some embodiments, the fluoro-substituted porphyrin and/or ascorbate may be administered one or more times after a final radiation and/or chemotherapy exposure (e.g., a final radiation and/or chemotherapy treatment), such as, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more times. In some embodiments, the subject has received a final radiation therapy and/or chemotherapy treatment and the fluoro-substituted porphyrin and/or ascorbate is administered one or more times following the final radiation therapy and/or chemotherapy treatment. In some embodiments, the fluoro-substituted porphyrin and/or ascorbate is administered two or three times a week or every two or three days for 1 to 8 weeks after a final radiation and/or chemotherapy exposure (e.g., a final radiation and/or chemotherapy treatment).

In some embodiments, a cell is contacted with an amount of a fluoro-substituted porphyrin effective to reduce oxidative stress. Suitably, the reduction in oxidative stress can be measured by measuring a reduction in the amount of reactive oxygen and/or nitrogen species or increase in oxidative modifications of biomolecules such as proteins, sugars, nucleic acids or lipids, The term "contacting a cell" is used to mean contacting a cell in vitro or in vivo (i.e. in a subject, such as a mammal, including humans, rabbits, cats and dogs). In some embodiments, the cell may be contacted as a result of administration of a fluoro-substituted porphyrin to a subject.

An effective amount of a fluoro-substituted porphyrin according to the present invention will vary with the particular condition being treated, the age and physical condition of the subject being treated, the severity of the condition, the duration of treatment, the nature of concurrent therapy, the route of administration, the particular pharmaceutically acceptable carrier utilized, and like factors within the knowledge and expertise of the attending physician. For example, an effective amount of the fluoro-substituted porphyrins of the present invention for systemic administration may be from about 0.01 mg/kg to about 100 mg/kg body weight, from about 0.1 mg/kg to about 100 mg/kg per body weight, from about 0.2 mg/kg to about 4 mg/kg; from about 0.2 mg/kg to about 2 mg/kg, and, in some embodiments, from about 1 mg/kg to about 50 mg/kg body weight per day. Transdermal dosages would be designed to attain similar serum or plasma levels, based upon techniques known to those skilled in the art of pharmacokinetics and transdermal formulations. Plasma levels for systemic administration are expected to be in the range of 0.001 to 100 microgram/mL, more preferably from 0.01 to 50 microgram/mL and most preferably from 0.1 to 10 microgram/mL. While these dosages are based upon a daily administration rate, the fluoro-substituted porphyrins of the present invention may also be administered at other intervals, such as twice per day, twice weekly, once weekly, or once a month. The fluoro-substituted porphyrins of the present invention may also be administered in a continuous mode, for example, using an osmotic pump. In one embodiment, the porphyrins may be initially administered more frequently (e.g. daily) at higher doses to establish a loading dose with continued administration at a lower less frequent dose. One of ordinary skill in the art would be able to calculate suitable effective amounts for other intervals of administration. For example, the efficacy of various fluoro-substituted porphyrins in vivo is affected by both the antioxidant potency of the fluoro-substituted porphyrin and the bioavailability of that fluoro-substituted porphyrin.

The additional active agent or agents and/or therapies can be administered simultaneously or sequentially with the fluoro-substituted porphyrins of the present invention. Sequential administration includes administration before or after the fluoro-substituted porphyrins of the present invention. In some embodiments, the additional active agent or agents and/or therapies can be administered in the same composition as the fluoro-substituted porphyrins of the present invention. In other embodiments, there can be an interval of time between administration of the additional active agent and/or therapies and the fluoro-substituted porphyrins of the present invention.

In some embodiments, the administration of an additional therapeutic agent (e.g., ascorbate) with a compound of the present invention will enable lower doses of the other therapeutic agents to be administered for a longer period of time. In some embodiments, administration of ascorbate may increase the radio- and/or chemosensitization of a tumor in a subject, which may allow for reduced radiation and/or chemotherapy dosing.

In some embodiments, the fluoro-substituted porphyrins are administered in a pharmaceutically acceptable composition, such as in or with a pharmaceutically acceptable carrier.

Compositions may include one or more of the isoforms of the fluoro-substituted porphyrins of the present invention. When racemates exists, each enantiomer or diastereomer may be separately used, or they may be combined in any proportion. Where tautomers exist all possible tautomers are specifically contemplated. Where atropisomers exist, each may be used separately, or may be combined in any proportion. In some embodiments, a single isoform or atropisomer may be used may comprise at least 90%, 91%, 92%, 93%, 94%, 95%, 96%, 97%, 98%, 99% or greater by weight of all of the fluoro-substituted porphyrin or metaloporyphyrin in the composition.

Pharmaceutical compositions for use in accordance with the present invention may be formulated in a conventional manner using one or more physiologically acceptable carriers or excipients. Thus, the fluoro-substituted porphyrins may be formulated for administration by, for example, solid dosing, eyedrop, in a topical oil-based formulation, injection, inhalation (either through the mouth or the nose), implants, or oral, buccal, parenteral or rectal administration. Techniques and formulations may generally be found in "Remington's Pharmaceutical Sciences," (Meade Publishing Co., Easton, Pa.).

The route by which the fluoro-substituted porphyrins of the present invention (component A) will be administered, and the form of the composition, will dictate the type of carrier (component B) to be used. The composition may be in a variety of forms, suitable, for example, for systemic administration (e.g., oral, rectal, nasal, sublingual, buccal, implants, or parenteral) or topical administration (e.g., local application on the skin, liposome delivery systems, or iontophoresis).

Carriers for systemic administration typically comprise at least one of a) diluents, b) lubricants, c) binders, d) disintegrants, e) colorants, f) flavors, g) sweeteners, h) antioxidants, j) preservatives, k) glidants, m) solvents, n) suspending agents, o) wetting agents, p) surfactants, combinations thereof, and others. All carriers are optional in the systemic compositions.

Ingredient a) is a diluent. Suitable diluents for solid dosage forms include sugars such as glucose, lactose, dextrose, and sucrose; diols such as propylene glycol; calcium carbonate; sodium carbonate; sugar alcohols, such as glycerin, mannitol, and sorbitol. The amount of ingredient a) in the systemic or topical composition is typically about 50 to about 90%.

Ingredient b) is a lubricant. Suitable lubricants for solid dosage forms are exemplified by solid lubricants including silica, talc, stearic acid and its magnesium salts and calcium salts, calcium sulfate; and liquid lubricants such as polyethylene glycol; and vegetable oils such as peanut oil, cottonseed oil, sesame oil, olive oil, corn oil and oil of theobroma. The amount of ingredient b) in the systemic or topical composition is typically about 5 to about 10%.

Ingredient c) is a binder. Suitable binders for solid dosage forms include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of ingredient c) in the systemic composition is typically about 5 to about 50%.

Ingredient d) is a disintegrant. Suitable disintegrants for solid dosage forms include agar, alginic acid and the sodium salt thereof, effervescent mixtures, croscarmelose, crospovidone, sodium carboxymethyl starch, sodium starch glycolate, clays, and ion exchange resins. The amount of ingredient d) in the systemic or topical composition is typically about 0.1 to about 10%.

Ingredient e) for solid dosage forms is a colorant such as an FD&C dye. When used, the amount of ingredient e) in the systemic or topical composition is typically about 0.005 to about 0.1%.

Ingredient f) for solid dosage forms is a flavor such as menthol, peppermint, and/or fruit flavors. The amount of ingredient f), when used, in the systemic or topical composition is typically about 0.1 to about 1.0%.

Ingredient g) for solid dosage forms is a sweetener such as aspartame and/or saccharin. The amount of ingredient g) in the systemic or topical composition is typically about 0.001 to about 1%.

Ingredient h) is an antioxidant such as butylated hydroxyanisole ("BHA"), butylated hydroxytoluene ("BHT"), and/or vitamin E. The amount of ingredient h) in the systemic or topical composition is typically about 0.1 to about 5%.

Ingredient j) is a preservative such as benzalkonium chloride, methyl paraben and/or sodium benzoate. The amount of ingredient j) in the systemic or topical composition is typically about 0.01 to about 5%.

Ingredient k) for solid dosage forms is a glidant such as silicon dioxide. The amount of ingredient k) in the systemic or topical composition is typically about 1 to about 5%.

Ingredient m) is a solvent, such as water, isotonic saline, ethyl oleate, glycerine, hydroxylated castor oils, and/or alcohols (such as ethanol, and phosphate buffer solutions). The amount of ingredient m) in the systemic or topical composition is typically from about 0 to about 100%.

Ingredient n) is a suspending agent. Suitable suspending agents include Avicel® RC-591 (from FMC Corporation of Philadelphia, Pa.) and/or sodium alginate. The amount of ingredient n) in the systemic or topical composition is typically about 1 to about 8%. Ingredient o) is a surfactant such as lecithin, Polysorbate 80, and sodium lauryl sulfate, and the TWEENS® from Atlas Powder. Company of Wilmington, Del. Suitable surfactants include those disclosed in the C.T.F.A. Cosmetic Ingredient Handbook, 1992, pp 0.587-592; Remington's Pharmaceutical Sciences, 15th Ed. 1975, pp. 335-337; and McCutcheon's Volume 1, Emulsifiers & Detergents, 1994, North American Edition, pp. 236-239. The amount of ingredient o) in the systemic or topical composition is typically about 0.1% to about 5%.

Although the amounts of components A and B in the systemic compositions will vary depending on the type of systemic composition prepared, the specific derivative selected for component A and the ingredients of component B, in general, system compositions comprise about 0.01% to about 50% of component A and about 50% to about 99.99% of component B.

Compositions for parenteral administration typically comprise about 0.01 to about 10% of the fluoro-substituted porphyrins of the present invention and about 90 to about 99.99% of a carrier comprising a) a diluent and m) a solvent. In one embodiment, diluent a) comprises propylene glycol and m) comprises ethanol or ethyl oleate.

Compositions for oral administration can have various dosage forms. For example, solid forms include tablets, capsules, granules, and bulk powders. These oral dosage forms comprise a safe and effective amount, usually at least about 5%, and more particularly from about 25% to about 50% of component A. The oral dosage compositions further comprise about 50 to about 95% of component B, and more particularly, from about 50 to about 75%.

Tablets can be compressed, tablet triturates, enteric-coated, sugar-coated, film-coated, or multiple-compressed. Tablets typically comprise component A, and component B, a carrier, comprising ingredients selected from the group consisting of a) diluents, b) lubricants, c) binders, d) disintegrants, e) colorants, f) flavors, g) sweeteners, k) glidants, and combinations thereof. Specific diluents include calcium carbonate, sodium carbonate, mannitol, lactose and cellulose. Specific binders include starch, gelatin, and sucrose. Specific disintegrants include alginic acid and croscarmelose. Specific lubricants include magnesium stearate, stearic acid, and talc. Specific colorants are the FD&C dyes, which can be added for appearance. Chewable tablets preferably contain g) sweeteners such as aspartame and saccharin, or f) flavors such as menthol, peppermint, fruit flavors, or a combination thereof.

Capsules (including implants, time release and sustained release formulations) typically comprise component A1 and a carrier comprising one or more a) diluents disclosed above in a capsule comprising gelatin. Granules typically comprise component A, and preferably further comprise k) glidants such as silicon dioxide to improve flow characteristics. Implants can be of the biodegradable or the non-biodegradable type. Implants may be prepared using any known biocompatible formulation.

The selection of ingredients in the carrier for oral compositions depends on secondary considerations like taste, cost, and shelf stability, which are not critical for the purposes of this invention. One skilled in the art would know how to select appropriate ingredients without undue experimentation.

The solid compositions may also be coated by conventional methods, typically with pH or time-dependent coatings, such that component A is released in the gastrointestinal tract in the vicinity of the desired application, or at various points and times to extend the desired action. The coatings typically comprise one or more components selected from the group consisting of cellulose acetate phthalate, polyvinyl acetate phthalate, hydroxypropyl methyl cellulose phthalate, ethyl cellulose, EUDRAGIT® coatings (available from Rohm & Haas G. M. B. H. of Darmstadt, Germany), waxes and/or shellac.

Compositions for oral administration can also have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically comprise component A and component B, namely, a carrier comprising ingredients selected from the group consisting of a) diluents, e) colorants, f) flavors, g) sweeteners, j) preservatives, m) solvents, n) suspending agents, and o) surfactants. Peroral liquid compositions preferably comprise one or more ingredients selected from the group consisting of e) colorants, f) flavors, and g) sweeteners.

Other compositions useful for attaining systemic delivery of the subject fluoro-substituted porphyrins include sublingual, buccal and nasal dosage forms. Such compositions typically comprise one or more of soluble filler substances such as a) diluents including sucrose, sorbitol and mannitol; and c) binders such as acacia, microcrystalline cellulose, carboxymethyl cellulose, and hydroxypropyl methylcellulose. Such compositions may further comprise b) lubricants, e) colorants, f) flavors, g) sweeteners, h) antioxidants, and k) glidants.

In one embodiment of the invention, the fluoro-substituted porphyrins of the present-invention are topically administered.

Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions comprise: component A, the fluoro-substituted porphyrins described above, and component B, a carrier. Component B may further comprise one or more optional components.

The exact amounts of each component in the topical composition depend on various factors. The amount of component A added to the topical composition is dependent on the IC50 of component A, typically expressed in nanomolar (nM) units. For example, if the IC50 of the medicament is 45 nM, the amount of component A will be from about 0.04 to about 4%. If the IC50 of the medicament is 100 nM, the amount of component A will be from about 0.08 to about 8%. If the IC50 of the medicament is 1000 nM, the amount of component A will be from about 0.8 to about 80%. If the amount of component A is outside the ranges specified above (i.e., lower), efficacy of the treatment may be reduced. One skilled in the art understands how to calculate and understand an IC50. The remainder of the composition, up to 100%, is component B.

The amount of the carrier employed in conjunction with component A is sufficient to provide a practical quantity of composition for administration per unit dose of the medicament. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

Component B may comprise a single ingredient or a combination of two or more ingredients. In the topical compositions, component B comprises a topical carrier. Suitable topical carriers comprise one or more ingredients selected from the group consisting of phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols and symmetrical alcohols.

The carrier of the topical composition may further comprise one or more ingredients selected from the group consisting of q) emollients, r) propellants, s) solvents, t)

humectants, u) thickeners, v) powders, w) fragrances, x) pigments, and y) preservatives.

Ingredient q) is an emollient. The amount of ingredient q) in a skin-based topical composition is typically about 5 to about 95%. Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane.

Ingredient r) is a propellant. The amount of ingredient r) in the topical composition is typically about 0 to about 95%. Suitable propellants include propane, butane, isobutane, dimethyl ether, carbon dioxide, nitrous oxide, and combinations thereof.

Ingredient s) is a solvent. The amount of ingredient s) in the topical composition is typically about 0 to about 95%. Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols.

Ingredient t) is a humectant. The amount of ingredient t) in the topical composition is typically 0 to 95%. Suitable humectants include glycerin, sorbitol, sodium 2-pyrrolidone-5-carboxylate, soluble collagen, dibutyl phthalate, gelatin, and combinations thereof. Specific humectants include glycerin.

Ingredient u) is a thickener. The amount of ingredient u) in the topical composition is typically about 0 to about 95%.

Ingredient v) is a powder. The amount of ingredient v) in the topical composition is typically 0 to 95%. Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof.

Ingredient w) is a fragrance. The amount of ingredient w) in the topical composition is typically about 0 to about 0.5%, particularly, about 0.001 to about 0.1%.

Ingredient x) is a pigment. Suitable pigments for skin applications include inorganic pigments, organic lake pigments, pearlescent pigments, and mixtures thereof. Inorganic pigments useful in this invention include those selected from the group consisting of rutile or anatase titanium dioxide, coded in the Color Index under the reference Cl 77,891; black, yellow, red and brown iron oxides, coded under references Cl 77,499, 77,492 and, 77,491, manganese violet (Cl 77,742), ultramarine blue (Cl 77,007), chromium oxide (Cl 77,288), chromium hydrate (Cl 77,289), and ferric blue (Cl 77,510) and mixtures thereof The organic pigments and lakes useful in this invention include those selected from the group consisting of D&C Red No 19 (Cl 45,170), D&C Red No 9 (Cl 15,585), D&C Red No 21 (Cl 45,380), D&C Orange No 4 (Cl 15,510), D&C Orange No 5 (Cl 45,370), D&C Red No 27 (Cl 45,410), D&C Red No 13 (Cl 15,630), D&C Red No 7 (Cl 15,850), D&C Red No 6 (Cl 15,850), D&C Yellow No 5 (Cl 19,140), D&C Red No 36 (Cl 12,085), D&C Orange No 10 (Cl 45,425), D&C Yellow No 6 (Cl 15,985), D&C Red No 30 (Cl 73,360), D&C Red No 3 (Cl 45,430), the dye or lakes based on Cochineal Carmine (Cl 75,570) and mixtures thereof The pearlescent pigments useful in this invention include those selected from the group consisting of the white pearlescent pigments such as mica coated with titanium oxide, bismuth oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof. The amount of pigment in the topical composition is typically about 0 to about 10%

Component A may be included in kits comprising component A, a systemic or topical composition described above, or both, and information, instructions, or both that use of the kit will provide treatment for cosmetic and medical conditions in mammals (particularly humans). The information and instructions may be in the form of words, pictures, or both, and the like. In addition or in the alternative, the kit may comprise the medicament, a composition, or both, and information, instructions, or both, regarding methods of application of medicament, or of composition, preferably with the benefit of treating or preventing cosmetic and medical conditions in mammals (e. g., humans).

The present invention is explained in greater detail in the following non-limiting Examples.

EXAMPLES

Examples 1-2: Synthesis of Symmetrically Meso-Substituted Cationic N-Fluoroalkylpyridyl Porphyrins Reactions are performed according to the methods previously described (Tovmasyan et al. (2013) *Inorg Chem* 52:5677-5691), and as further modified and described below. The overall synthesis consists of the following three major steps (Schemes 1-2).

Scheme 1. Synthesis of symmetrically *meso*-substituted cationic *N*-fluoroalkylpyridyl porphyrins (Steps 1-2).

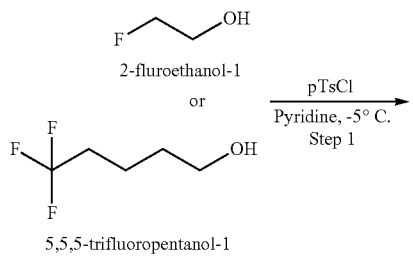

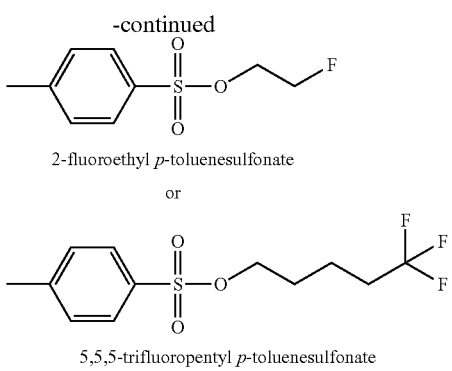

2-fluoroethyl p-toluenesulfonate or 5,5,5-trifluoropentyl p-toluenesulfonate

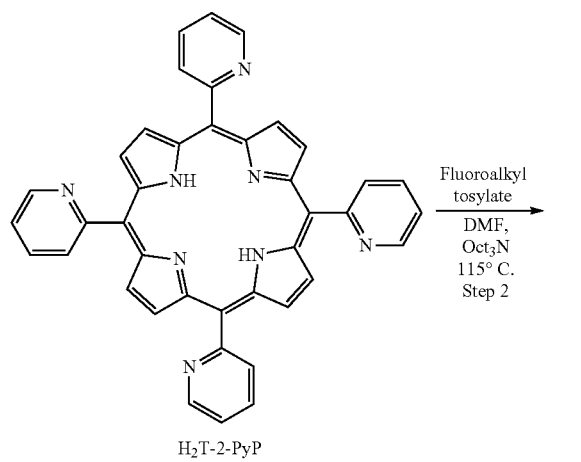

H₂T-2-PyP

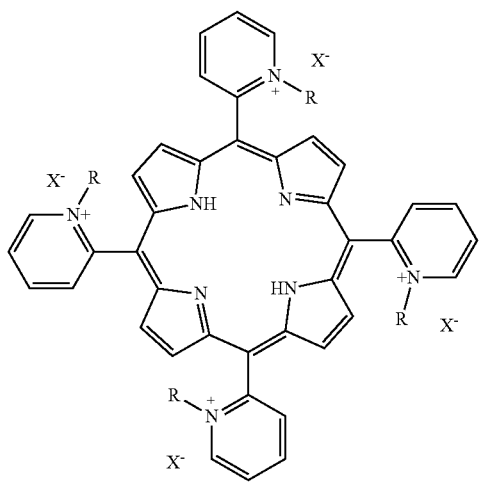

X⁻ = Ts⁻ = H₂TF$_x$Alk——2-PyP⁵⁺ × 4(Ts⁻)
X⁻ = PF₆⁻ = H₂TF$_x$Alk——2-PyP⁵⁺ × 4(PF₆⁻)
X⁻ = Cl⁻ = H₂TF$_x$Alk——2-PyP⁵⁺ × 4(Cl⁻)

Step 1: Preparation of Fluoroalkyl Tosylates. Fluoroalkyl tosylates (2-fluoroethyl p-toluenesulfonate or 5,5,5-trifluoropentyl p-toluenesulfonate) were synthesized according to our previously published method (Tovmasyan et al. (2013) *Inorg Chem* 52, 5677-5691; Rajic et al. (2012) *Free Radic Biol Med* 52, 1828-1834). Briefly, fluoroalcohol was dissolved in pyridine and stirred in an ice bath (prepared with NaCl) for 10 min at −5° C. to −10° C. p-Toluenesulfonyl chloride (equimolar to alcohol) was added portionwise and stirred during 5 hours at −5° C. The reaction progress was followed by TLC using 1:5=ethyl acetate:hexane solvent system. Water (2× vol.) was added to the reaction mixture and stirred for 10 min to dissolve the formed precipitate. The organic layer was separated from the mixture and washed with 2 M HCl (1× vol. four times). The organic layer was then neutralized with the aqueous solution of $NaHCO_3$ and dried over $Na_2SO_4$. This method afforded quantitative yields.

Step 2: N-Quaternization.

N-quaternization (fluoroalkylation) was performed as previously described for analogous alkyl derivatives (Batinić-Haberle et al. (2002) *Journal of the Chemical Society, Dalton Transactions* 2689-2696). Briefly, to a solution of porphyrinic ligand ($H_2$T-2-PyP) fluoroalkyl p-toluenesulfonate (2-fluoroethyl p-toluenesulfonate or 5,5,5-trifluoropentyl p-toluenesulfonate) was added in 300-fold molar excess and stirred in anhydrous DMF at 115° C. The course of the reaction progress was followed by TLC using 1:1:8=$KNO_3$(sat):$H_2O$:$CH_3CN$ as a mobile phase. The N-quaternization was complete after 41 and 47 hours for $H_2$TFE-2-PyP$^{4+}$ and $H_2$TF$_3$Pen-2-PyP$^{4+}$, respectively. Once completed, the reaction mixture was precipitated by diethyl ether, washed with diethyl ether/acetone mixture (1/3 v/v) and air-dried. The precipitate was dissolved into water, kept in the refrigerator for 1 hr at 4° C. and was then filtered through smooth paper filter. The porphyrin was precipitated from the solution as a $PF_6^-$ salt by the addition of $NH_4PF_6$ salt. The precipitate was filtered off and washed thoroughly with anhydrous diethyl ether. The dried precipitate was then dissolved in acetone and precipitated as a chloride salt by the addition of a saturated acetone solution of trioctylmonomethylammonium chloride. The precipitate was washed thoroughly with acetone and dried under reduced pressure.

Difficulties:

Fluoroalkylation reactions, in general, were shown to proceed with slower rates, which are most likely due to the lower stability of the fluoroalkyl carbocation formed during the quaternization reaction as compared to alkyl. As such, N-fluoroethylation reaction proceeded slower as compared to N-ethylation. The trifluoroethylations of pyridyl nitrogens, tested with both tosylate and iodide, proceeded with minimum to no detectable yields.

Scheme 2. Synthesis of symmetrically *meso*-substituted cationic *N*-fluoroalkylpyridyl porphyroms (Steps 3.1 and 3.2).

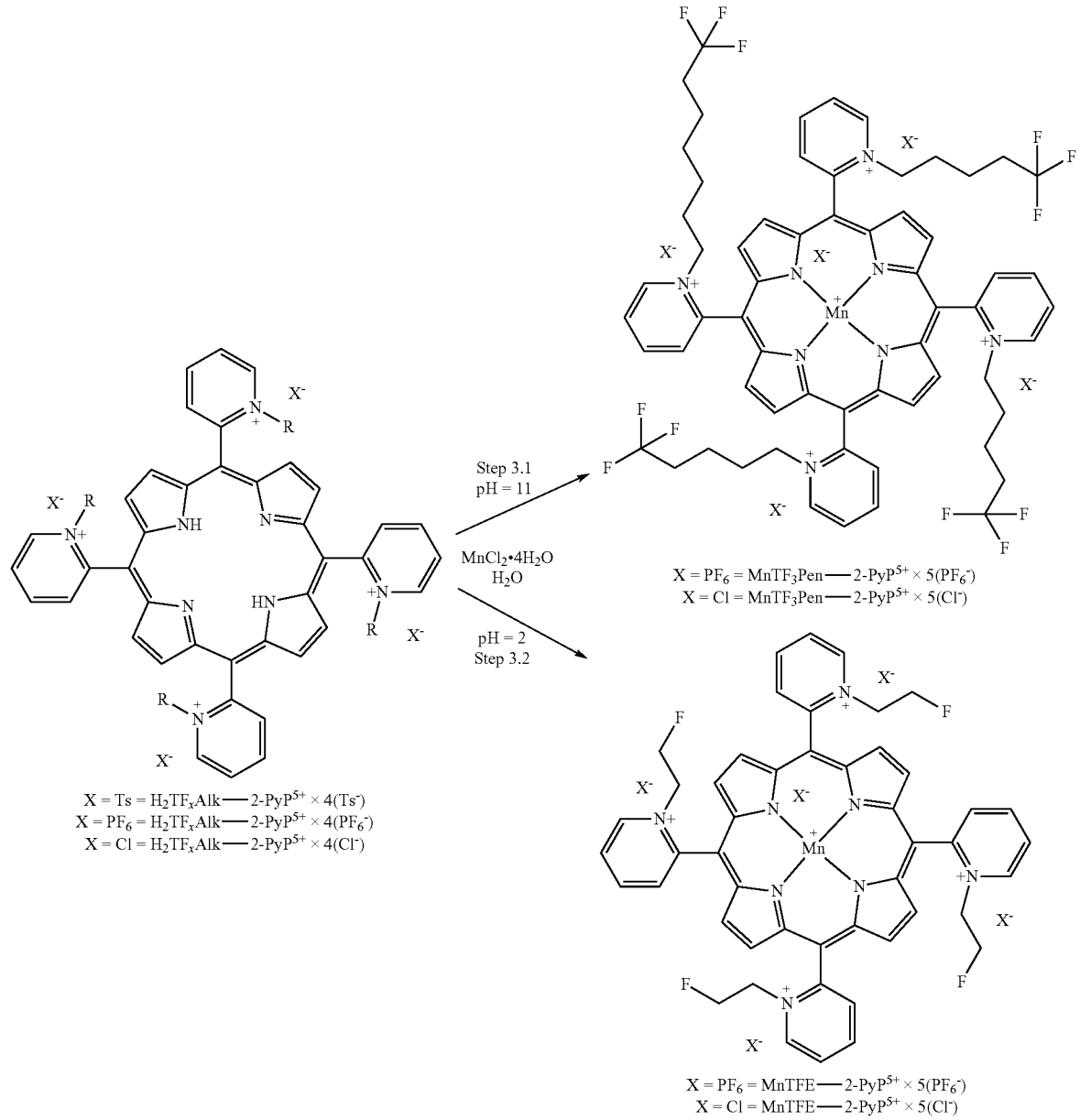

Step 3: Metallation.

The metallation of cationic N-substituted porphyrinic ligands is performed in the aqueous solution at two distinctly different conditions: alkaline (Step 3.1. 5,10,15,20-tetra(Mn (III) 5′,5′,5′-trifluoropentylpyridinium-2-yl)porphinato pentachloride; MnTF$_3$Pen-2-PyP$^{5+}$, Mn4) and acidic (Step 3.2. Mn(III) 5,10,15,20-tetra(2-fluoroethylpyridinium-2-yl)porphinato pentachloride; MnTFE-2-PyP$^{5+}$, Mn3).

Step 3.1. MnTF$_3$Pen-2-PyP$^{5+}$:

the solution of 1.5 mM H$_2$TF$_3$Pen-2-PyP$^{4+}$, adjusted to pH~11 (with 1 M NaOH), 20-fold molar excess MnCl$_2$× 4H$_2$O was added and stirred at 75° C. The course of the metalation reaction was followed on silica gel TLC plates using 1:1:8=KNO$_3$(sat):H$_2$O:CH$_3$CN as a mobile phase. Additionally, the loss of metal-free porphyrin fluorescence under UV light at ~350 nm was determined. After the metalation reaction was complete (~3.5 hours), the solution was first filtered through coarse filter paper and then through fine filter paper. The Mn porphyrin precipitated as a PF$_6^-$ salt with a saturated aqueous solution of NH$_4$PF$_6$ and subsequently as a chloride salt with tetrabutylammonium chloride. The isolation and purification of Mn porphyrins was done as described for the free ligands in the alkylation section (see step 1 above). Additionally, the whole precipitation procedure was repeated once again to assure full removal of low-molecular weight Mn complexes and high purity of preparation (see step 2 above). The described method previously had afforded quantitative yields (Tovmasyan et al. (2013) *Inorg Chem* 52:5677-5691; Tovmasyan et al. (2011). *Dalton Trans* 40, 4111-4121).

Step 3.2. MnTFE-2-PyP$^{5+}$:

to the solution of 1.5 mM H$_2$TFE-2-PyP$^{4+}$, adjusted to pH~2 (with 1 M HCl), 20-fold molar excess MnCl$_2$×4H$_2$O was added and stirred at 75° C. The course of metallation reaction was followed as with MnTF$_3$Pen-2-PyP$^{5+}$ described above. After the metallation reaction was complete (~68 hours), the solution was cooled and the pH of the reaction mixture was increased to pH~6. The solution was next filtered first through a coarse then filter paper and then through a fine filter paper and worked up similar to the MnTF$_3$Pen-2-PyP$^{5+}$. This method afforded quantitative yields.

Difficulties:

Various side products were observed, which are initially attributed to the loss of fluorine atom(s)/replacement by hydroxyl group, when the metallation reaction of H$_2$TFE-2-PyP$^{4+}$ porphyrin was carried out under alkaline conditions. As formed, the impurities are of porphyrin-type and purification of target compound would create difficulties in industrial preparation of the product as chromatographic separation sought to be prohibited in scale-up synthesis. Formation of undesired products was prevented by performing reaction under acidic conditions, at pH~2. However, the latter condition creates difficulties in the further step of compound isolation/purification. Precipitation of the compound does not occur under such lowered pH and, as such, prior increase of pH~6 to pH~11 is needed for better precipitation/purification.

Comparative Example A

Mn(III) Meso-Tetrakis(Trifluoroethylpyridinium-2-Yl) Porphyrin Cannot be Synthesized It was originally proposed to synthesize fluorinated MnTE-2-PyP$^{5+}$ where the 3 hydrogen atoms in the methyl group of —CH$_2$CH$_3$ are replaced with fluorine atoms, as depicted in Scheme IA. However, attempting to synthesize this compound by fluoroalkylation of H$_2$T-2-PyP using (2,2,2-trifluoroethane)phenyliodonium triflate (Umemoto and Gotoh (1987) *Bull. Chem. Soc. Jpn.* 60, 3307-3313; Umemoto and Gotoh (1991) *Bull. Chem. Soc. Jpn.* 64, 2008-2010) in anhydrous DMF at 50° C. and protected from moisture, failed to yield the desired product.

Scheme IA

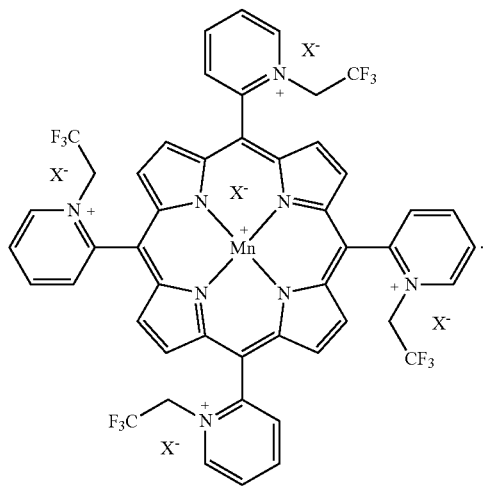

Fluorine is the most electronegative element in the periodic table and its electronegativity controls its chemistry and limits its synthetic options.

Various other methods were employed to attempt to synthesize the porphyrin of Scheme IA, with trifluoroethyl substituents at the ortho position of the pyridyl rings. Interaction of meso-tetrakis(2-pyridyl)porphyrin with alkylating agents, 2,2,2-trifluoroethyl p-toluenesulphonate and 2,2,2-trifluoroethyl iodide, which are the most commonly used reagents in the quaternization of pyridyl nitrogens in porphyrin, did not yield the desired product. The reaction of meta porphyrin isomer (meso-tetrakis(3-pyridyl)porphyrin), which is less sterically hindered as compared to ortho pyridyl-porphyrin, also did not result in the anticipated product. An alternative route, i.e. the quaternization of metalloporphyrin, e.g. Mn(III) meso-tetrakis(2-pyridyl)porphyrin, by various alkylating reagents proceed with much slower rates as compared to the reactions involving freebase porphyrins. Therefore, such reaction is unproductive. We have also attempted to synthesize a porphyrin with 2,2-difluoroethyl substituents, yet with no success. After 4 days of stirring at 115° C. the reaction did not go to completion. These various attempts indicate that the preparation of meso-tetrakis(2,2,2-trifluoroethylpyridinium-2-yl) porphyrin, as set forth in Scheme IA, according to conventional means is unfeasible.

The electron-withdrawing effect of several fluorine atoms does not allow for a bond to be established between nitrogen and ethylcarbocation. Moreover three fluorine atoms, in the ortho position of the pyridyl chains impose steric hindrance towards beta pyrrolic hydrogens, which further preclude this reaction from occurring to any significant extent.

However, the replacement of only one hydrogen atom with fluorine in the ethyl chains allowed us to achieve complete quaternization of pyridyl-porphyrins. A pure compound was isolated and used in different animal and cellular cancer models. It should be noted, that this monofluoroethylation reaction proceeded with a notably slower rate compared to its non-fluorinated ethyl analog.

Comparative Example B

Mn(III) Meso-Tetrakis (Trifluoroethoxybutylpyridinium-2-Yl) Porphyrin Cannot be Synthesized It has also been previously understood how the position of oxygen atoms affects the ability to synthesize the product depicted in Scheme IIA. However, only a compound with short ethyl chains next to nitrogen atoms and butyl chains on the other side of oxygen atoms can be made. See, for example, MnTnBuOE-2-PyP$^{5+}$ (Formula 001).

Scheme IIA

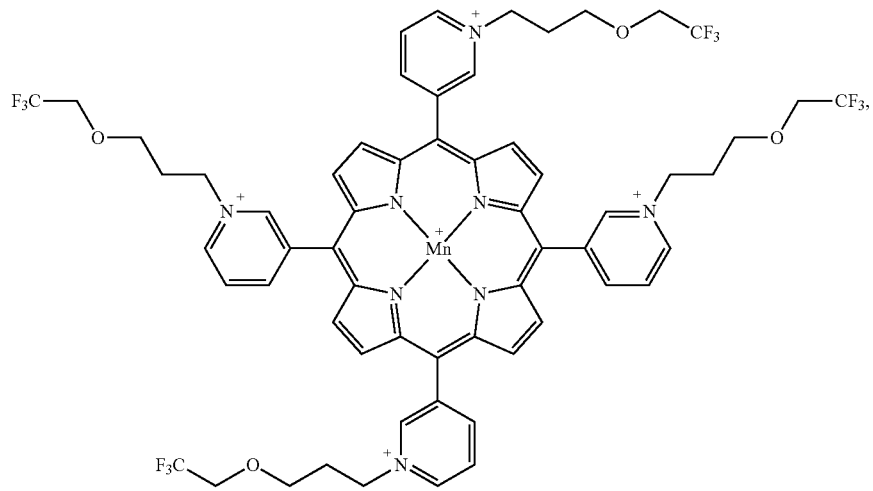

It was originally proposed to synthesize fluorinated MnTnPrOH-3-PyP$^{5+}$ where the 3 hydrogen atoms in the methyl group of —$CH_2CH_2CH_2OCH_2CH_3$ are replaced with fluorine atoms, as depicted in Scheme IIA. However, attempting to synthesize this compound by fluoroalkylation of the alkoxide derivative of MnTnPrOH-3-PyP$^{5+}$, prepared by alcohol deprotonation with lithium hydride (10 equiv.), with (2,2,2-trifluoroethane)phenyliodonium triflate (Umemoto and Gotoh (1987) Bull. Chem. Soc. Jpn. 60, 3307-3313; Umemoto and Gotoh (1991) Bull. Chem. Soc. Jpn. 64, 2008-2010) in anhydrous DMF, heated for 24 hours at 50° C. and protected from moisture, failed to yield the desired product.

Moreover, butyl chains next to nitrogen atoms as they are in the compound of Scheme IIA allow for cyclic rearrangements and would result in an array of species which have differing numbers of ethyl chains on the nitrogen atoms instead of four ethoxybutyl chains. Problems associated with such rearrangements are described in Rajic Z, Tovmasyan A, de Santana O L, Peixoto I N, Spasojevic I, do Monte S A, Ventura E, Reboucas J S, and Batinic-Haberle I. Challenges encountered during development of Mn porphyrin-based, potent redox-active drug and superoxide dismutase mimic, MnTnBuOE-2-PyP5+, and its alkoxyalkyl analogues. J Inorg Biochem 169: 50-60, 2017. Thus, it is not possible to synthesize structure depicted in Scheme IIA according to conventional methods.

In addition to such problems that control the formation of a variety of compounds in the final preparation, the impact of 3 fluorine atoms at the end of the chains may have a detrimental impact on the synthesis and metallation steps. Two strong electron-withdrawing effects from opposite sides of the oxygen atoms—from the nitrogen atoms and from the fluorine atoms—destabilize the ether linkage and preclude the formation of the porphyrin and its Mn complex. Finally, the design of such a molecule having polar fluorine atoms along with polar oxygen atoms, based on our present knowledge, would end up with reduced lipophilicity and therefore reduced bioavailability. Issues with MnTnBuOE-2-PyP$^{5+}$ regarding bioavailability have been experienced and are not understood completely—e.g., it does not offer protection in a stroke model when given subcutaneously (while hexyl analog, MnTnHex-2-PyP$^{5+}$ does). However its redox properties allow it to be protective in a stroke model if given intracerebroventricularly.

All above discussions related to the structure IIA are made possible based on our comprehensive knowledge of the synthesis of oxygen-derivatized Mn porphyrins gained over last 5 years and was not available at the moment the structure was proposed. Neither by us nor by anybody else can structure IIA be synthesized.

From both the synthetic and bioavailability prospective we have decided to synthesize compounds with differently substituted fluoroalkyl chains, where fluorine atoms are either far away from nitrogens or are few in numbers, in order to have a lipophilic fluoro Mn porphyrin as an alternative for potentially treating CNS injuries.

The first fluoro Mn porphyrin was designed so that it has sufficient lipophilicity and could be easily synthesized on GMP scale—the trifluoropentyl compound, MnTF$_3$Pen-2-PyP$^{5+}$ (Formula III).

Example 3: In Vivo Effects of Fluoro MnPs Versus Non-Fluoro MnPs

Table 1 lists properties of fluorinated MnPs and their non-fluorinated analogs. These are the major properties that control their in vitro and in vivo actions.

Table 1. Physical and Chemical Properties of Mn Complexes.

Listed are values for fluorinated compounds and analogous non-fluorinated MnPs: redox property expressed as metal-centered reduction potential for the Mn$^{III}$P/Mn$^{II}$P redox couple, $E_{112}$ in mV vs normal hydrogen electrode, NHE; $v_o(Asc)_{ox}$, ability to oxidize ascorbate expressed as initial rate using P/Mn$^{II}$P redox couple; lipophilicity expressed as $R_f$—the ratio of MnP path to solvent path on silica plate where the solvent is 1:1:8, KNO$_{3(sat)}$:H$_2$O: acetonitrile; ability to mimic SOD enzyme in the catalysis of $O_2^-$ dismutation expressed as log $k_{cat}(O_2^-)$.

| MnP | $E_{1/2}$, mV vs NHE | $v_0$(Asc oxid), nM s$^{-1}$ | f | log $k_{cat}$ (O$_2^-$) |
|---|---|---|---|---|
| MnTE-2-PyP$^{5+}$, Mn1 | +228 | 321 | .06 | 7.76 |
| MnTnBuOE-2-PyP$^{5+}$, Mn2 | +277 | 296 | .43 | 7.83 |
| MnTnPen-2-PyP$^{5+}$ | +278 | 164 | .32 | 7.36 |
| MnTFE-2-PyP$^{5+}$, Mn3 | +242 | 543 | .11 | 7.91 |
| MnTF3Pen-2-PyP$^{5+}$, Mn4 | +288 | 297 | .43 | 7.48 |

In any studies that have been performed thus far fluoro-substituted porphyrins exhibited superior characteristics than their non-fluorinated counterparts.

Figure 2:
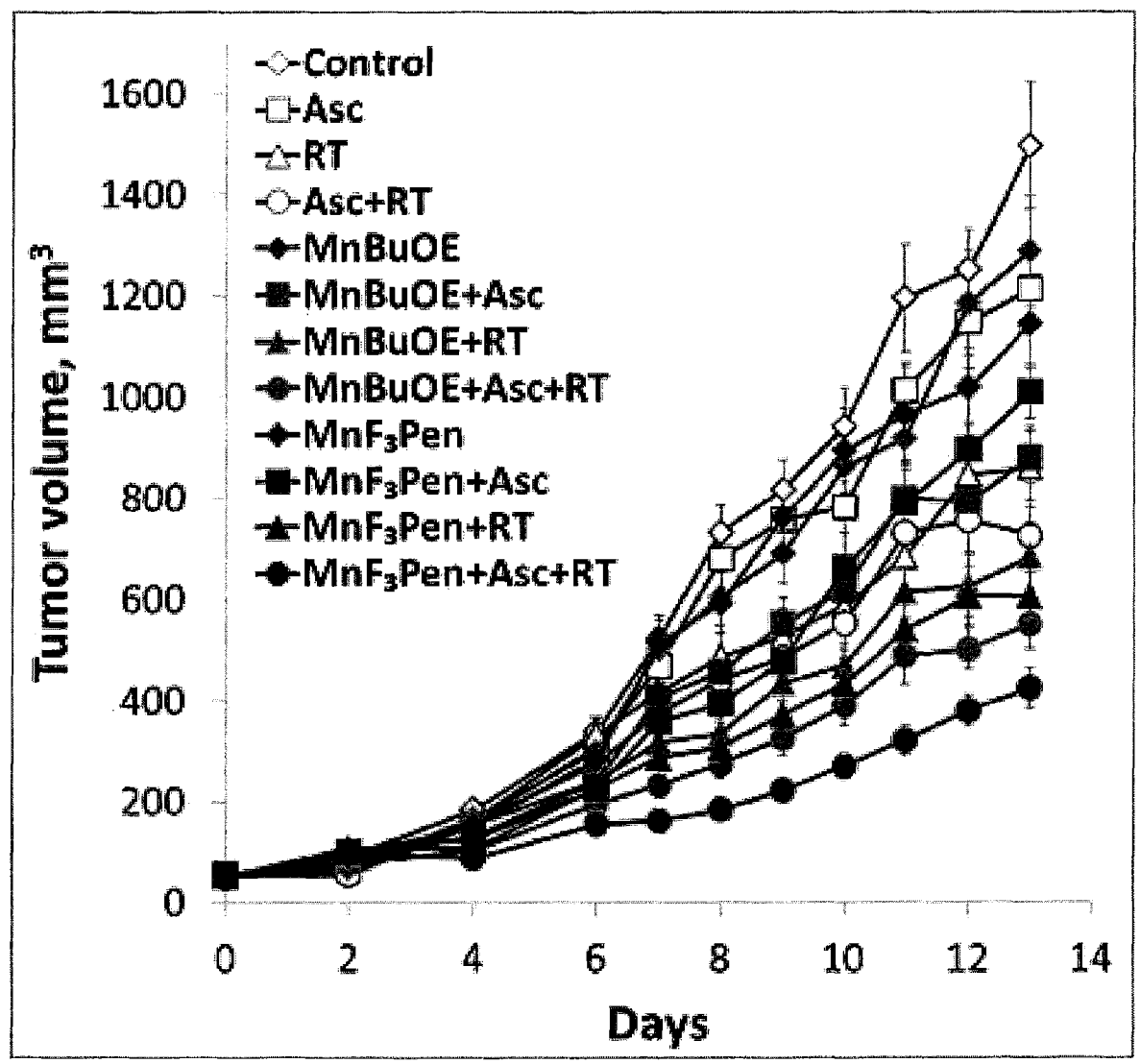
FIG. 2 Anticancer effect of MnTnBuOE-2-PyP$^{5+}$ (Mn2, also referred to as MnBuOE) vs MnTF$_3$Pen-2-PyP$^{5+}$ (Mn4, also referred to as MnF$_3$Pen). Female Balb/c mice were injected subcutaneously (on flank) with 1 million cells. When tumors reached on average volume of 60-80 mm$^3$, the two Mn porphyrins, BMX-001 (MnTnBuOE-2-PyP$^{5+}$ and MnTnF$_3$Pen-2-PyP$^{5+}$) were injected subcutaneously at 0.2 mg/kg/day and continued daily afterwards; the doses are very low and clinically relevant and indicate catalytic potency of Mn porphyrins. Also the injection of ascorbate (Asc) started at 4 g/kg/day for first 6 days and then at 1 g/kg/day until the 24 hours before the completion of study. 24 hours after the first injection of Mn porphyrins the radiation started at 2.5 Gy per day for 3 days. Fractionated radiation regime was used to better reflect the clinical scenario. Radiation (RT) doses lower than doses that would compare readily to the clinical ones were used to be able to see the contribution of radiation and ascorbate each to the effect of MnPs. Injection of drugs was continued daily. Once the study was completed when mice reached on average 2000 mm$^3$ volume, the mice were sacrificed, and tumors, normal muscle from opposite leg and liver were collected and levels of Mn porphyrins analyzed by LCMS/MS.

A mouse breast tumor radio- and chemosensitization study where MnTF$_3$Pen-2-PyP$^{5+}$ (Formula III, MnF$_3$Pen, Mn4) and MnTnBuOE-2-PyP$^{5+}$ (Formula 001, MnBuOE, Mn2) were compared (both having similar SOD-like activities and bioavailabilities) and shown in FIG. 2, alone and in combination with ascorbate and/or radiation therapy. The last two data series (• and •) shown in FIG. 2 depict the tumor growth inhibition as a result of a triple combination of Mn porphyrin, radiation and ascorbate. These data show that the triple combination of MnTF$_3$Pen-2-PyP$^{5+}$ with ascorbate and radiation therapy results in larger tumor growth inhibition when compared to the same triple combination of MnTnBuOE-2-PyP$^{5+}$ with ascorbate and radiation therapy. Both compounds have similar abilities to catalyze ascorbate oxidation and cytotoxic peroxide production and are of similar lipophilicities. This advantageous effect would not have been expected without understanding their bioavailabilities and reactivities towards biomolecules such as ascorbate where differences in polarity play a major role. Also, such differences could not have been anticipated based just on the aqueous chemistry and diverse physical properties of those compounds. Such effects likely result from the differences in the polarities of those molecules: strongly polar character of 12 fluorine atoms relative to 4 polar oxygen atoms. The study in FIG. 2 was done with 10-fold lower doses—0.2 mg/kg of MnTnBuOE-2-PyP$^{5+}$ (MnBuOE, Mn2) and MnTF$_3$Pen-2-PyP$^{5+}$ (MnF$_3$Pen, Mn4) (in combination with RT and ascorbate) and 4T1 breast tumor grown as compared to data in FIG. 8 where MnPs were injected sc at 2 mg/kg. Strong tumor suppression was observed with the triple combination. Despite being equally lipophilic, a higher efficacy of MnTF$_3$Pen-2-PyP$^{5+}$ than MnTnBuOE-2-PyP$^{5+}$ was observed. To note, MnTF$_3$Pen-2-PyP$^{5+}$ exhibited less toxicity in a rat and mouse study than MnTnBuOE-2-PyP$^{5+}$.

Figure 3:
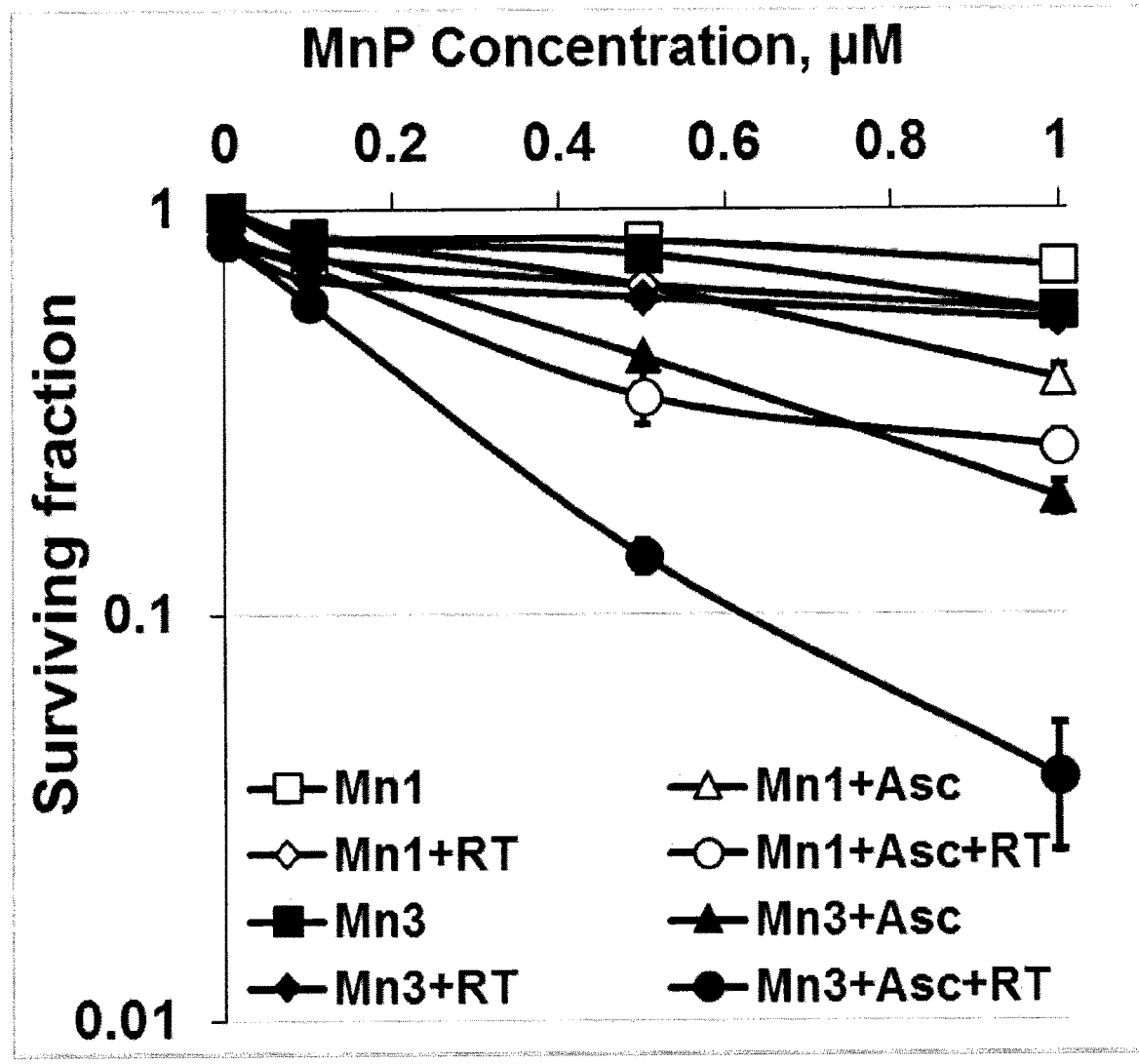
FIG. 3 Clonogenic survival of PC3 cells treated with manganese porphyrins alone or in combination with radiation (RT) and ascorbate (Asc). Aggressive prostate tumor PC-3 cells were treated overnight with PBS, MnTE-2-PyP$^{5+}$ (Mn1), or MnTFE-2-PyP$^{5+}$ (Mn3) using doses of 0.1 µM, 0.5 µM, and 1 µM. The following day half of each treatment group was incubated for 1 hour in 0.5 mM ascorbate, then either sham irradiated or exposed to 1 Gy x-rays (Rad Source RS-2000 X-Ray irradiator at UNMC) at a dose rate of 2 Gy/min Immediately following radiation treatment the cells were trypsinized, detached and counted. Each sample was serially diluted, and seeded into 6-well plates at 500 cells/well in three technical replicates. The cells were allowed to grow for 11 days then fixed with 70% EtOH and stained in 0.5% crystal violet and 25% methanol. Colonies containing 50 or more cells were counted and reported as the surviving fraction of cells seeded, normalized to plating efficiency of untreated cells at the same density. These experiments were repeated in triplicate and the mean and SEM were reported.
Figure 5:
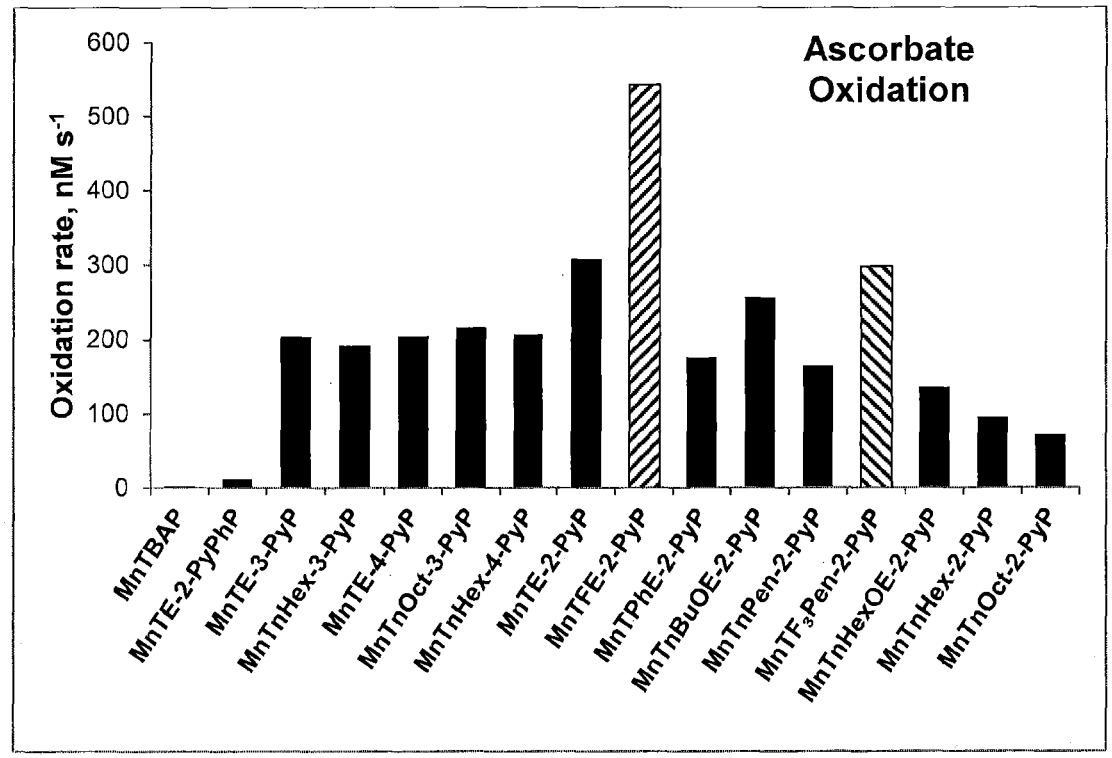
FIG. 5 Ability of MnP to catalyze ascorbate oxidation (with subsequent hydrogen peroxide formation which in turn kills tumor) as assessed spectrally via determination of initial rates of ascorbate oxidation. MnP/Asc cycled under aerobic conditions, whereby oxygen is consumed through reduction to superoxide and its subsequent reduction to H$_2$O$_2$. The ascorbate oxidation rate was measured with 10 µM MnP and 1 mM Asc under aerobic conditions ([O$_2$]= 0.255 mM) at (25±1°) C. and at pH 7.8 maintained with either 0.05 M phosphate or Tris buffer. The striped bars correspond to fluorinated compounds, monofluoroethylated MnTFE-2-PyP$^{5+}$ (MnFE, Mn3) vs ethylated MnTE-2-PyP$^{5+}$ (MnE, Mn1) and trifluoropentylated MnTFe$_3$Pen-2-PyP$^{5+}$ (MnF$_3$Pen, Mn4), vs pentylated MnTnPen-2-PyP$^{5+}$. Non-fluoro compounds are listed in front of fluoro analogs.

Example 4: Anti-Cancer Effect of MnTFE-2-PyP$^{5+}$ in a Radiation Resistant Prostate Cancer Cell Line FIG. 3 depicts the results from an examination of the effectiveness of MnTFE-2-PyP$^{5+}$ (Mn3, FIG. 1, Formula II) in killing the radiation-resistant prostate cancer cell line (PC3) compared with its non-fluorinated analog, MnTE-2-PyP$^{5+}$ (Mn1, FIG. 1)). Similar to the results shown in the comparison of MnTF$_3$Pen-2-PyP$^{5+}$ and MnTnBuOE-2-PyP$^{5+}$ described in EXAMPLE 3, the triple combination of MnTFE-2-PyP$^{5+}$ with ascorbate and radiation therapy exhibits superior cytotoxicity towards the radiation-resistant prostate cancer cell line than that of MnTE-2-PyP$^{5+}$ that would not have been expected without understanding reactivities towards biomolecules such as ascorbate where differences in polarity plays a major role (FIG. 5 and Table 1). Fluoro porphyrins distribute less in vivo than do non-fluoro analogs (FIG. 6) but seem to have kinetic advantage in producing larger therapeutic effects.

Examples 5-7

Further Comparison of Fluorinated Versus Non-Fluorinated Analogs.

Figure 4:
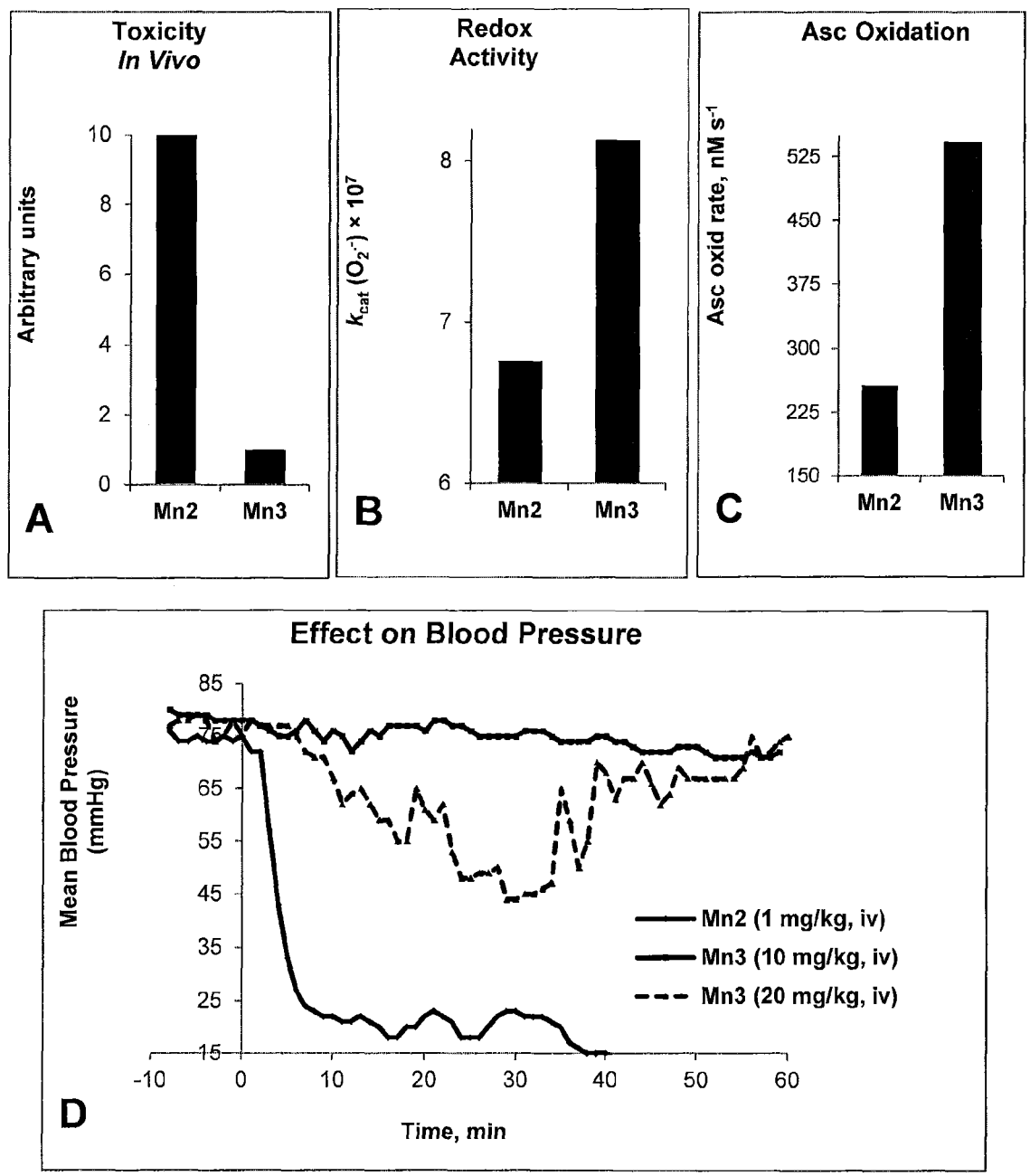
FIG. 4 Superior properties of fluorinated MnTFE-2-PyP$^{5+}$ (Mn3) over the non-fluorinated compound presently in clinical trials MnTnBuOE-2-PyP$^{5+}$ (Mn2) and ability of MnP to catalyze ascorbate oxidation as assessed spectrally. Mn3 has: (panel A) ~10-fold lower mouse toxicity; (panel B) largely improved redox activity with regards to SOD mimicking; (panel C) increased catalytic potency with regards to Asc oxidation which process results in H$_2$O$_2$ production and leads to its subsequent utilization in modification of cysteines of signaling proteins thereby affecting oxidative stress. MnP/Asc cycled under aerobic conditions, whereby oxygen is consumed through reduction to superoxide, which further dismutes into H$_2$O$_2$. The ascorbate oxidation rate was measured with 10 µM MnP and 1 mM Asc under aerobic conditions ([O$_2$]=0.255 mM) at (25±1°) C. and at pH 7.8 maintained with either 0.05 M phosphate or Tris buffer. (panel D) Fluorinated compound Mn3 exhibits >10-fold lower hypotension which frequently limits MnP dosing.
Figure 6:
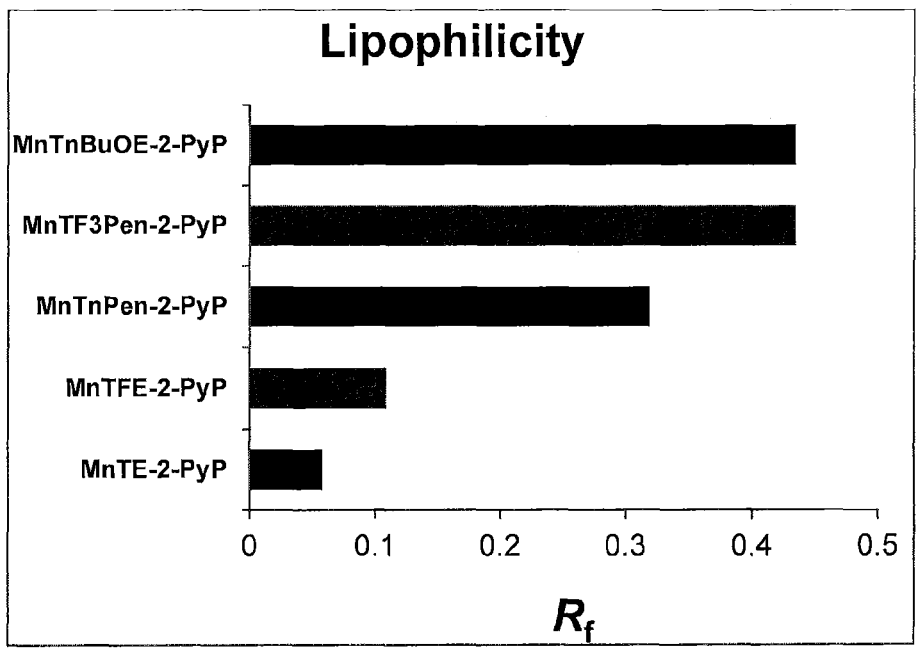
FIG. 6 Lipophilicity of fluoro-MnPs and their non-fluorinated analogs. Fluorination enhances the lipophilicity of MnPs as described with TLC retention factor, R$_f$ (compound path/solvent path). R$_f$ was obtained on silica gel plates using acetonitrile:KNO$_{3(sat)}$:water=8:1:1 as previously described (Tovmasyan A, Carballal S, Ghazaryan R, Melikyan L, Weitner T, Maia C G, Reboucas J S, Radi R, Spasojevic I, Benov L, and Batinic-Haberle I. Rational Design of Superoxide Dismutase (SOD) Mimics: The Evaluation of the Therapeutic Potential of New Cationic Mn Porphyrins with Linear and Cyclic Substituents. *Inorg Chem* 53: 11467-83, 2014). The higher the R$_f$ the more lipophilic the compound is.
Figure 9:
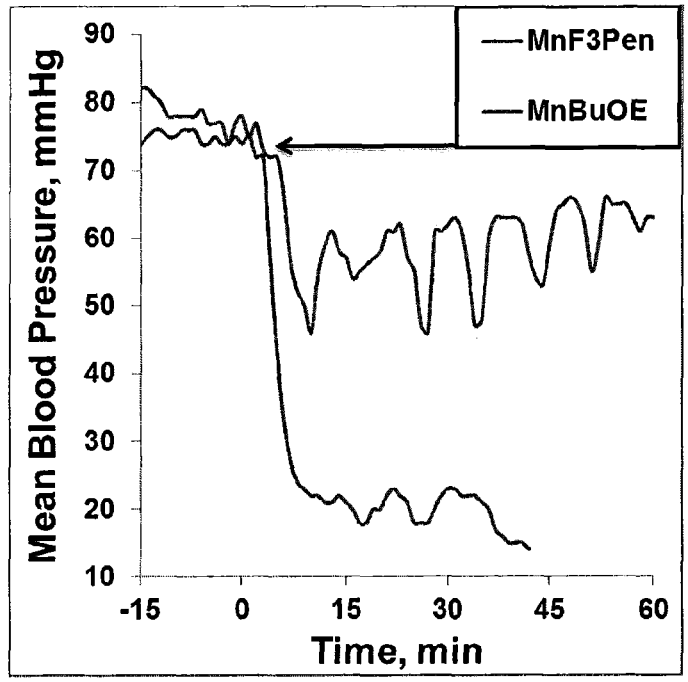
FIG. 9 is a graph of mean blood pressure over time for MnTF$_3$Pen-2-PyP$^{5+}$ (MnF$_3$Pen, Mn4) vs MnTnBuOE-2-PyP$^{5+}$ (MnBuOE, Mn2).

FIG. 1 shows the development of Mn porphyrin based therapeutics. FIG. 4 describes superior properties of fluorinated MnTFE-2-PyP$^{5+}$ (Mn3) over the non-fluorinated analog thereof, MnTnBuOE-2-PyP$^{5+}$ (Mn2). In general, the fluorinated analogs are more able catalysts of ascorbate oxidation and peroxide formation. Importantly, MnTFE-2-PyP$^{5+}$ causes no blood pressure drop when given iv while non-fluorinated MnTnBuOE-2-PyP$^{5+}$ does, FIG. 4. The same is valid for MnTF$_3$Pen-2-PyP (Mn4) vs MnTnBuOE-2-PyP$^{5+}$ (Mn2) (FIG. 9). This would allow for a much facile iv dosing of the fluoro analogs. FIG. 5 shows the ability of various MnPs to catalyze ascorbate oxidation (with subsequent hydrogen peroxide formation which in turn kills tumors) as assessed via determination of the initial rates of ascorbate oxidation. Note that fluorination induces a remarkable increase in ascorbate oxidation rate, which parallels the rate of cytotoxic hydrogen peroxide formation, which in turn parallels the ability of the MnP to kill tumor cells. Such improved ability to kill tumor cells of MnTF$_3$Pen-2-PyP$^{5+}$ as compared to MnTnBuOE-2-PyP$^{5+}$ in 4T1 mouse study is shown in FIG. 2. The greater ability of MnTFE-2-PyP$^{5+}$ (Mn3) than MnTE-2-PyP$^{5+}$ (Mn1) to kill tumor cells is also seen with the same type of mouse experiment. FIG. 6 shows the lipophilicity of fluoro-MnPs and their non-fluorinated analogs. Lipophilicity is the $2^{nd}$ major factor (next to favorable redox properties) that controls therapeutic efficacy of Mn porphyrins.

Figure 7:
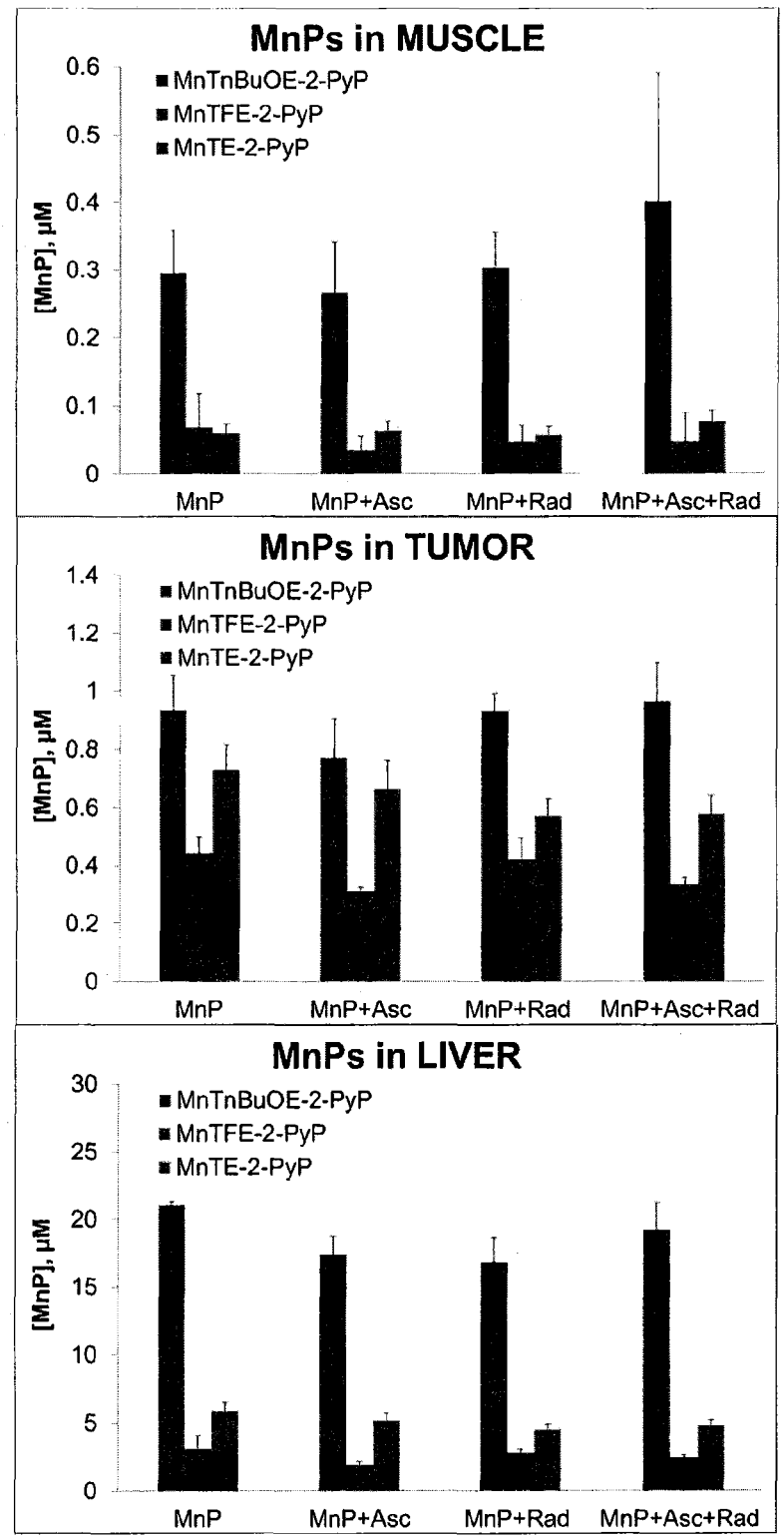
FIG. 7 Bioavailability of fluoro (MnTFE-2-PyP$^{5+}$, MnFE, Mn3) and non-fluoro Mn porphyrins (MnTE-2-PyP$^{5+}$, MnE, Mn1 and MnTnBuOE-2-PyP$^{5+}$, MnBuOE, Mn2) in tumor, muscle and liver. Dramatic differences in bioavailability and reactivity arising from differences in polarities and lipophilicities affect therapeutic effects. The data are obtained from sc flank 4T1 mouse study where the same experimental design was used as in FIGS. 1 and 7 with the only difference being all MnPs are given at 0.2 mg/kg in FIG. 1 and 2 mg/kg in FIG. 7.

FIG. 7 shows the bioavailability of fluoro compounds in tumor, muscle and liver. Against common sense and earlier knowledge, though similarly lipophilic, due to polar interactions with biomolecules in vitro and in vivo (as a result of their excessive polar character), fluoro compounds (e.g., fluorinated Mn porphyrins) do not accumulate in vivo at the same levels as non-fluorinated Mn porphyrins. Yet due to kinetic facilitation of their reactions with cellular biomolecules fluoro compounds produce larger therapeutic effects. Such is the case with MnTE-2-PyP$^{5+}$ (MnE, Mn1) vs MnTFE-2-PyP$^{5+}$ (MnFE, Mn3, Formula II). In all organs (muscle, tumor and liver) MnTBuOE-2-PyP$^{5+}$ (MnBuOE, Mn2) is at higher levels, followed by MnTE-2-PyP$^{5+}$ and MnTFE-2-PyP$^{5+}$, although MnTFE-2-PyP$^{5+}$ produces somewhat a larger effect than MnTE-2-PyP$^{5+}$ while it is less toxic than BMX-001 (MnTnBuOE-2-PyP$^{5+}$). The tumor growth suppression is similar or larger with hydrophilic polar MnTFE-2-PyP$^{5+}$ than lipophilic MnTnBuOE-2-PyP$^{5+}$ though the MnTFE-2-PyP$^{5+}$ distributes ~3-fold less in tumor (FIG. 7) but has twice a higher rate constant for ascorbate oxidation than MnTnBuOE-2-PyP$^{5+}$ (FIGS. 4 and 5, Table 1). Note that y and x axes are on same scale.

Figure 8:
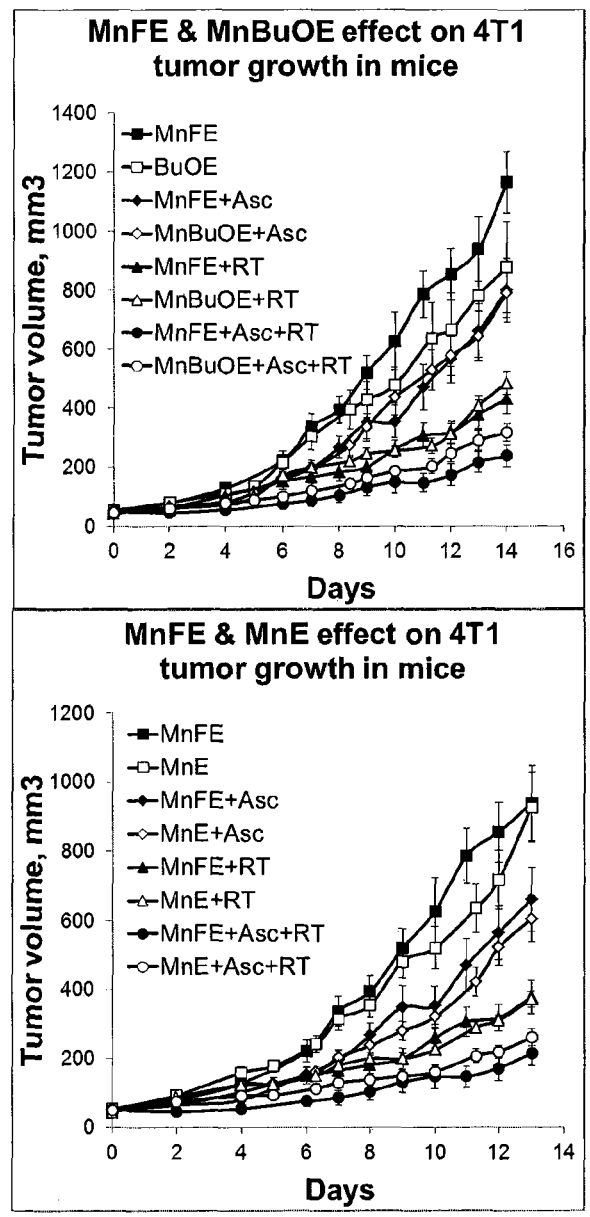
FIG. 8 Anticancer effect of MnTnBuOE-2-PyP$^{5+}$ (MnBuOE, Mn2) vs. MnTE-2-PyP$^{5+}$ (MnE, Mn1) vs MnTFE-2-PyP$^{5+}$ (MnFE, Mn3) in a mouse flank 4T1 mammary cancer model. Conditions are the same as in FIG. 1, except Mn porphyrins are given at 2 mg/kg. Female Balb/c mice were injected subcutaneously (on flank) with 1 million cells. When tumors reached on average volume of 60-80 mm$^3$, the two Mn porphyrins, BMX-001 (MnTnBuOE-2-PyP$^{5+}$) and MnTnFE-2-PyP$^{5+}$ were injected subcutaneously at 2 mg/kg/day and continued daily afterwards; the doses are very low and clinically relevant and indicate catalytic potency of Mn porphyrins. Also the injection of ascorbate (Asc) started at 4 g/kg/day for first 6 days and then at 1 g/kg/day until the 24 hours before the completion of study. 24 hours after the first injection of Mn porphyrins the radiation started at 2.5 Gy per day for 3 days. Fractionated radiation regime was used to better reflect the clinical scenario. Radiation (RT) doses lower than doses that would compare readily to the clinical ones were used in order to be able to see the contribution of radiation and ascorbate of each to the effect of MnPs. Injection of drugs was continued daily. Once the study was completed when mice reached on average 2000 mm$^3$ volume, the mice were sacrificed, and tumors, normal muscle from opposite leg and liver were collected and levels of Mn porphyrins analyzed by LCMS/MS.

FIG. 8 shows the anticancer effect of Mn porphyrins in combination with RT and ascorbate. All the conditions are the same as in FIG. 2 except that Mn porphyrins are injected sc at 2 mg/kg.

The therapeutic effects exhibited by fluoro-substituted Mn porphyrins could not have been anticipated as they are the result of highly complex interplay of their lipophilicity, polarity and redox-properties; the interplay of lipophilicity and polarity which may be affecting their bioavailabilities. All those parameters can influence the kinetics and thermodynamics of reactions of fluoro-substituted Mn porphyrins with key biomolecules such as ascorbate, $H_2O_2$, glutathione and protein thiols which are critically involved in their actions. Of note, the bioavailability vs lipophilicity does not follow trend which we have earlier established with other Mn N-alkylpyridylporphyrins. That is to say that fluoro-substituted Mn porphyrins may be of the same lipophilicities as non-fluoro substituted Mn porphyrins, but distribute very differently as shown in FIG. 7. Yet in addition to such differences, kinetics of their interactions with molecules involved in their mechanism of action control their therapeutic effects. Furthermore, the hydrophilic MnTFE-2-

PyP$^{5+}$ (Mn3) distributes to the lowest level in tumor, yet, is more efficacious (because of the highest rate of the ascorbate oxidation) than lipophilic MnTnBuOE-2-PyP$^{5+}$ and hydrophilic MnTE-2-PyP$^{5+}$ (Mn1) which exhibits the highest accumulation in tumor.

Example 8

Application of Fluorinated Mn Porphyrins to Radiation-Induced Damage.

Figure 10:
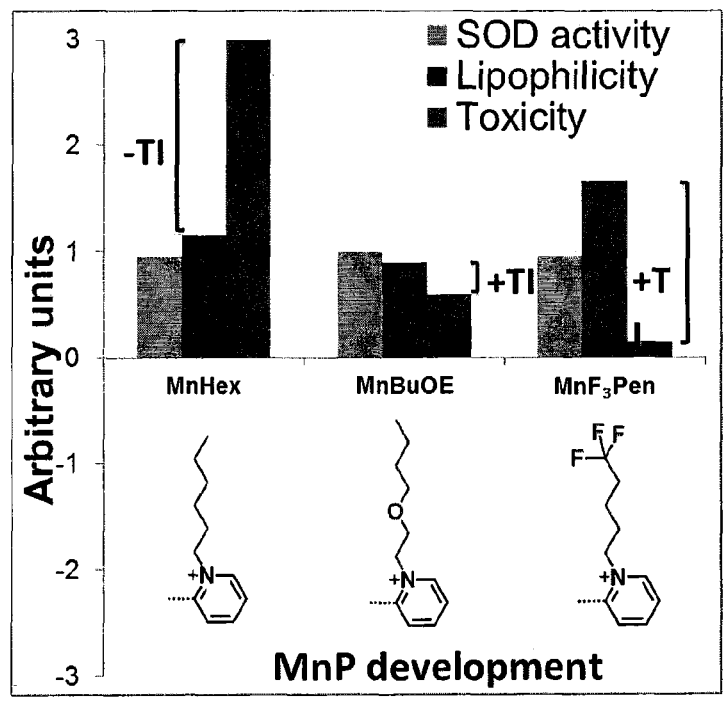
FIG. 10 Estimated therapeutic index, TI of MnPs. The properties of Mn porphyrins (given in arbitrary units) which cumulatively define their therapeutic index: SOD-like activities, lipophilicities and toxicities. Compared are non-fluorinated lead drugs, MnTnHex-2-PyP$^{5+}$ (MnHex) and alkoxyalkyl porphyrin MnTnBuOE-2-PyP$^{5+}$ (MnBuOE, Mn2) to the lipophilic fluorinated analog MnTF$_3$Pen-2-PyP$^{5+}$ (MnF$_3$Pen, Mn4).

Herein we explored the member of a new class of Mn porphyrin-based therapeutics, MnTF$_3$Pen-2-PyP$^{5+}$ (MnTF$_3$Pen, Mn4) (FIG. 1). We have maintained major structural properties that support the redox-activity of MnPs, yet modified peripheral substituents by introducing polar fluorine atoms. FIG. 10 shows the estimated therapeutic index, TI of MnPs. The properties of Mn porphyrins (given in arbitrary units) which cumulatively define their therapeutic index: SOD-like activities, lipophilicities and toxicities. Compared are non-fluorinated lead drugs, alkyl MnTnHex-2-PyP$^{5+}$ (MnTnHex) and alkoxyalkyl porphyrins MnTn-BuOE-2-PyP$^{5+}$ (MnBuOE, Mn2), to the lipophilic fluorinated analog, MnTF$_3$Pen-2-PyP$^{5+}$ (MnF$_3$Pen). Toxicities are evaluated based on the aerobic growth of wild strain *E. coli*—a simple but accurate assay used for over 2 decades to identify the compounds with clinical potential. MnTF$_3$Pen is more lipophilic and more efficacious while less toxic than two non-fluorinated lipophilic analogs. We have demonstrated that fluorination of this analog increased its lipophilicity relative to non-fluorinated, MnTF$_3$Pen.

Mn Porphyrins Radio- and Chemosensitize Breast Tumors.

The role of ascorbate (Vitamin C) in the actions of MnPs as a radioprotector and radiosensitizer was explored. The studies have shown that for breast cancer ascorbate is a powerful tumor sensitizer to both MnTF$_3$Pen-2-PyP$^{5+}$ (MnTF$_3$Pen, Mn4) and radiation (RT) (FIG. 2). It has also been demonstrated and reported that MnP/Asc is toxic to cancer cells disabling their proliferation, but not toxic to different types of normal cells.

A. Maximal Tolerable Dose (MTD) Studies

The analysis of maximal tolerable doses, MTD, of MnTF$_3$Pen-2-PyP$^{5+}$ (Mn4) and ascorbate were done with 0.25, 1, 1.25, 2, 2.5, 4 and 5 mg/kg subcutaneous injection for MnTF$_3$Pen-2-PyP$^{5+}$ and 0.1, 0.5, 1 and 1.5 g/kg intraperitoneal injection for ascorbate. The dose we identified as entirely safe was then given for 2 weeks. Also, a combination of MnTF$_3$Pen-2-PyP$^{5+}$ and ascorbate was tested. A dose above 0.5 mg/kg of MnTF$_3$Pen-2-PyP$^{5+}$ seems to impose some toxicity expressed as hypotonia and reluctance to ambulate. We have thus decided to continue with 0.5 mg/kg which appears as safe non-toxic MTD dose for multiple dosing. 1.5 mg/kg ascorbate showed minor signs of stress, thus 1 g/kg was chosen as MTD.

B. Pharmacokinetic (PK) Studies

Comprehensive PK studies of MnTF$_3$Pen-2-PyP$^{5+}$ (MnF$_3$Pen, Mn4) were conducted at 1 mg/kg. That dose was well tolerated and allowed for the comparison with MnTn-BuOE-2-PyP$^{5+}$ (MnBuOE, Mn2) which PK profile was already obtained by us at such a dose. 3 rats were used per time point. The following time points were tested: 30 min, 1, 2, 6, 24 hours, and 3 and 7 days. The tissues were taken after the rats were perfused with PBS to eliminate blood content of organs and, therefore its interference with blood content of organs. At 6 h, three additional rats were used to assess the effect of perfusion. In addition to plasma, the following organs were analyzed: liver, kidney, prostate, penis, testis, rectum, bladder, and brain. We have collected liver due to Mn porphyrins accumulating at the highest level in this organ; it then serves as a depot to maintain levels of drug in plasma and other organs. We also took the brain because toxicity of Mn porphyrins has been seen at that level present in the brain. Whenever possible the comparison with MnBuOE has been done. The analyses of plasma and organ MnTF$_3$Pen-2-PyP$^{5+}$ (MnF$_3$Pen, Mn4) levels were done with LC-MS/MS as described in Leu et al. "CNS bioavailability and radiation protection of normal hippocampal neurogenesis by a lipophilic Mn porphyrin-based superoxide dismutase mimic, MnBuOE." Redox Biology *Redox Biology* 2017, Volume 12, August 2017, Pages 864-871. MnBuOE was used as internal standard.

Figure 11:
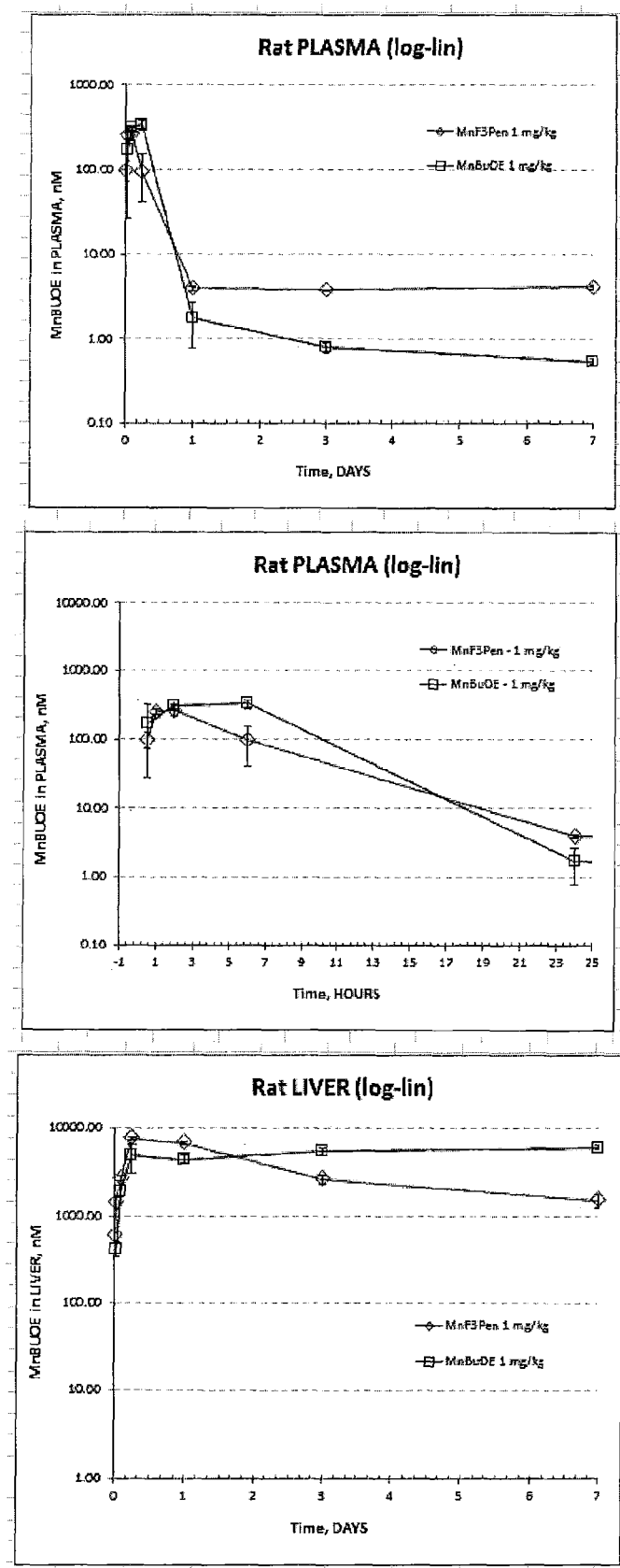
FIG. 11 Pharmacokinetic profiles of MnTF$_3$Pen-2-PyP$^{5+}$ (MnF$_3$Pen, Mn4) in plasma and different organs over 7 days when given at a dose of 1 mg/kg. Whenever possible, the PK profiles of MnF$_3$Pen were compared to MnTnBuOE-2-PyP$^{5+}$ (MnBuOE, Mn2), the drug presently in two clinical trials.
Figure 11:
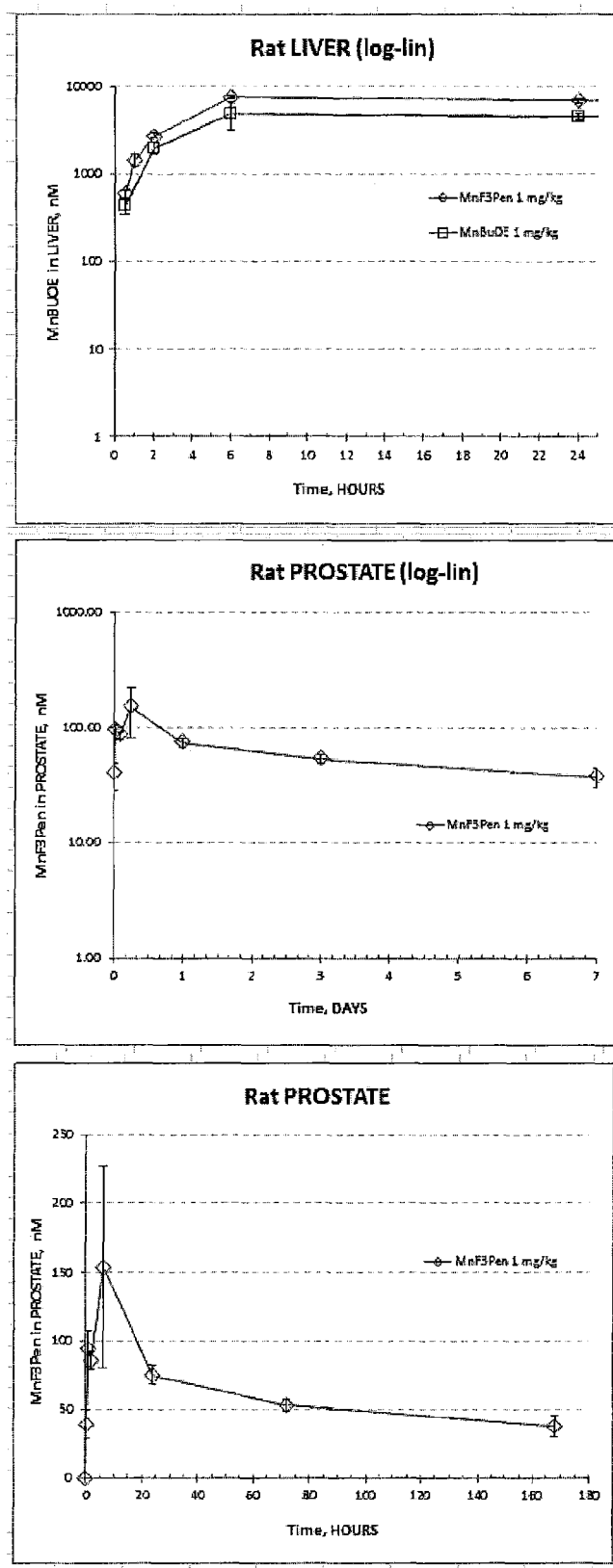
Figure 11:
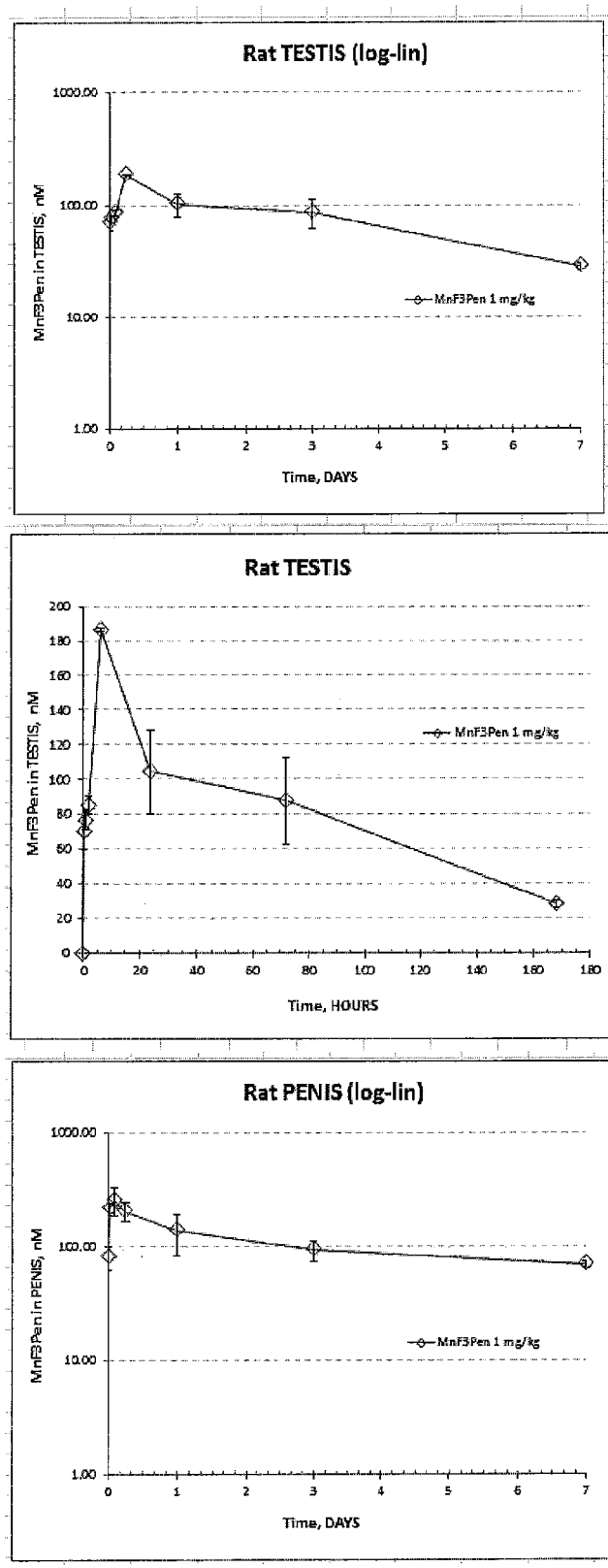

All PK data are presented in FIG. 11. The data show lower accumulation in liver of MnF$_3$Pen than MnBuOE, which would indicate lower systemic toxicity, but longer plasma half-life. Its accumulation in brain (FIG. 12) is similar to MnBuOE as found in another study.

MnF$_3$Pen accumulates in the tissues of interest at levels higher than 100 nM. The highest Cmax of Mn4 was found in bladder (450 nM), followed by penis (250 nM), testes (190 nM), prostate (150 nM) and rectum (105 nM). Based on this and earlier studies the levels are sufficient to justify the radioprotective effects of normal tissues by MnF$_3$Pen. The levels are higher than in salivary glands and about the same as in tongue. The radioprotection of salivary glands and mouth mucosa (including tongue) by MnBuOE was shown in a mouse study C. Efficacy Studies-Radioprotection of Erectile Function and Prostate The weights of rats were followed weekly. Rats of all groups gained weights at similar pace. In addition, rats were carefully monitored with regard to other signs of wellbeing. No negative impact of the RT/Asc therapy on their wellbeing was seen.

Experimental Design

MnTF$_3$Pen-2-PyP$^{5+}$ (MnF$_3$Pen, Mn4). 10 rats per group were studied. MnF$_3$Pen was given at 0.5 mg/kg sc for the first four weeks daily except for weekends, and then twice weekly for the next five weeks. The reduction in dose was due to the slow clearance of all cationic Mn porphyrins from all tissues, being about 1-2 weeks in our study (FIG. 11).

Radiation.

Single radiation dose of 20 Gy was delivered stereotactically, using image guided small animal radiator.

Ascorbate.

Ascorbate was given at 1 g/kg first 3 days daily, then twice weekly.

Apomorphine.

It was used at 0.1 mg/kg (at week 6 and 9).

Erectile Dysfunction

Figure 13:
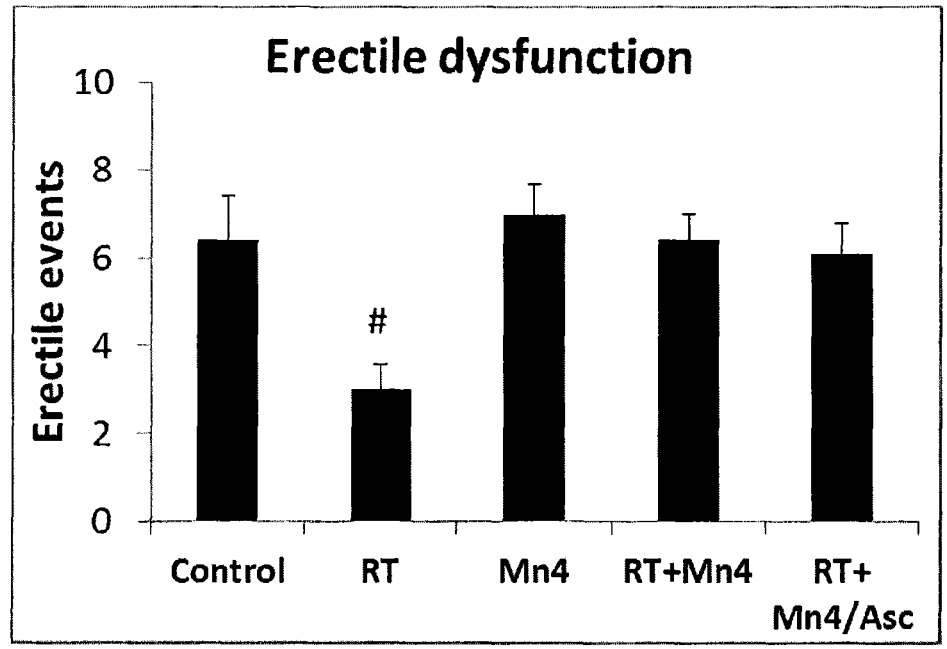
FIG. 13 The erectile function of rats as affected by radiation. The graph shows the erectile events of the control group and treatment groups RT (radiation), MnTF$_3$Pen-2-PyP$^{5+}$ (Mn4), RT+Mn4 (radiation+Mn4), and RT+Mn4/Asc (radiation+Mn4+ ascorbate). Mn4 administration started at 24 hours before RT. Mn4 was given at 0.5 mg/kg sc for the first four weeks daily (except for weekends) and then twice weekly for next five weeks. Single 20 Gy RT dose was given stereotactically. Ascorbate was given at 1 g/kg for the first 3 days daily, then twice weekly. Mn4 fully prevented radiation-induced erectile dysfunction in the presence and absence of ascorbate.

Based on earlier studies, erectile dysfunction has been assessed at 9 weeks. The data clearly show that Mn4 (MnF$_3$Pen-2-PyP$^{5+}$) fully prevents radiation-induced erectile dysfunction (FIG. 13). Moreover, and as shown in FIG. 13, Mn4 fully prevents radiation-induced erectile dysfunction in the absence and presence of ascorbate. Mn4 administration started at 24 hours before RT. Mn4 was given at 0.5 mg/kg sc for the first 4 weeks daily except for weekends, and then twice weekly for the next 5 weeks. Single 20 Gy RT dose was given. Ascorbate was given at 1 g/kg first 3 days daily, then twice weekly. Mn4 fully prevents radiation-induced erectile dysfunction in the presence and absence of ascorbate. Ascorbate addition was not toxic.

Figure 14:
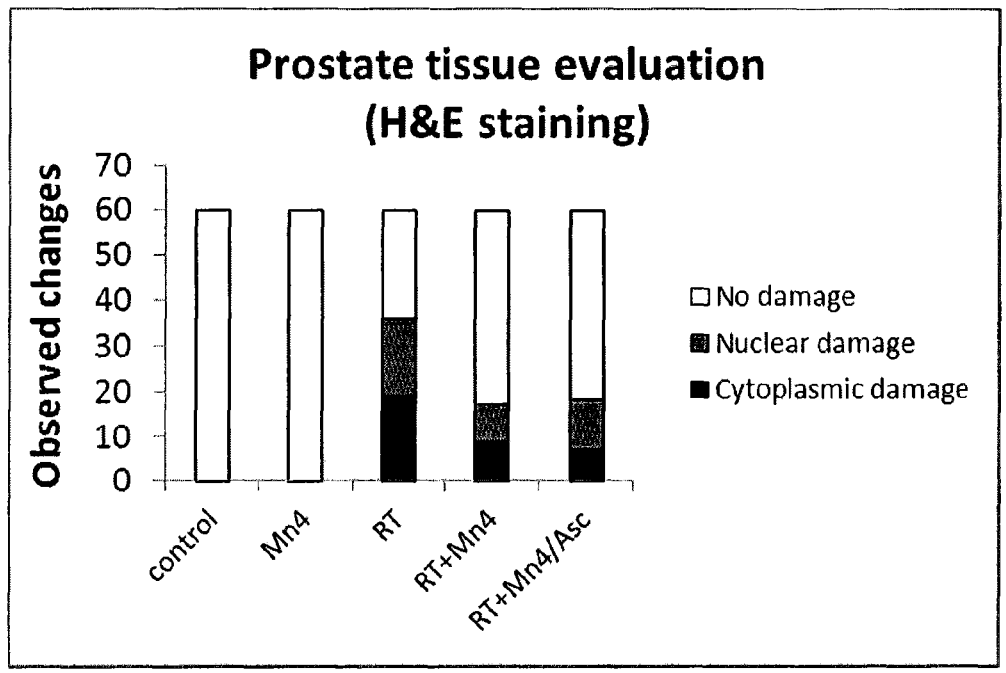
FIG. 14 MnTF$_3$Pen-2-PyP$^{5+}$ (Mn4) suppresses radiation (RT) damage to prostate tissue. Experimental conditions are presented in the FIG. 13 legend. Ascorbate addition was not toxic to prostate tissue in the presence of Mn4 and RT. Tissue was stained with H&E.
Figure 15:
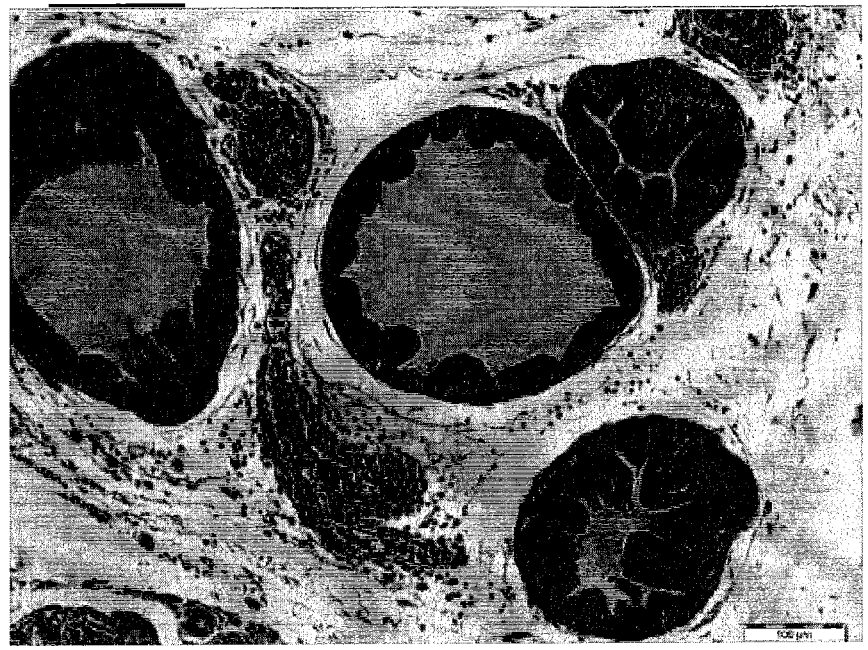
FIG. 15 Radioprotection of prostate by MnTF$_3$Pen-2-PyP$^{5+}$ (Mn4)—histopathology. Morphological changes can be seen in prostate tissue with radiation (RT) alone (panel C), with RT and Mn4 (panel D) and with RT, Mn4 and Asc (panel E) treatments in comparison with control group (panel A) and the group treated with Mn4 alone (panel B) of rats under 100-fold magnification. Mn4 administration started at 24 hours before RT. Mn4 was given at 0.5 mg/kg sc for the first 4 weeks daily except for weekends, and then twice weekly for the next 5 weeks. Single 20 Gy RT dose was given. Ascorbate was given at 1 g/kg for the first 3 days daily, then twice weekly.
Figure 15:
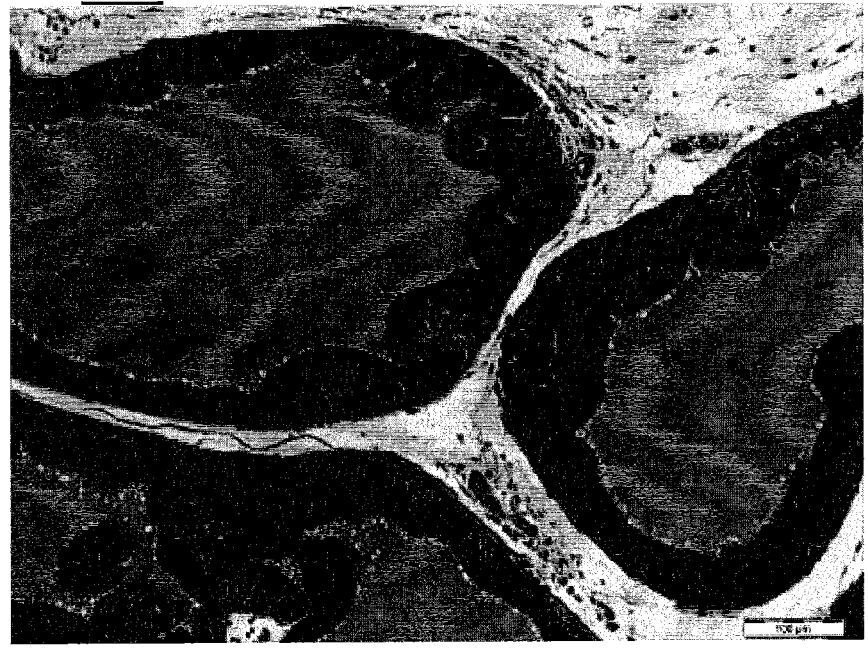

Mn4 is a potent radioprotectant fully preventing radiation-induced damage to erectile function. Moreover, for the first time, we are showing here that ascorbate does not impose toxicity to normal tissue when given along with MnP and radiation—both sources of $H_2O_2$ (FIGS. 14 & 15). In contrast, we have seen suppression of tumor growth and cytotoxicity to tumor cells with such therapeutic strategy. The reason for such differential effects of MnP/Asc/RT on normal and tumor tissue lies in differential levels of $H_2O_2$. The relevance of such data lies in the fact that higher doses of ascorbate can be used to enhance the radio- and chemo sensitization of tumors, without compromising radioprotective properties of Mn4.

Prostate Radioprotection

The tissues were preserved, half of them in formalin and another half snap-frozen for different analyses. Prostate is the only tissue directly radiated and the penile function was known to suffer radiation damage. Indeed, changes were seen on prostate tissue and are quantified in FIGS. 14 & 15. Mn4 exhibited significant radioprotection of prostate tissue. It has though imposed no changes on bladder and rectum pathology with respect to control non-radiated tissues.

Morphological findings with normal prostate glands are as follows:
RT group: Most glands showed large bizarre nuclei and condensed nuclei
RT+Mn4+Asc group: Local glands presented few large bizarre nuclei, some cells showed enlarged irregular nucleus and obvious nucleolus
RT+Mn4+Asc group: Some cells showed enlarged nucleus and obvious nucleolus Radioprotection of Penile Tissue The H&E staining indicates that there might have been fibrotic changes on penile tissue. Thus, we further stained such tissue with Masson trichrome to quantify the extent of fibrosis, analysis is in progress.

Mechanistic Studies

Within the last two years, we have made major advances in understanding differential effects of Mn porphyrins, which is summarized in FIG. 16. We have shown that Mn porphyrins accumulate in tumor up to an order of magnitude more than in normal tissues. It is well documented that tumor has high levels of reactive species (RS) (oxidative stress) relative to normal tissue due to dysfunctional peroxide-removing enzymes. High RS (predominantly long-lived $H_2O_2$) and high level of MnPs are reactants in oxidative modifications of protein cysteines. The larger their amount, the larger is the extent of protein oxidation and in turn the larger is the impact on apoptotic and proliferative pathways. We have shown, using redox proteomics, that numerous proteins are oxidatively modified—S-glutathionylated. Mostly oxidized is NF-kB, then follow MAPK kinases (p38, JNK, ERK, AKT), Nrf2/Keap1 and phosphatase 2A. All of those proteins are critical as they operate—activate or suppress signaling pathways—via oxidation of their cysteines. We have shown that MnPs catalytically oxidize such cysteines in the presence of $H_2O_2$ and GSH. When NF-kB is largely oxidized, and in turn inactivated, the apoptosis is promoted. The catalysis of cysteine oxidation by MnP is in essence glutathione-peroxide like activity of MnPs. We have quantified the abilities of different MnPs to mimic GPx. All redox properties of $MnTE-2-PyP^{5+}$, $MnTnBuOE-2-PyP^{5+}$ $MnTFE-2-PyP^{5+}$, and $MnTF_3Pen-2-PyP^{5+}$ (which are relevant to their ability to radioprotect normal tissue while radiosensitize tumor) are listed in Table 1. It is obvious that $MnTF_3Pen-2-PyP^{5+}$ is similarly redox-active as $MnTnBuOE-2-PyP^{5+}$.

Much lower levels of MnP and $H_2O_2$ in normal tissues result in modest inactivation of NF-kB which in turn results in suppression of inflammation and normal tissue healing (see FIG. 13 for details on differential impact of MnP/RT/Asc on tumor vs normal tissue).

FIG. 16 shows the effects of cationic MnPs on tumor growth in the presence of $H_2O_2$ sources. Tumor is under oxidative stress, due to downregulated or inactive peroxide-removing enzymes. Such tumor environment gets further enhanced by radiation, chemotherapy or when MnP is jointly administered with ascorbate—the major source of $H_2O_2$. High tumor accumulation of MnPs contributes further to the high yield of oxidative modification of protein cysteines in tumor which in turn results in tumor growth suppression. Due to largely functional peroxide-removing enzymes, thus lower $H_2O_2$ levels in normal tissue, and lower MnP accumulation in normal tissues the antiapoptotic processes are preferred. Our proteomic studies identified S-glutathionylation of NF-κB as a major target of $MnP/H_2O_2/$ GSH action when 4T1 breast cancer cells were treated with MnP/Asc. Our recent data on S-glutathionylation and GSSG/2GSH ratio in cancer cells support such impact on NF-kB which results in its inactivation. While not wishing to be bound to any particular theory, the massive inactivation of NF-κB would promote apoptotic processes and greatly contribute to suppression of tumor growth. Given the largely functional endogenous antioxidative defenses in normal tissue, lower yield of NF-κB oxidation and subsequent lower degree of its inactivation, along with lower levels of MnPs would result in normal tissue healing. Effects at the level of NF-κB in normal tissues have been documented with actions on NF-κB with diabetes and stroke, while in cancer with lymphoma and multiple myeloma cellular and glioma animal studies. Effects at the level of Nrf2 have been suggested with radiated normal hematopoietic stem cells.

Mn4 is a potent radioprotectant that can fully prevents radiation-induced damage to erectile function (FIG. 13). Ascorbate did not impose toxicity to erectile function when given along with MnP and radiation—both sources of $H_2O_2$ (FIG. 13). Doses of MnP and ascorbate that we applied here are identical to dosing we usually apply to suppress tumor growth and that are clinically relevant—i.e. they are similar to those presently used in human subjects in clinical trials. Mn4 radioprotects prostate which tissue was directly exposed to 20 Gy single dose radiation (FIGS. 14 and 15). Ascorbate did not impose toxicity to prostate tissue when given along with RT and ascorbate (FIGS. 13, 14 and 15).

Mn4 accumulates in all tissues of interest at levels above 0.1 μM; such levels justify the radioprotective effect of Mn4 (FIG. 11). The highest levels of about 1 μM were seen in liver which serves as a depot to maintain constant levels of MnP in other tissues. Due to slow clearance of drug, we have given Mn4 daily for four weeks post-RT to build up the sufficiently high tissue levels, and continued with twice weekly dosing afterwards. We delivered ascorbate daily for 3 days, then twice per week.

Conversely, tumor growth suppression and cytotoxicity to tumor cells was reported with Mn1 and Mn3 (FIG. 3). The reason for such differential effects of MnP/Asc/RT on normal and tumor tissue lies in differential levels of $H_2O_2$ and MnP, both of which are much higher in tumor (see FIG. 16).

Particularly relevant is that the data demonstrated that higher doses of ascorbate can be used to enhance the radio- and chemo sensitization of tumors (allowing for reduced RT and chemotherapy dosing), without compromising radioprotective properties of Mn4.

That which is claimed is:
1. A compound of Formula I:
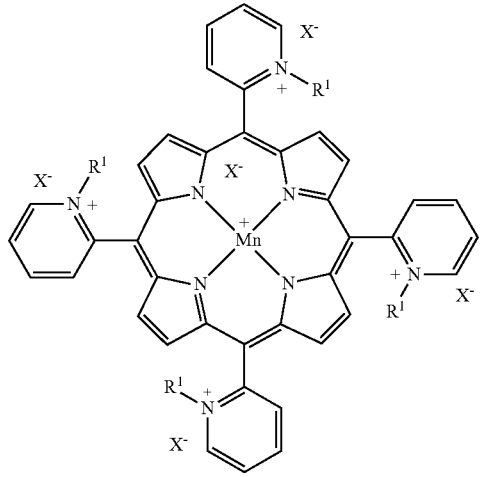
(I)
wherein:
R¹ is a C3-C8 alkyl that is substituted with at least 1 fluorine, or R¹ is 2-fluoroethyl; and
X is an anion.
2. The compound of claim 1, wherein the compound has a structure represented by Formula II, Formula III, Formula IV, Formula V, Formula VI, Formula VII, Formula VIII, Formula IX, or Formula X:
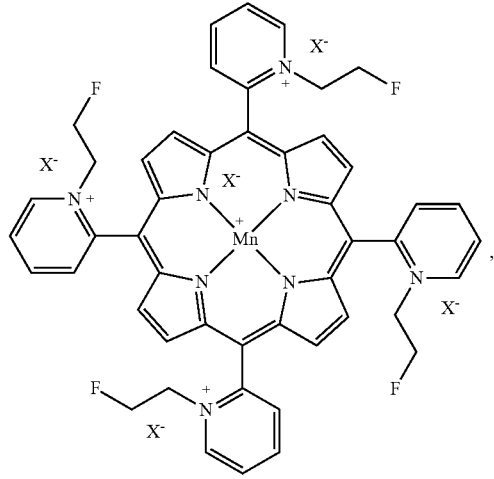
(II)
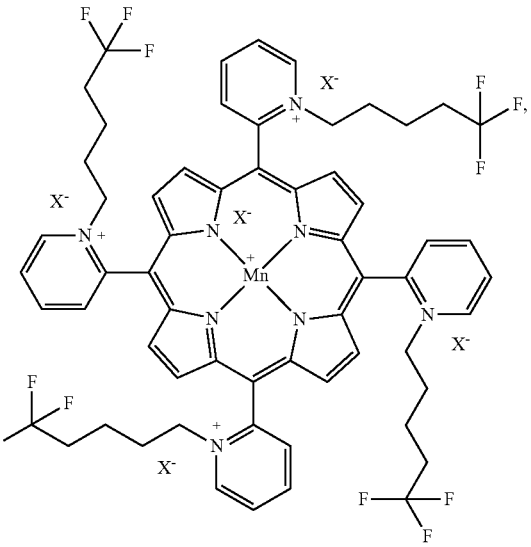
(III)
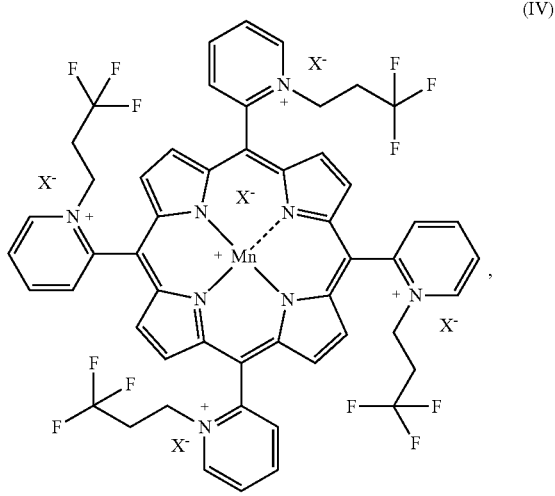
(IV)
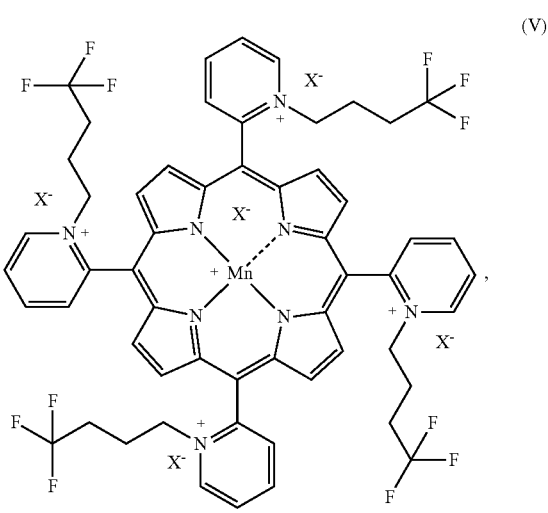
(V)

(VI)
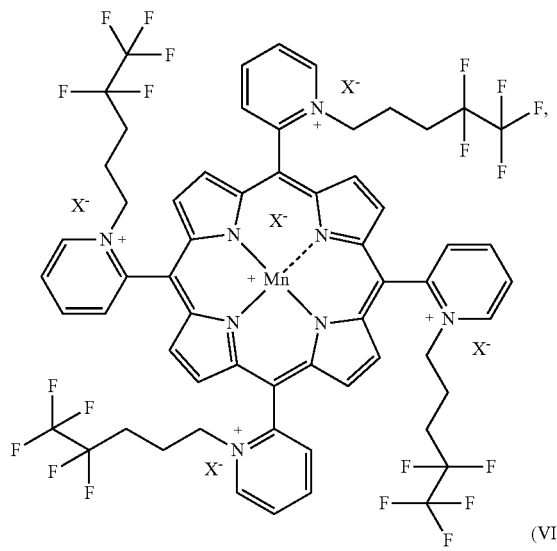

(VII)
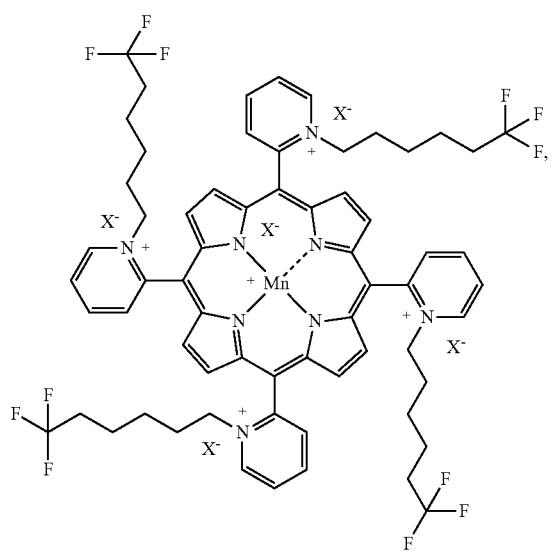

(VIII)
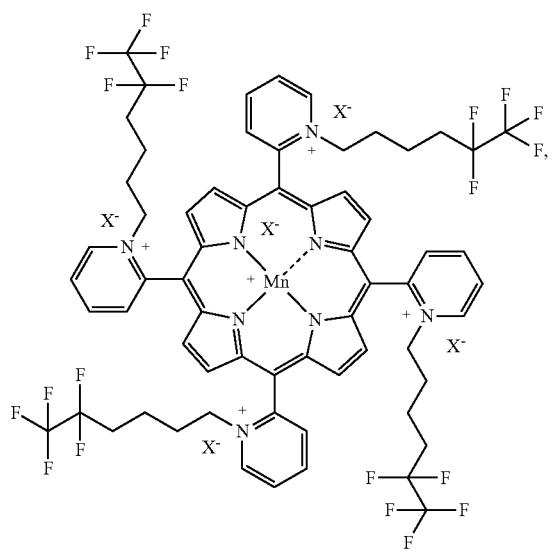

(IX)
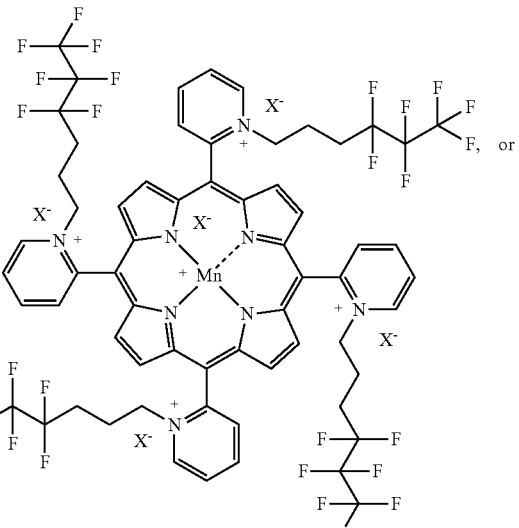, or (X)
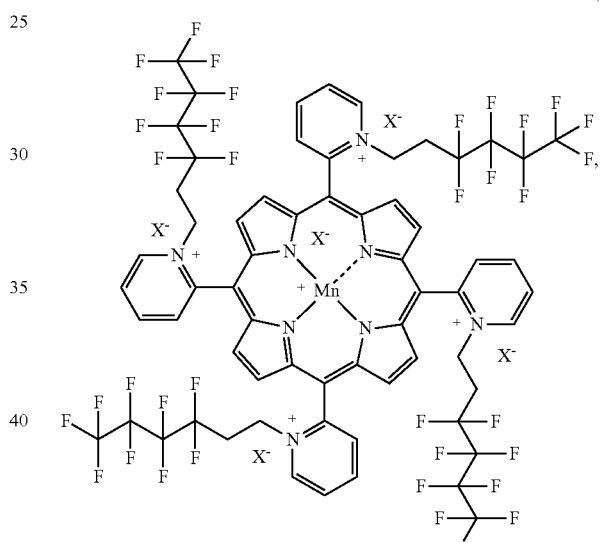

wherein X is an anion.

3. A composition comprising a compound of claim 2 in a pharmaceutically acceptable carrier, wherein at least 90, 91, 92, 93, 94, 95, 96, 97, 98, or 99 percent by weight of all metalloporphyrins in said composition consist of said compound of Formula I, Formula II, Formula III, Formula IV, Formula V, Formula VI, Formula VII, Formula VIII, Formula IX, or Formula X.

4. A method for inhibiting breast or prostate tumor growth and/or treating breast or prostate cancer in a subject comprising administering the compound of claim 1 to said subject in an amount effective to inhibit the breast or the prostate tumor growth and/or treat the breast or the prostate cancer.

5. The method of claim 4, further comprising administering to the subject the compound in combination with at least one additional agent and/or therapy.

6. The method of claim 5, wherein the at least one additional agent and/or therapy comprises administering ascorbate, radiation therapy, and/or chemotherapy.

7. The method of claim 5, wherein the at least one additional agent and/or therapy comprises administering ascorbate and radiation therapy.

8. The method of claim 6, wherein ascorbate is administered to the subject in an amount of about 0.1 mg/kg to about 5 g/kg.

9. The method of claim 4, wherein the subject is a human subject.

10. The method of claim 4, wherein the method inhibits the breast tumor growth and/or treats the breast cancer.

11. The method of claim 4, wherein the compound is administered to the subject in an amount of about 0.01 mg/kg to about 5 mg/kg.

12. A method of treating and/or preventing one or more side effects associated with radiation and/or chemotherapy exposure in a subject during and/or following radiation and/or chemotherapy exposure, the method comprising:
administering to the subject prior to, during, and/or after radiation and/or chemotherapy exposure the compound of claim 1, and optionally ascorbate.

13. The method of claim 12, wherein the compound is administered to the subject in an amount of about 0.01 mg/kg to about 5 mg/kg.

14. The method of claim 12, wherein ascorbate is administered to the subject in an amount of about 0.1 mg/kg to about 5 g/kg.

15. The method of claim 12, wherein the compound and/or ascorbate is administered to the subject about 30 minutes to about 4 days or about 1 hour to about 48 hours prior to the subject being exposed to radiation and/or chemotherapy.

16. The method of claim 12, wherein the compound and/or ascorbate is administered to the subject during and/or after the subject is exposed to radiation and/or chemotherapy.

17. The method of claim 16, wherein the compound and/or ascorbate is administered 1, 2, 3, 4, 5, 6, or 7 times per week after the subject is exposed to radiation and/or chemotherapy.

18. The method of claim 12, wherein the radiation exposure comprises a total dose of about 5 to about 100 Gy.

19. The method of claim 12, wherein the method treats and/or prevents radiation-induced normal tissue injury in the subject.

20. The method of claim 12, wherein the method treats and/or prevents in the subject tissue damage due to and/or caused by inflammation.

* * * * *

UNITED STATES PATENT AND TRADEMARK OFFICE
CERTIFICATE OF CORRECTION

PATENT NO. : 11,344,574 B2
APPLICATION NO. : 16/645907
DATED : May 31, 2022
INVENTOR(S) : Batinic-Haberle et al.

It is certified that error appears in the above-identified patent and that said Letters Patent is hereby corrected as shown below:

In the Specification

Column 2, Lines 38-39: Please correct "paragraphs and [0049]" to read --paragraphs [0048] and [0049]--

Column 3, Line 30: Please correct "Wagner, et al. (2009) 1" to read --Wagner, et al. (2009) J.--

Column 6, Line 64: Please correct "$PF_6$" or Cl-" to read --$PF_6^-$ or Cl$^-$--

Column 9, Line 56: Please correct "which has as" to read --which has Cl$^-$ as--

Column 10, Lines 17-18: Please correct "average 2000 mm$^3$" to read --average ~2000 mm$^3$--

Column 11, Line 51: Please correct "average 2000 mm$^3$" to read --average ~2000 mm$^3$--

Column 13, Line 41: Please correct "d 5%" to read --± 5%--

Column 26, Line 48: Please insert a paragraph break between "8%." and "Ingredient"

Column 33, Lines 60-61: Please correct "MnTF$_3$Pen-2-PyP$^{5+}$: the solution" to read --MnTF$_3$Pen-2-PyP$^{5+}$: to the solution--

Column 34, Line 1, Title of Scheme 2: Please correct "porphyroms" to read --porphyrins--

Signed and Sealed this
Fifteenth Day of November, 2022

Katherine Kelly Vidal
*Director of the United States Patent and Trademark Office*

CERTIFICATE OF CORRECTION (continued)
U.S. Pat. No. 11,344,574 B2

Page 2 of 2

Column 34, Lines 2-25: Please delete the formula of Step 3.1 and replace with the following:

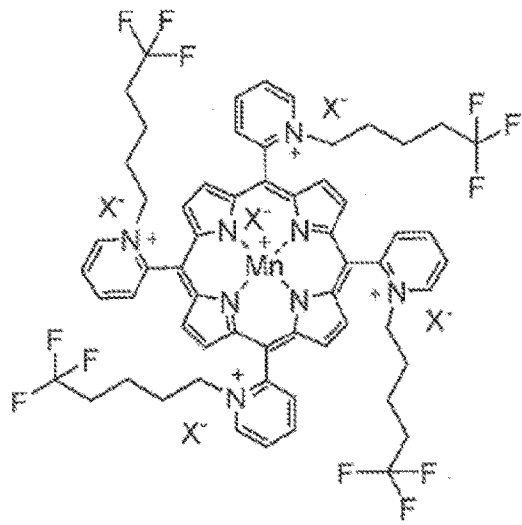

Columns 37-38, Lines 1-20, Scheme IIA: Please delete Scheme IIA and replace with the following:

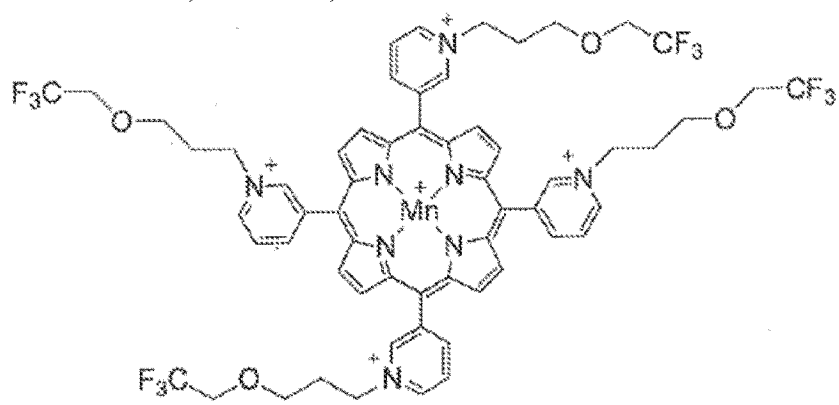

Column 37, Line 26: Please correct "Scheme HA" to read --Scheme IIA--

Column 38, Line 51: Please correct "$E_{112}$" to read --$E_{1/2}$--

Column 38, Line 53: Please correct "P/Mn$^{II}$P" to read --Mn$^{III}$P/Mn$^{II}$P--